(12) United States Patent
Abe et al.

(10) Patent No.: US 7,960,039 B2
(45) Date of Patent: Jun. 14, 2011

(54) AMINO COMPOUND FOR ORGANIC LIGHT-EMITTING DEVICE AND ORGANIC LIGHT-EMITTING DEVICE INCLUDING THE SAME

(75) Inventors: Shigemoto Abe, Tokyo (JP); Akihiro Senoo, Kawasaki (JP); Naoki Yamada, Toyko (JP); Chika Negishi, Yokosuka (JP)

(73) Assignee: Canon Kabushiki Kaisha, Tokyo (JP)

( * ) Notice: Subject to any disclaimer, the term of this patent is extended or adjusted under 35 U.S.C. 154(b) by 520 days.

(21) Appl. No.: 11/690,221

(22) Filed: Mar. 23, 2007

(65) Prior Publication Data

US 2007/0228941 A1    Oct. 4, 2007

(30) Foreign Application Priority Data

Mar. 28, 2006  (JP) ................................. 2006-088351
Feb. 1, 2007   (JP) ................................. 2007-023115

(51) Int. Cl.
*H01J 1/62* (2006.01)
*C07D 213/26* (2006.01)

(52) U.S. Cl. ........ 428/690; 428/917; 313/504; 546/285; 564/427

(58) Field of Classification Search ..................... None
See application file for complete search history.

(56) References Cited

U.S. PATENT DOCUMENTS

| 7,229,702 | B2 | 6/2007 | Saitoh | |
|---|---|---|---|---|
| 7,241,513 | B2 | 7/2007 | Suzuki | |
| 2004/0137267 | A1* | 7/2004 | Igarashi et al. | 428/690 |
| 2005/0236974 | A1 | 10/2005 | Suzuki | |
| 2005/0236977 | A1* | 10/2005 | Yamada et al. | 313/504 |
| 2005/0244670 | A1 | 11/2005 | Saitoh | |
| 2006/0068221 | A1 | 3/2006 | Saitoh | |
| 2006/0121312 | A1 | 6/2006 | Yamada | |
| 2006/0134425 | A1 | 6/2006 | Suzuki | |
| 2006/0166034 | A1 | 7/2006 | Saitoh | |
| 2007/0111029 | A1 | 5/2007 | Yamada | |

FOREIGN PATENT DOCUMENTS

| JP | 11144875 | 5/1999 |
|---|---|---|
| JP | 2003048868 | 2/2003 |
| JP | 2005060382 A * | 3/2005 |
| JP | 2005119994 | 5/2005 |
| WO | WO 2007072952 A1 * | 6/2007 |

OTHER PUBLICATIONS

Machine translation of JP-2005-060382. Date: Mar. 10, 2005.*
Machine translation of JP-2005-119994. Date: May 12, 2005.*

* cited by examiner

*Primary Examiner* — D. Lawrnece Tarazano
*Assistant Examiner* — Andrew K Bohaty
(74) *Attorney, Agent, or Firm* — Fitzpatrick, Cella, Harper & Scinto

(57) ABSTRACT

An amino compound for an organic light-emitting device of general formula [1]:

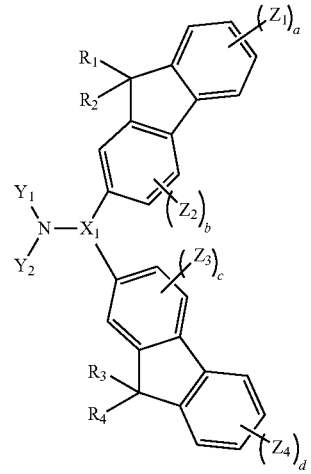

[Chemical formula 1]

[1]

wherein $X_1$ is bonded to the pair of fluorenyl groups at meta-positions to each other and is substituted or unsubstituted aromatic ring, fused polycyclic ring, or heterocyclic ring; $Y_1$ and $Y_2$ are each substituted or unsubstituted alkyl, aryl, or heterocyclic and are the same or different; $Z_1$ to $Z_4$ are each hydrogen, halogen, or substituted or unsubstituted alkyl, aralkyl, alkenyl, alkynyl, alkoxy, aryl, or heterocyclic and are the same or different; $R_1$ to $R_4$ are each hydrogen, halogen, or substituted or unsubstituted alkyl, aryl, or heterocyclic and are the same or different; a and d are each 1 to 4; and b and c are each 1 to 3.

4 Claims, 3 Drawing Sheets

AMINO COMPOUND FOR ORGANIC LIGHT-EMITTING DEVICE AND ORGANIC LIGHT-EMITTING DEVICE INCLUDING THE SAME

BACKGROUND OF THE INVENTION

1. Field of the Invention

The present invention relates to an amino compound for an organic light-emitting device and an organic light-emitting device including the same. More specifically, the present invention relates to an organic light-emitting device that emits light by applying an electric field to a thin film made of an organic compound.

2. Description of the Related Art

In organic light-emitting devices, a thin film containing a fluorescent organic compound or a phosphorescent organic compound is sandwiched between an anode and a cathode, and holes and electrons are injected from the electrodes to the thin film.

Accordingly, excitons of the fluorescent compound or the phosphorescent compound are generated, and the device uses light emitted when these excitons return to the ground state.

Recently, a marked development has been achieved in such an organic light-emitting device. According to the features of the organic light-emitting device, a high luminance can be produced with a low applied voltage, a diverse emission wavelength can be provided, a high-speed response can be realized, and the thickness and the weight of the device can be reduced, thus suggesting the possibility of a wide variety of applications.

In the current situation, however, it is necessary to yield an optical output with a higher luminance or a higher conversion efficiency. In addition, conventional organic light-emitting devices still have many problems in terms of durability, for example, a change over time due to long-term use, and degradation caused by an atmospheric gas containing oxygen, moisture, or the like.

When applying an organic light-emitting device to a full-color display or the like, light emissions of blue, green, and red with satisfactory color purity are also required. However, conventional devices have not yet achieved satisfactory properties.

Japanese Patent Laid-Open Nos. 11-144875, 2003-48868, and 2005-119994 disclose examples of a material containing a fluorene compound and an organic light-emitting device. However, Japanese Patent Laid-Open No. 11-144875 (JP'875) discloses, as an aryl-substituted aryl group that is substituted at the amino position of a difluorenylamine, only a phenyl group which is substituted at the 4th position with a phenyl group. JP'875 does not disclose a compound in which fluorenyl groups are substituted at the 3rd position and the 5th position, or at the 2nd position and the 6th position of the phenyl group.

A compound as in JP'875 in which a phenyl group of N,N-difluorenyl-N-phenylamine is substituted with a phenyl group has a molecular weight which is less than that of a compound in which the phenyl group of N,N-difluorenyl-N-phenylamine is substituted with a fluorenyl group. The former compound as disclosed in JP'875 tends to have a lower glass transition temperature (Tg) than the latter compound.

Therefore, it is believed that the latter compound, which is substituted with a fluorenyl group, provides a more dimensionally stable film having better properties and is more suitable for an organic light-emitting device. Furthermore, a fluorenyl group has a conjugated plane larger than that of a phenyl group, and, thus, the overlap of orbital electrons is increased. Accordingly, charge-transporting capacity is also increased, and a high electron or hole mobility can be expected.

Accordingly, it is believed that the introduction of a fluorenyl group provides a film with high Tg and high charge mobility.

In general, as orbital conjugation extends, band gap becomes narrower, and, conjugation becomes narrower, the band gap widens. Furthermore, in general, when aromatic rings are bonded at the ortho-position or the para-position, conjugation is extended. On the other hand, when aromatic rings are bonded at the meta-position, conjugation is not extended.

In the compound in which the 4th position of a phenyl group of N,N-difluorenyl-N-phenylamine is substituted with a phenyl group as in JP'875, conjugation extends from the phenyl group substituted at the 4th position to the two fluorenyl groups via the phenyl group and the amine, thereby narrowing the band gap. In contrast, when two fluorenyl groups are bonded at the 3rd position and the 5th position, or at the 2nd position and the 6th position, i.e., at the meta positions, conjugation is not extended, thereby providing a wide band gap.

In general, when a compound is used as a hole injection/transporting material and the band gap of the material is narrow, the band gap of a luminescent layer also tends to be narrow. In this embodiment, it is difficult to select a host compound in a device requiring a relatively wide band gap, for example, blue fluorescence or phosphorescence. When a compound is used as a host material, the material must have a band gap wider than that of a guest material. In particular, in phosphorescent materials, the energy level at the lowest excited triplet state (T1) must be higher than the T1 of the guest. Accordingly, the phosphorescent materials require a wide band gap.

SUMMARY OF THE INVENTION

The present invention provides a novel amino compound that maintains a wide band gap by bonding two fluorenyl groups at the meta position of an amino-substituted aryl group that can be used in a range of red to blue fluorescence and in a range of red to green phosphorescence.

The present invention provides a novel amino compound with a high Tg and a high mobility.

The present invention also provides an organic light-emitting device that realizes an optical output with an extremely high efficiency and a high luminance using the amino compound. The present invention provides an organic light-emitting device having high durability.

The present invention provides an organic light-emitting device that can be easily produced at a relatively low cost.

(1) Accordingly, the present invention provides an amino compound for an organic light-emitting device represented by general formula [1]:

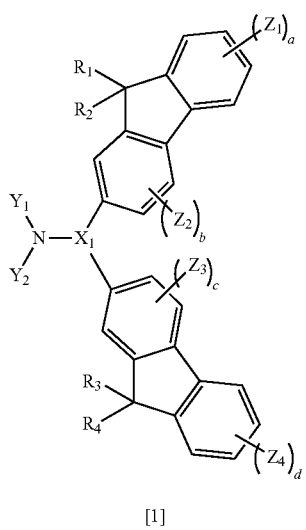

[1]

wherein $X_1$ represents a substituted or unsubstituted aromatic ring, fused polycyclic ring, or heterocyclic ring; wherein in said formula [1] said substituted or unsubstituted aromatic ring, fused polycyclic ring, or heterocyclic ring is bonded to the pair of fluorenyl groups at meta-positions to each other; $Y_1$ and $Y_2$ each represent a substituted or unsubstituted alkyl group, aryl group, or heterocyclic group and are the same or different; $Z_1$, $Z_2$, $Z_3$, and $Z_4$ each represent a group selected from a hydrogen atom, a halogen group, and a substituted or unsubstituted alkyl group, aralkyl group, alkenyl group, alkynyl group, alkoxy group, aryl group, and heterocyclic group and are the same or different; $R_1$ to $R_4$ each represent a hydrogen atom, a halogen atom, or a substituted or unsubstituted alkyl group, aryl group, or heterocyclic group and are the same or different; a and d each represent an integer of 1 to 4; and b and c each represent an integer of 1 to 3.

(2) The present invention provides an amino compound for an organic light-emitting device according to item (1) represented by general formula [2]:

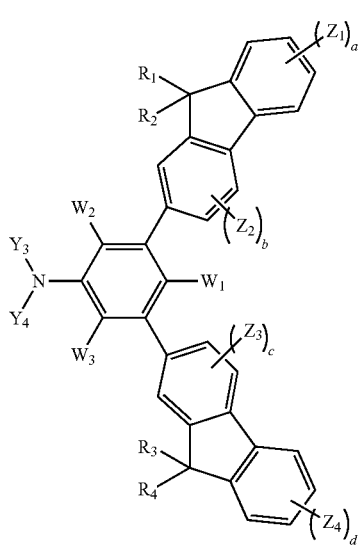

[2]

wherein $W_1$, $W_2$, and $W_3$ each represent a group selected from the group consisting of a hydrogen atom, a deuterium atom, a halogen atom, and a substituted or unsubstituted alkyl group and alkoxy group; $Y_3$ and $Y_4$ each represent a substituted or unsubstituted alkyl group, aryl group, or heterocyclic group; and $Y_3$ and $Y_4$ are different from each other.

(3) The present invention provides an amino compound for an organic light-emitting device according to item (1) represented by general formula [3]:

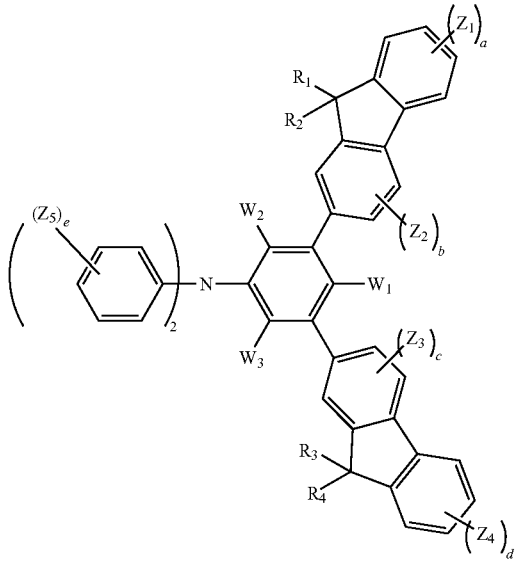

[3]

wherein $W_1$, $W_2$, and $W_3$ each represent a group selected from the group consisting of a hydrogen atom, a deuterium atom, a halogen atom, and a substituted or unsubstituted alkyl group and alkoxy group; $Z_5$ represents a group selected from a hydrogen atom, a halogen group, a substituted or unsubstituted alkyl group, aralkyl group, alkenyl group, alkynyl group, alkoxy group, aryl group, and heterocyclic group; e represents an integer of 0 to 5; and carbon atoms consisting of the two phenyl groups substituted with $Z_5$ are optionally substituted with nitrogen atoms.

(4) The present invention provides an amino compound for an organic light-emitting device according to item (1) represented by general formula [4]:

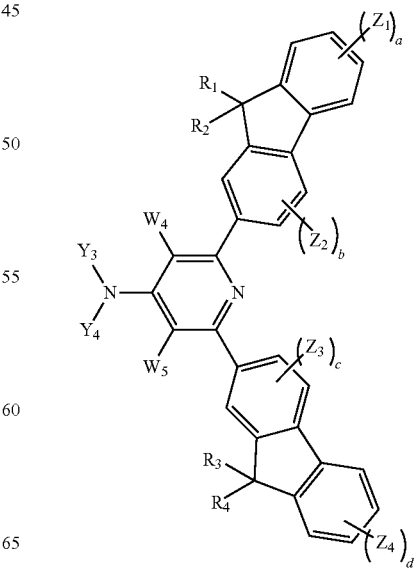

[4]

wherein $W_4$ and $W_5$ each represent a group selected from the group consisting of a hydrogen atom, a deuterium atom, a halogen atom, and a substituted or unsubstituted alkyl group and alkoxy group; $Y_3$ and $Y_4$ each represent a substituted or unsubstituted alkyl group, aryl group, or heterocyclic group; and $Y_3$ and $Y_4$ are different from each other.

(5) The present invention provides an amino compound for an organic light-emitting device according to item (1) represented by general formula [5]:

[Chemical formula 5]

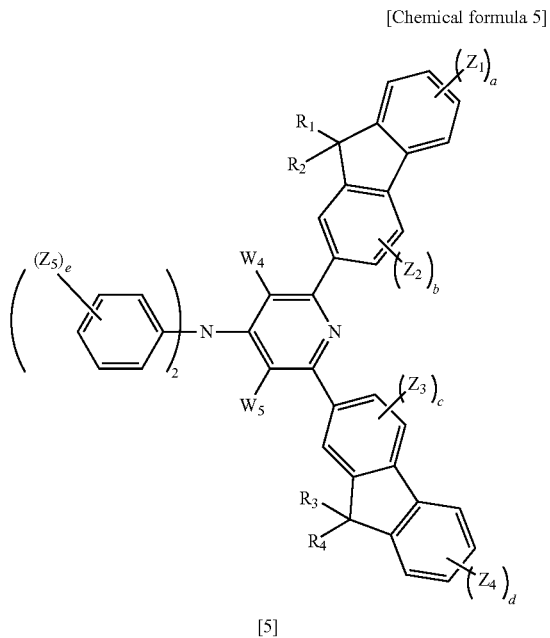

[5]

wherein $W_4$ and $W_5$ each represent a group selected from the group consisting of a hydrogen atom, a deuterium atom, a halogen atom, and a substituted or unsubstituted alkyl group; $Z_5$ represents a group selected from a hydrogen atom, a halogen group, a substituted or unsubstituted alkyl group, aralkyl group, alkenyl group, alkynyl group, alkoxy group, aryl group, and heterocyclic group; e represents an integer of 0 to 5; and carbon atoms consisting of the two phenyl groups substituted with $Z_5$ are optionally substituted with nitrogen atoms.

(6) The present invention provides an organic light-emitting device including a pair of electrodes composed of an anode and a cathode, and an organic compound layer sandwiched between the pair of electrodes, wherein the organic compound layer contains the amino compound for an organic light-emitting device according to item (1).

(7) The present invention provides the organic light-emitting device according to item (6), wherein the organic compound layer is a hole injection layer or a hole-transporting layer.

(8) The present invention provides the organic light-emitting device according to item (6), wherein the organic compound layer is a luminescent layer.

(9) The present invention provides the organic light-emitting device according to item (8), wherein the luminescent layer is composed of at least a host and a guest and the host is formed of the amino compound for an organic light-emitting device.

Organic light-emitting devices including the amino compounds of the present invention represented by general formulae [1] to [5] provide highly efficient light emission with a low applied voltage. The organic light-emitting devices also have high durability.

Further features of the present invention will become apparent from the following description of exemplary embodiments with reference to the attached drawings.

DESCRIPTION OF THE EMBODIMENTS

Figure 1:
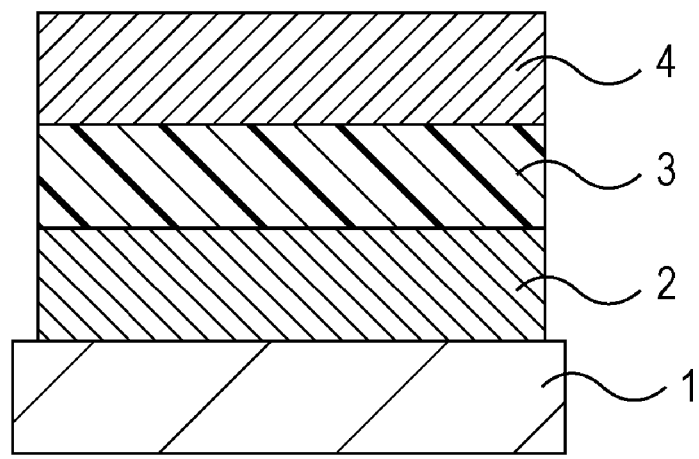
FIG. 1 is a cross-sectional view showing an organic light-emitting device according to an embodiment of the present invention.

An amino compound for an organic light-emitting device of the present invention is represented by general formula [1]:

[Chemical formula 1]

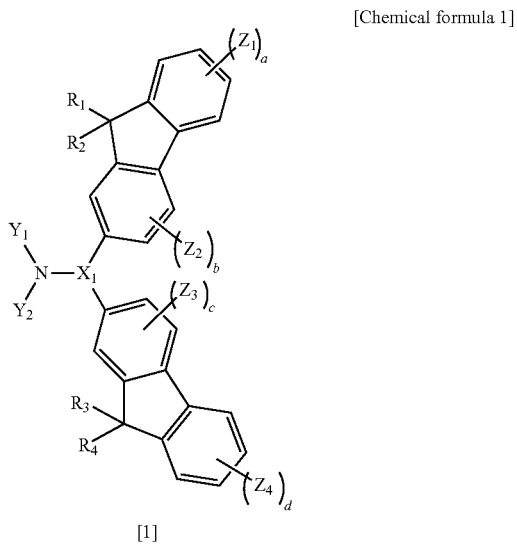

[1]

wherein $X_1$ represents a substituted or unsubstituted aromatic ring, fused polycyclic ring, or heterocyclic ring; wherein in said formula [1] said substituted or unsubstituted aromatic ring, fused polycyclic ring, or heterocyclic ring is bonded to the pair of fluorenyl groups at meta-positions to each other; $Y_1$ and $Y_2$ each represent a substituted or unsubstituted alkyl group, aryl group, or heterocyclic group and are the same or different; $Z_1$, $Z_2$, $Z_3$, and $Z_4$ each represent a group selected from a hydrogen atom, a halogen group, and a substituted or unsubstituted alkyl group, aralkyl group, alkenyl group, alkynyl group, alkoxy group, aryl group, and heterocyclic group and are the same or different; $R_1$ to $R_4$ each represent a hydrogen atom, a halogen atom, or a substituted or unsubstituted alkyl group, aryl group, or heterocyclic group and are the same or different; a and d each represent an integer of 1 to 4; and b and c each represent an integer of 1 to 3.

An amino compound for an organic light-emitting device of the present invention is represented by general formula [2]:

[Chemical formula 2]

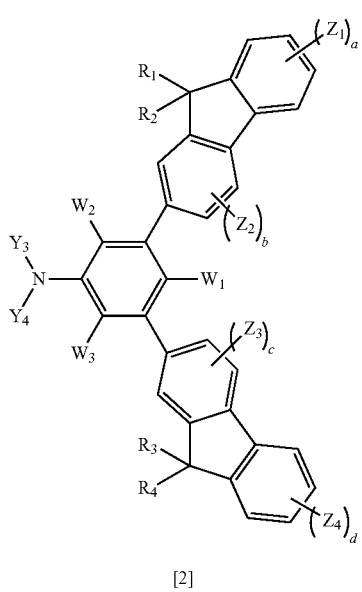

[2]

wherein $W_1$, $W_2$, and $W_3$ each represent a group selected from the group consisting of a hydrogen atom, a deuterium atom, a halogen atom, and a substituted or unsubstituted alkyl group and alkoxy group; $Y_3$ and $Y_4$ each represent a substituted or unsubstituted alkyl group, aryl group, or heterocyclic group; $Y_3$ and $Y_4$ are different from each other; and $Z_1$, $Z_2$, $Z_3$, $Z_4$, $R_1$, $R_2$, $R_3$, $R_4$, a, d, b, and c are the same as the above.

An amino compound for an organic light-emitting device of the present invention is represented by general formula [3]:

[Chemical formula 3]

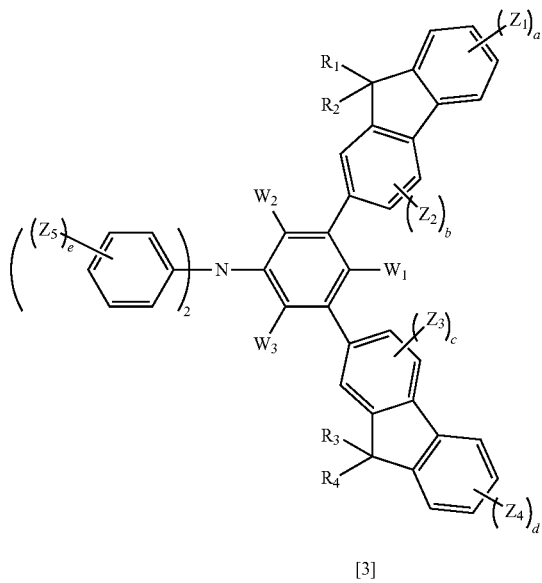

[3]

wherein $Z_5$ represents a group selected from a hydrogen atom, a halogen group, a substituted or unsubstituted alkyl group, aralkyl group, alkenyl group, alkynyl group, alkoxy group, aryl group, and heterocyclic group; e represents an integer of 0 to 5; carbon atoms consisting of the two phenyl groups substituted with $Z_5$ are optionally substituted with nitrogen atoms; and $W_1$, $W_2$, $W_3$, $Z_1$, $Z_2$, $Z_3$, $Z_4$, $R_1$, $R_2$, $R_3$, $R_4$, a, d, b, and c are the same as the above.

An amino compound for an organic light-emitting device of the present invention is represented by general formula [4]:

[Chemical formula 4]

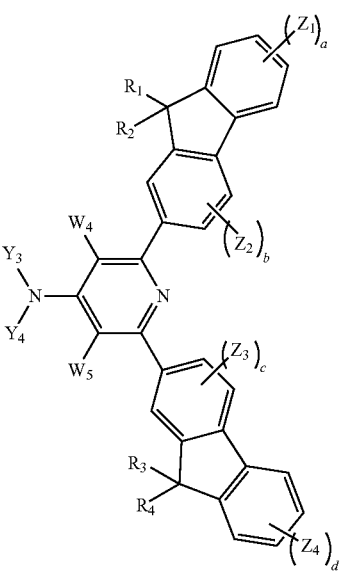

[4]

wherein $W_4$ and $W_5$ each represent a group selected from the group consisting of a hydrogen atom, a deuterium atom, a halogen atom, and a substituted or unsubstituted alkyl group and alkoxy group; $Y_3$ and $Y_4$ each represent a substituted or unsubstituted alkyl group, aryl group, or heterocyclic group; $Y_3$ and $Y_4$ are different from each other; and $Z_1$, $Z_2$, $Z_3$, $Z_4$, $R_1$, $R_2$, $R_3$, $R_4$, a, d, b, and c are the same as the above.

An amino compound for an organic light-emitting device of the present invention is represented by general formula [5]:

[Chemical formula 5]

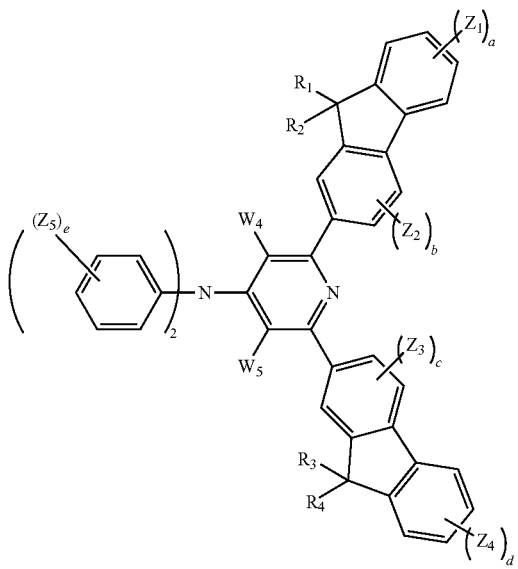

[5]

wherein $W_4$ and $W_5$ each represent a group selected from the group consisting of a hydrogen atom, a deuterium atom, a halogen atom, and a substituted or unsubstituted alkyl group; carbon atoms consisting of the two phenyl groups substituted with $Z_5$ are optionally substituted with nitrogen atoms; and $Z_5$, e, $Z_1$, $Z_2$, $Z_3$, $Z_4$, $R_1$, $R_2$, $R_3$, $R_4$, a, d, b, and c are the same as the above.

An organic light-emitting device according to the present invention includes a pair of electrodes composed of an anode and a cathode and an organic compound layer sandwiched between the pair of electrodes, wherein the organic compound layer contains the amino compound for an organic light-emitting device represented by any one of the above general formulae.

In the organic light-emitting device according to the present invention, the organic compound layer is a hole injection layer of a hole-transporting layer.

In the organic light-emitting device according to the present invention, the organic compound layer is a luminescent layer.

The present invention also provides an organic light-emitting device wherein the luminescent layer includes at least a host and a guest and the host is made of the amino compound for an organic light-emitting device.

A description will now be made of specific examples of $X_1$, which is a substituted or unsubstituted aromatic ring, fused polycyclic ring, or heterocyclic ring in general formula [1], and specific examples of the substituents in general formulae [1] to [5].

Examples of $X_1$, which is a substituted or unsubstituted aromatic ring, fused polycyclic ring, or heterocyclic ring, include, but are not limited to, a substituted or unsubstituted benzene ring, biphenyl ring, naphthalene ring, phenanthrene ring, anthracene ring, tetracene ring, benzanthracene ring, chrysene ring, pyrene ring, perylene ring, triphenylene ring, thiophene ring, pyridine ring, pyrazine ring, pyrazole ring, pyrrole ring, triazine ring, carbazole ring, benzimidazole ring, benzothiazole ring, quinoline ring, quinoxaline ring, and isoquinoline ring.

Examples of the substituted or unsubstituted alkyl groups include, but are not limited to, a methyl group, an ethyl group, a n-propyl group, a n-butyl group, a n-pentyl group, a n-hexyl group, an isopropyl group, an isobutyl group, a sec-butyl group, a tert-butyl group, an isopentyl group, a fluoromethyl group, a difluoromethyl group, a trifluoromethyl group, a 2-fluoroethyl group, a perfluoroethyl group, a 3-fluoropropyl group, a perfluoropropyl group, a 4-fluorobutyl group, a perfluorobutyl group, a 5-fluoropentyl group, a 6-fluorohexyl group, a chloromethyl group, a trichloromethyl group, a 2-chloroethyl group, a 2,2,2-trichloroethyl group, a 4-chlorobutyl group, a 5-chloropentyl group, a 6-chlorohexyl group, a bromomethyl group, a 2-bromoethyl group, an iodomethyl group, a 2-iodoethyl group, a hydroxymethyl group, a hydroxyethyl group, a cyclopropyl group, a cyclobutyl group, a cyclopentyl group, a cyclohexyl group, a cyclopentylmethyl group, a cyclohexylmethyl group, a cyclohexylethyl group, a 4-fluorocyclohexyl group, a norbornyl group, and an adamantyl group.

Examples of the substituted or unsubstituted aryl groups include, but are not limited to, a phenyl group, a 4-methylphenyl group, a 4-methoxyphenyl group, a 4-ethylphenyl group, a 4-fluorophenyl group, trifluorophenyl groups, a 3,5-dimethylphenyl group, a 2,6-diethylphenyl group, a mesityl group, a 4-tert-butylphenyl group, a ditolylaminophenyl group, a biphenyl group, a terphenyl group, a naphthyl group, an acenaphthylenyl group, an anthryl group, a phenanthryl group, a pyrenyl group, an acephenanthrylenyl group, a chrysenyl group, a dibenzochrysenyl group, a benzanthryl group, a dibenzanthryl group, a naphthacenyl group, a fluorenyl group, a triphenylenyl group, and a perylenyl group.

Examples of the substituted or unsubstituted heterocyclic groups include, but are not limited to, a pyrrolyl group, a pyridyl group, a bipyridyl group, a methylpyridyl group, a pyrimidinyl group, a pyrazinyl group, a pyridazinyl group, a terpyrrolyl group, a thienyl group, a terthienyl group, a propylthienyl group, a benzothienyl group, a dibenzothienyl group, a quinolyl group, an isoquinolyl group, a quinoxalinyl group, a naphthyridinyl group, a quinazolinyl group, a phenanthridinyl group, an indolizinyl group, a phenazinyl group, a carbazolyl group, an oxazolyl group, an oxadiazolyl group, a thiazolyl group, and a thiadiazolyl group.

Examples of the substituted or unsubstituted aralkyl groups include, but are not limited to, a benzyl group, a 2-phenylethyl group, a 2-phenylisopropyl group, a 1-naphtylmethyl group, a 2-naphthylmethyl group, a 2-(1-naphthyl)ethyl group, a 2-(2-naphthyl)ethyl group, a 9-anthrylmethyl group, a 2-(9-anthryl)ethyl group, a 2-fluorobenzyl group, a 3-fluorobenzyl group, a 4-fluorobenzyl group, a 2-chlorobenzyl group, a 3-chlorobenzyl group, a 4-chlorobenzyl group, a 2-bromobenzyl group, a 3-bromobenzyl group, and a 4-bromobenzyl group.

Examples of the substituted or unsubstituted alkenyl groups include, but are not limited to, a vinyl group, an allyl group (2-propenyl group), and a styryl group.

Examples of the substituted or unsubstituted alkynyl groups include, but are not limited to, an acetylenyl group, a phenylacetylenyl group, and a 1-propynyl group.

Examples of the substituted or unsubstituted alkoxy groups include, but are not limited to, alkyloxy groups and aralkyloxy groups having the above-described substituted or unsubstituted alkyl group or aralkyl group; and aryloxy groups having the above-described substituted or unsubstituted aryl group or heterocyclic group, such as a methoxy group, an ethoxy group, a propoxy group, a 2-ethyl-octyloxy group, a phenoxy group, a 4-tert-butylphenoxy group, a benzyloxy group, and a thienyloxy group.

Examples of the substituents which the above-described substituents may have include, but are not limited to, a deuterium atom; alkyl groups and aralkyl groups such as a methyl group, an ethyl group, a n-propyl group, a n-butyl group, a n-pentyl group, a n-hexyl group, a n-heptyl group, a n-octyl group, a n-decyl group, an isopropyl group, an isobutyl group, a sec-butyl group, a tert-butyl group, an isopentyl group, a neopentyl group, a tert-octyl group, a benzyl group, and a 2-phenylethyl group; alkoxy groups such as a methoxy group, an ethoxy group, a propoxy group, a 2-ethyl-octyloxy group, a phenoxy group, a 4-tert-butylphenoxy group, and a benzyloxy group; aryl groups such as a phenyl group, a 4-methylphenyl group, a 4-ethylphenyl group, a 3-chlorophenyl group, a 3,5-dimethylphenyl group, a triphenylamino group, a biphenyl group, a terphenyl group, a naphthyl group, an anthryl group, a phenanthryl group, and a pyrenyl group; heterocyclic groups such as a pyridyl group, a bipyridyl group, a methylpyridyl group, a thienyl group, a terthienyl group, a propylthienyl group, a furyl group, a quinolyl group, a carbazolyl group, and N-ethylcarbazolyl group; a halogen group; a hydroxyl group; a cyano group; and a nitro group.

The amino compounds represented by general formulae [1] to [5] can be used as a material for an organic light-emitting device.

The amino compounds represented by general formulae [1] to [5] can be used as at least one layer selected from a hole-transporting layer, a hole injection layer, and a luminescent layer to provide a device having a high luminous efficiency and a long lifetime.

When the amino compounds represented by general formulae [1] to [5] are used for a luminescent layer, the amino compounds can be used alone in the luminescent layer, or used as a dopant (guest) material or a host material of a fluorescent material or a phosphorescent material. As a result, a device having a high color purity, a high luminous efficiency, and a long lifetime can be produced.

The present invention will now be described in detail.

Specific examples of the compounds represented by general formulae [1] to [5] are shown below, but the present invention is not limited thereto.

[Chemical formula 6]

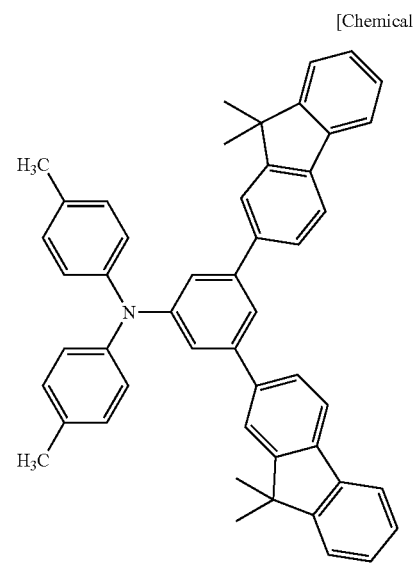

H-1

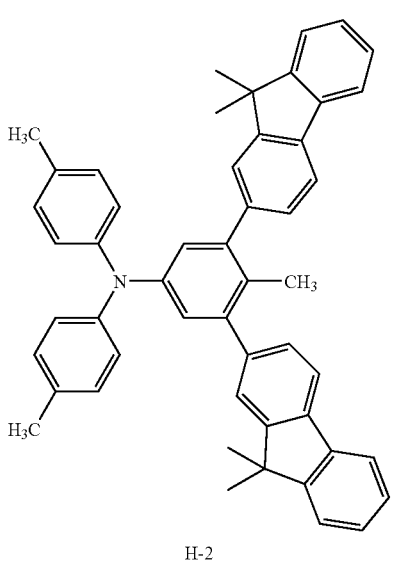

H-2

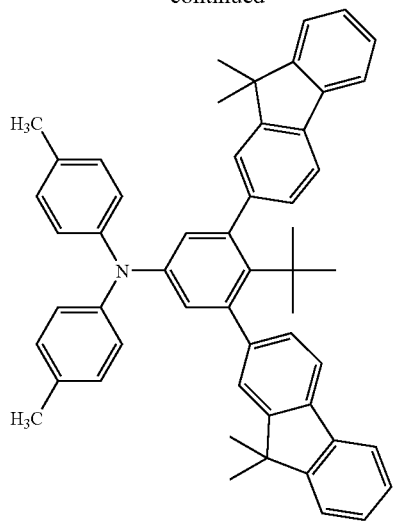

H-3

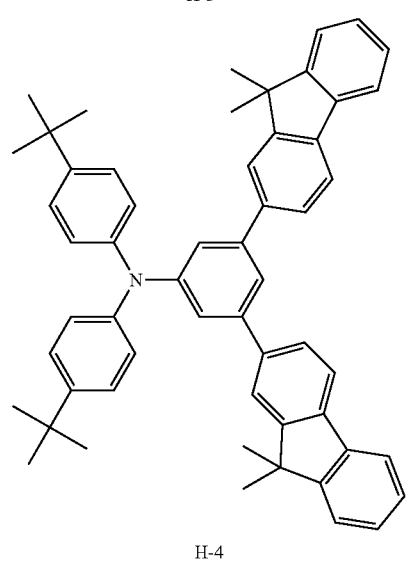

H-4

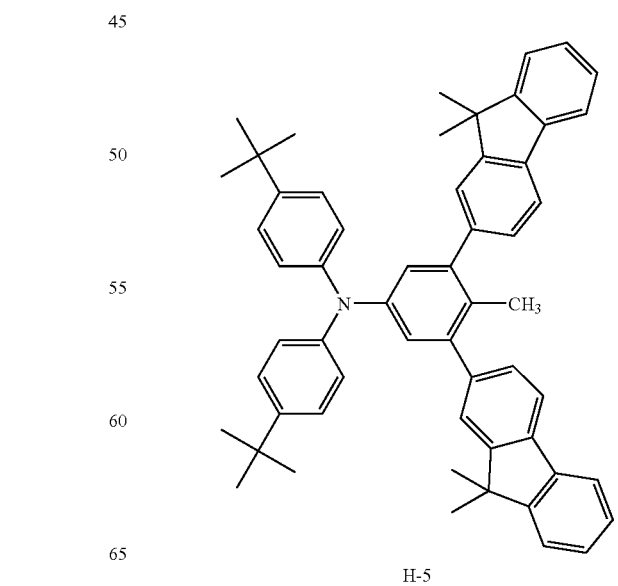

H-5

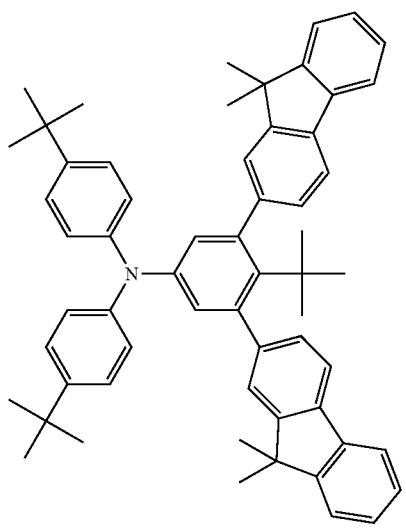
H-6
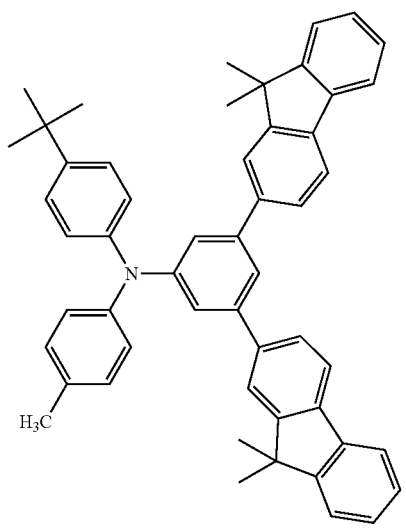
H-7
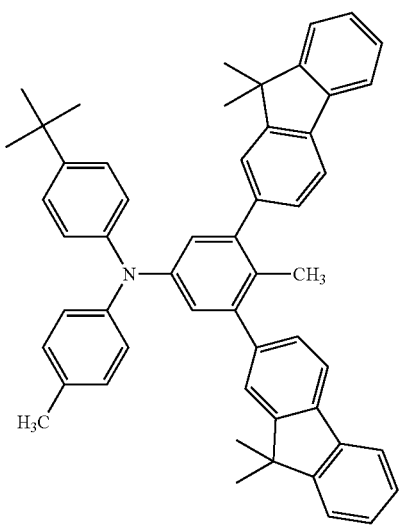
H-8
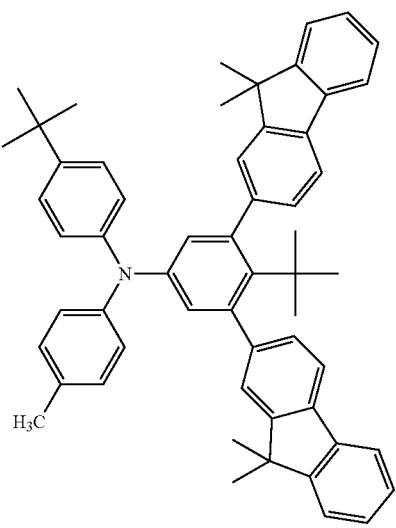
H-9
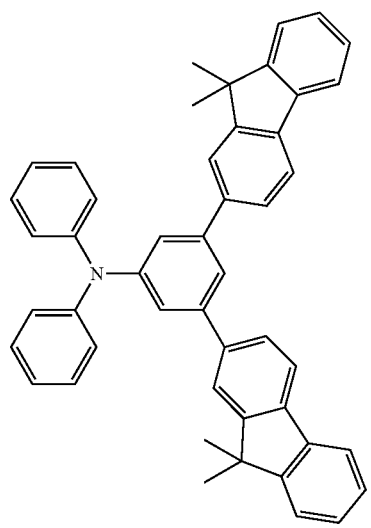
H-10
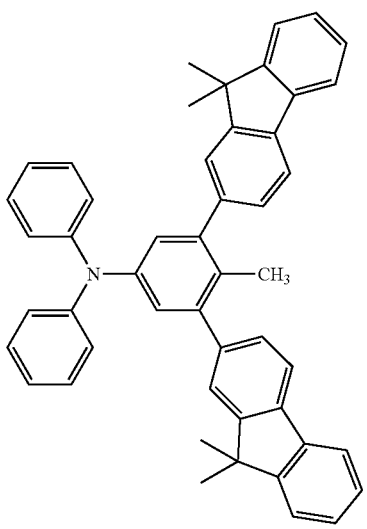
H-11

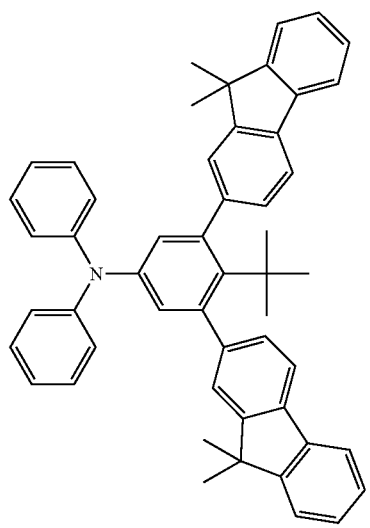
H-12
[Chemical formula 7]
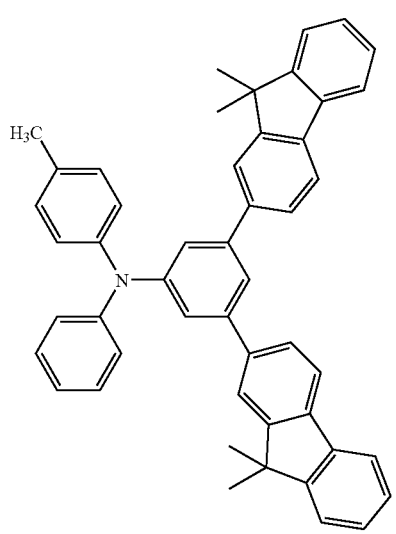
H-13
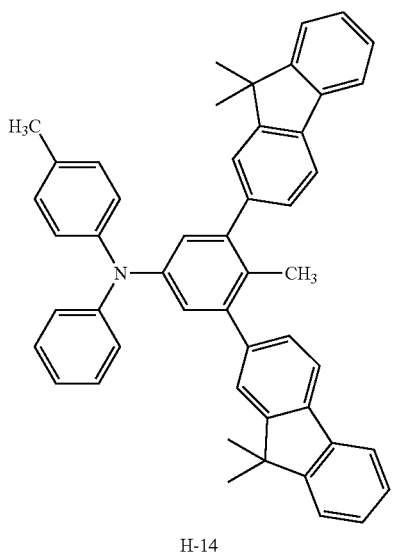
H-14
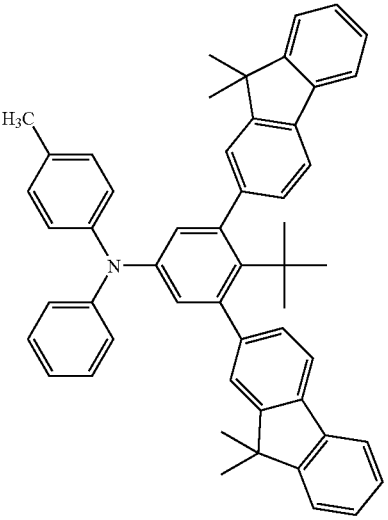
H-15
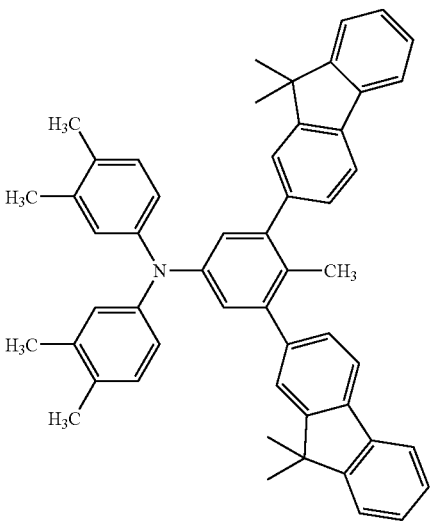
H-16
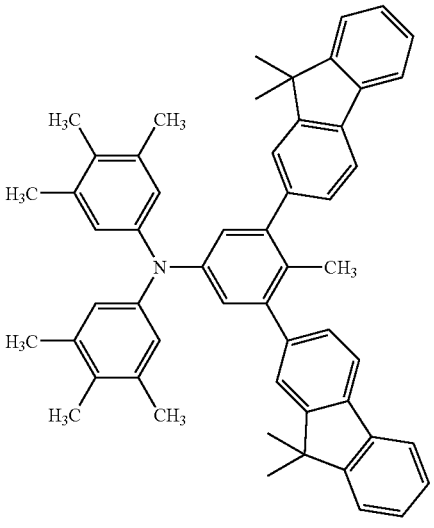
H-17

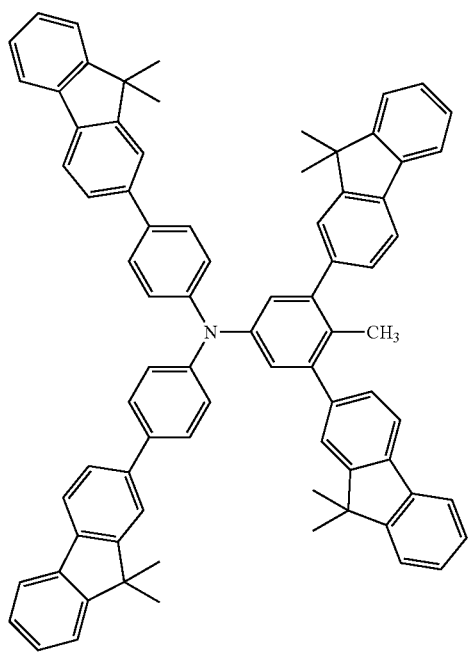
H-18
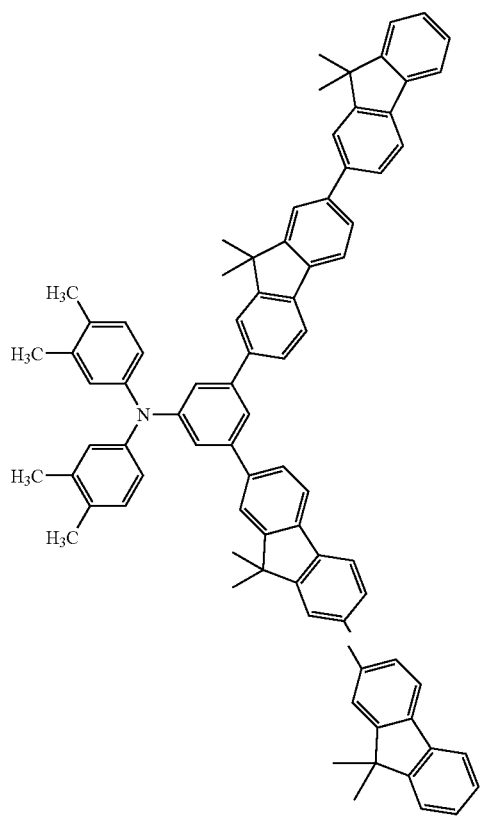
H-20
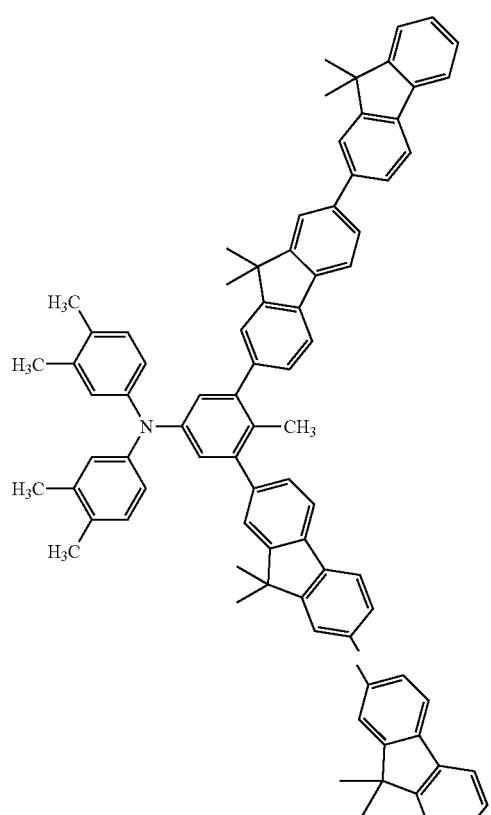
H-19
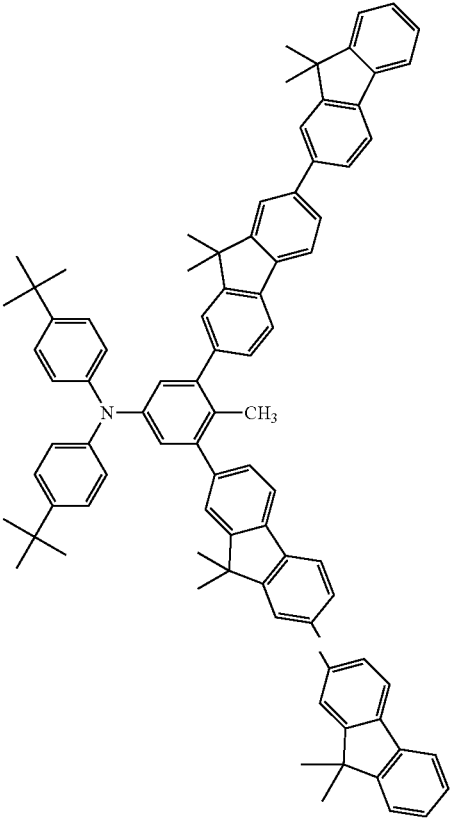
H-21

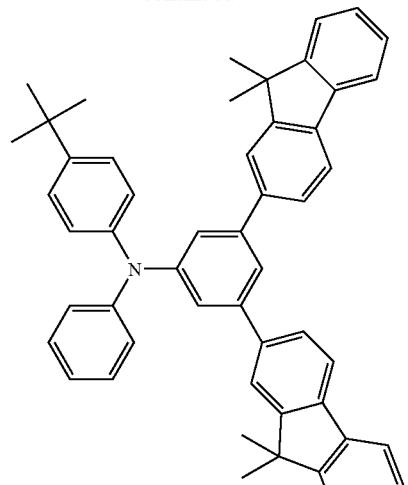
H-22
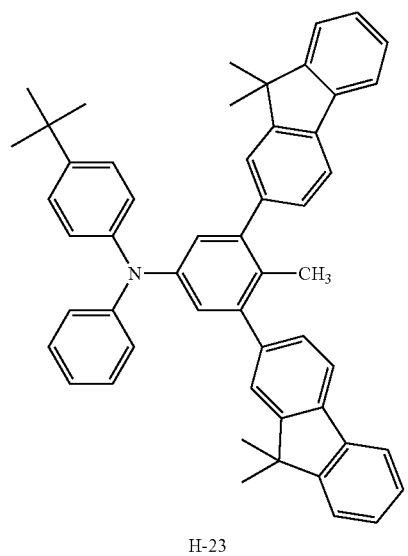
H-23
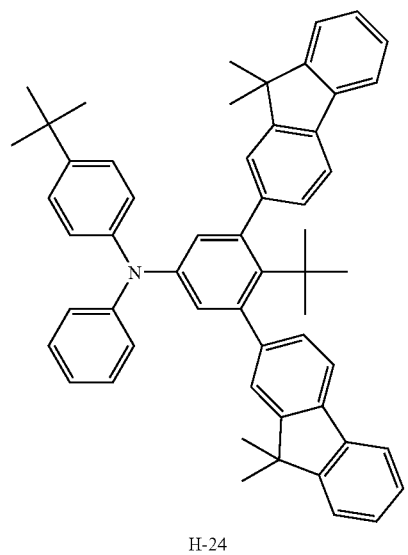
H-24
[Chemical formula 8]
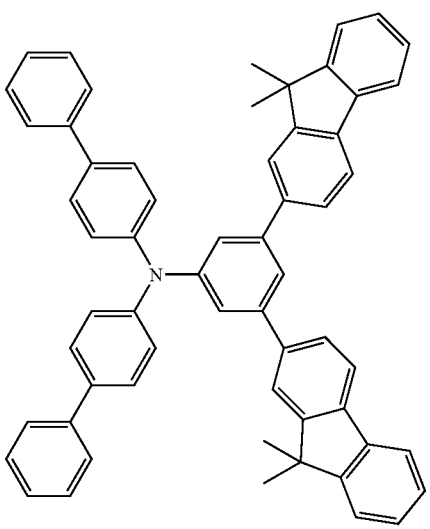
H-25
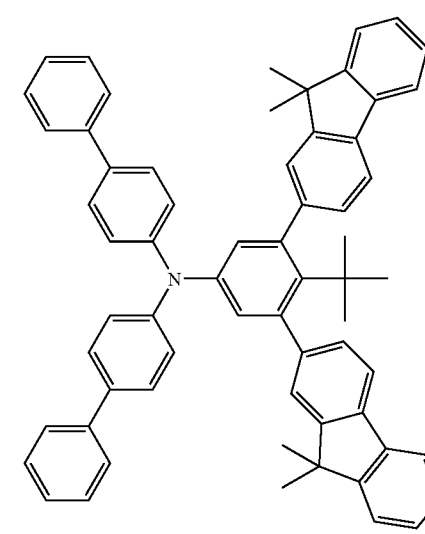
H-26
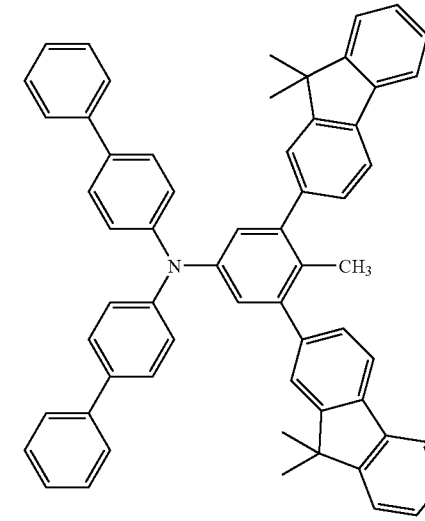
H-27

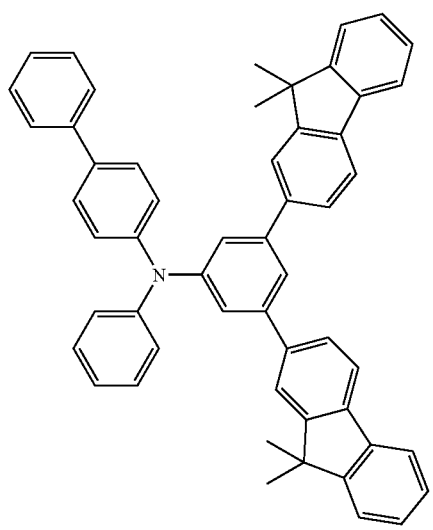
H-28
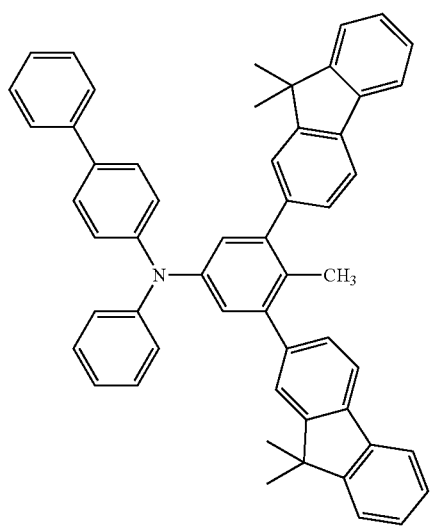
H-29
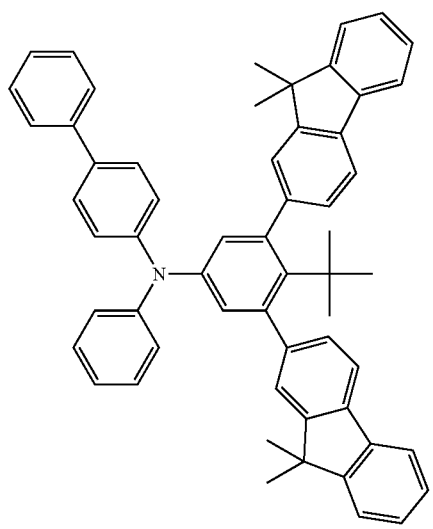
H-30
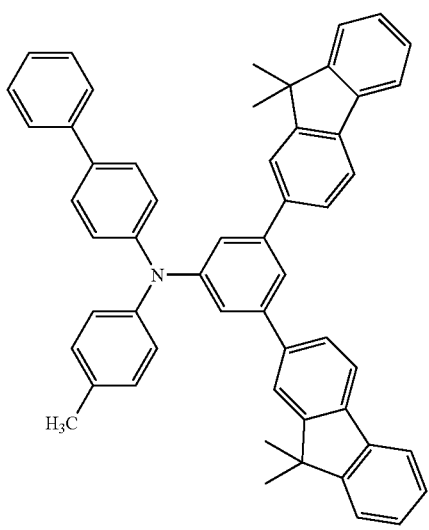
H-31
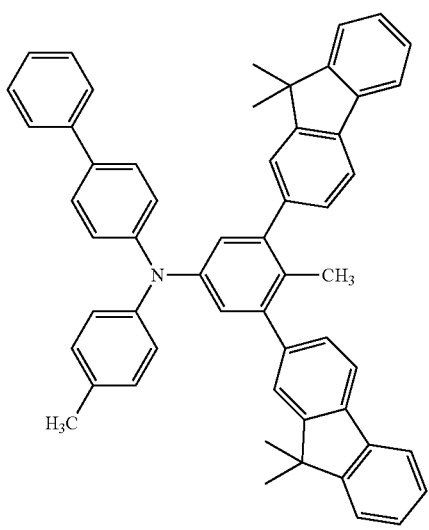
H-32
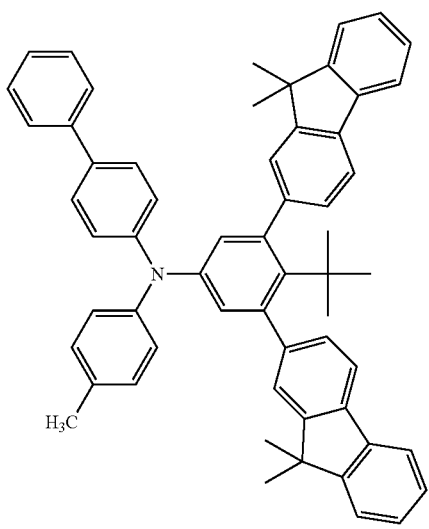
H-33

[Chemical formula 9]
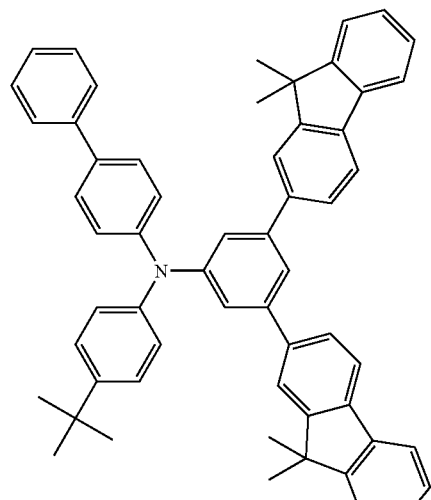
H-34
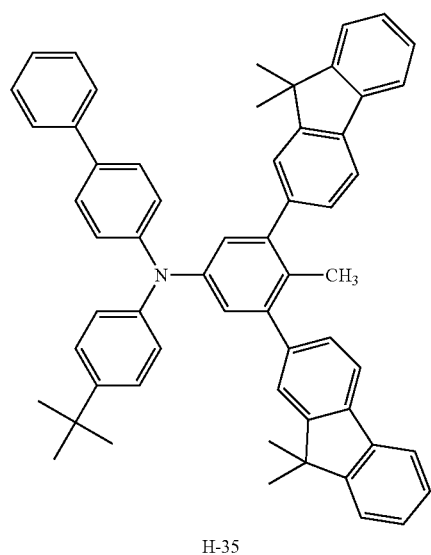
H-35
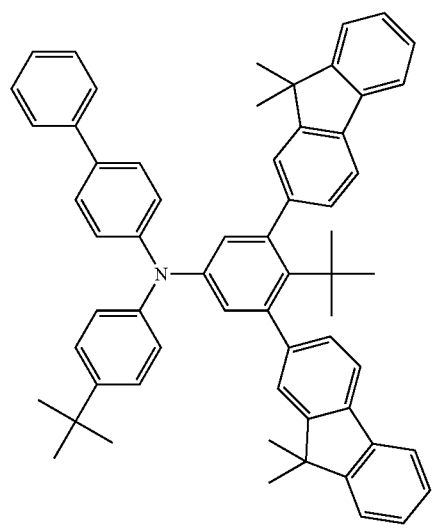
H-36
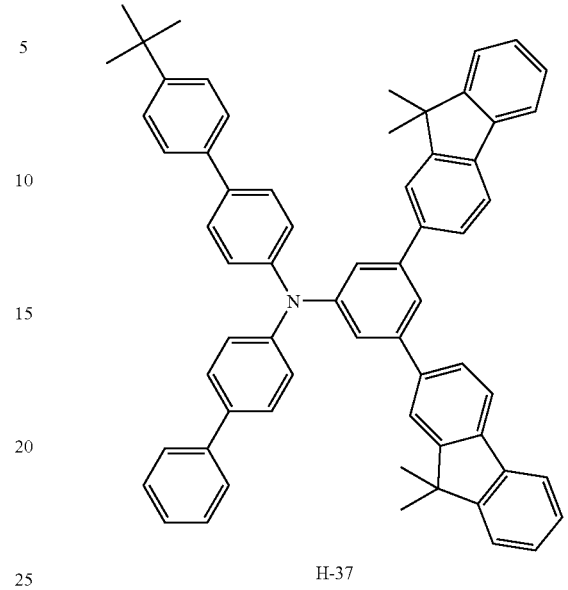
H-37
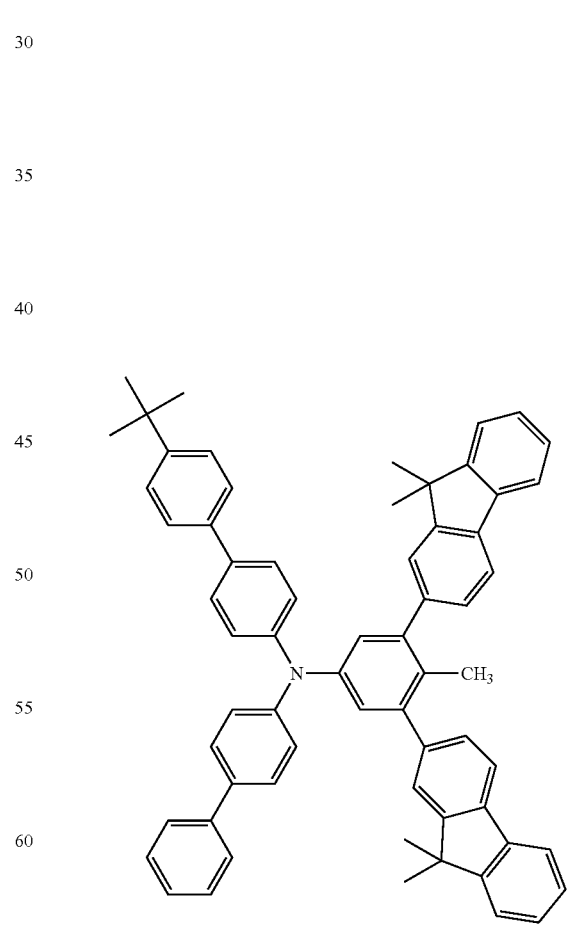
H-38

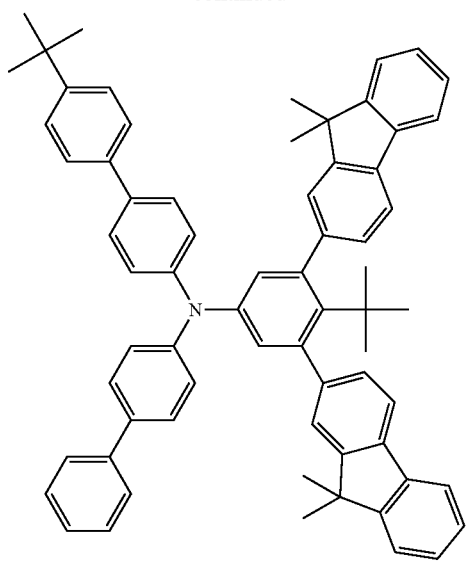
H-39
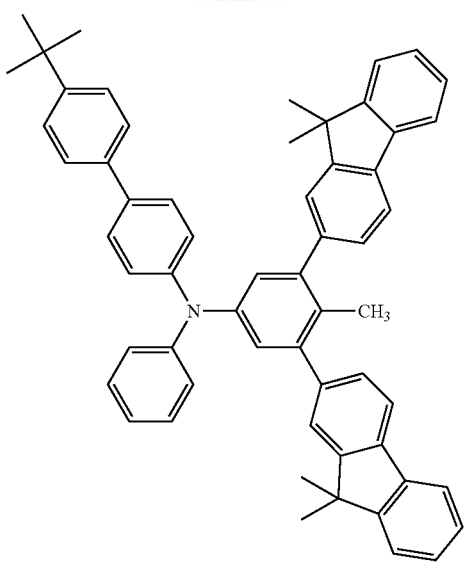
H-41
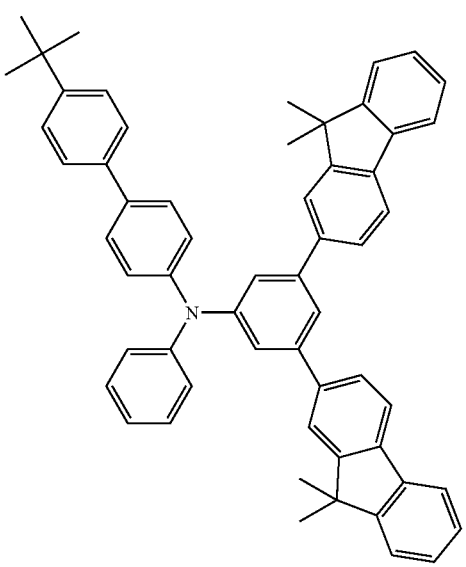
H-40
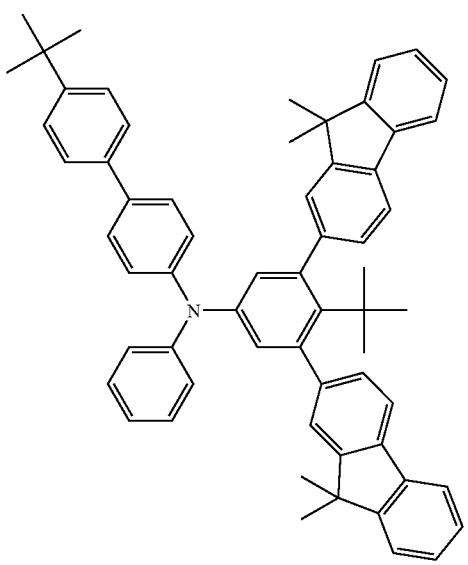
H-42

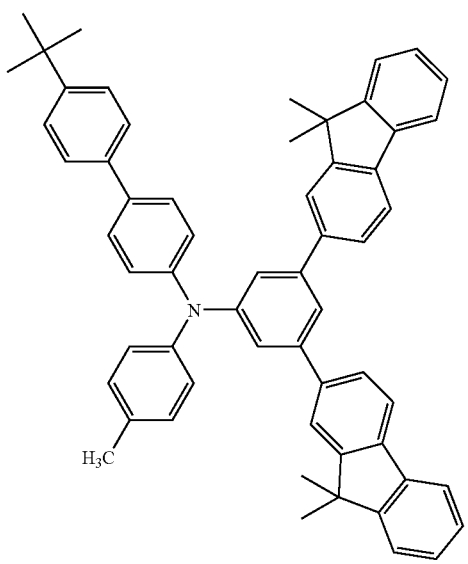
H-43
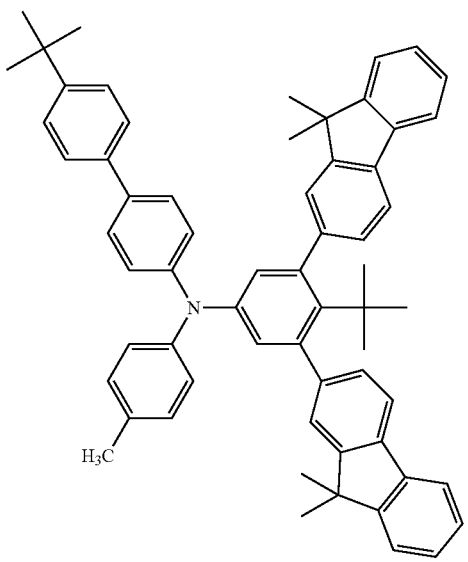
H-45
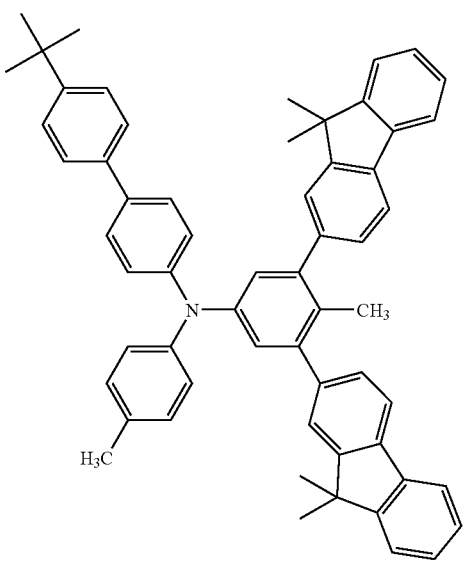
H-44
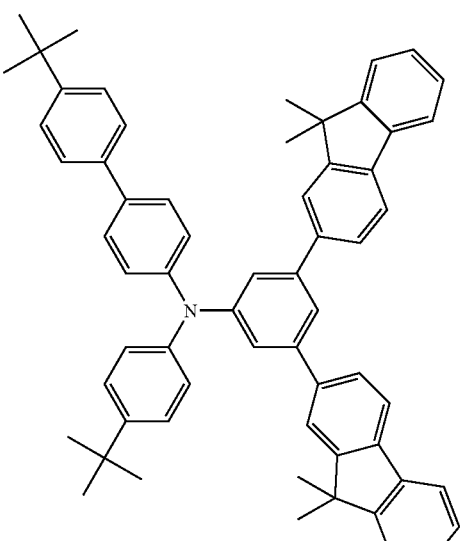
H-46

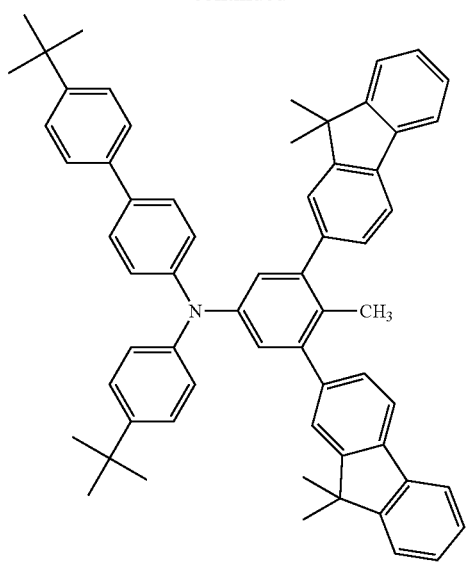
H-47
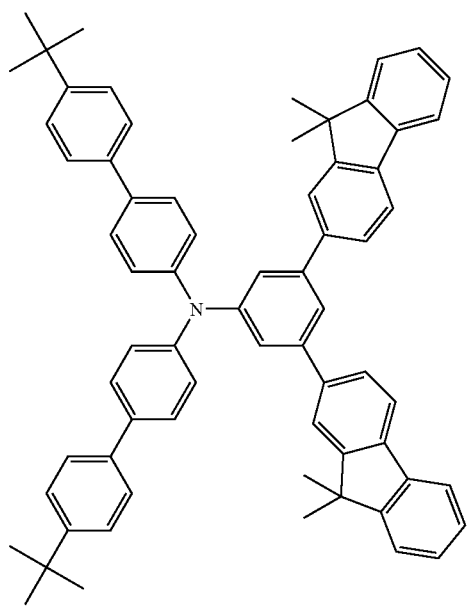
H-49
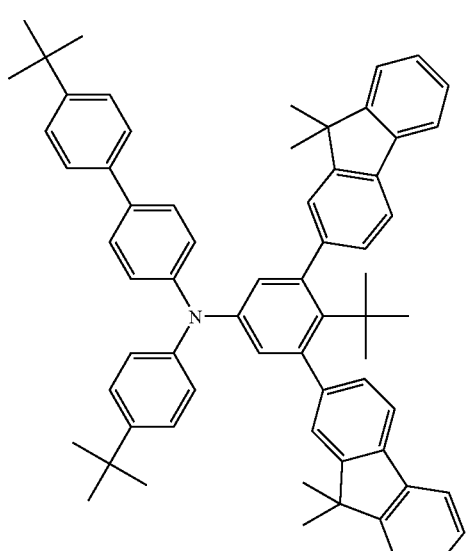
H-48
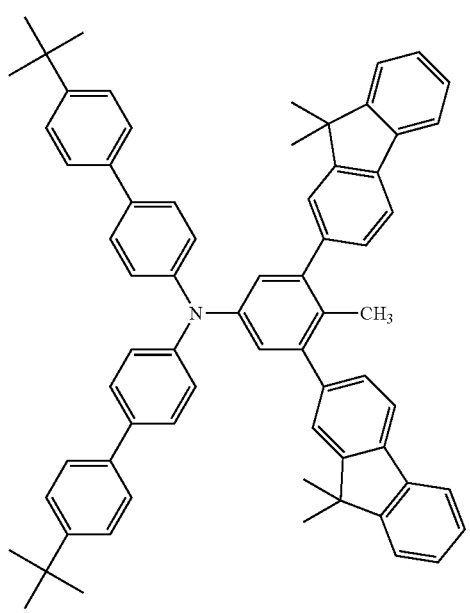
H-50

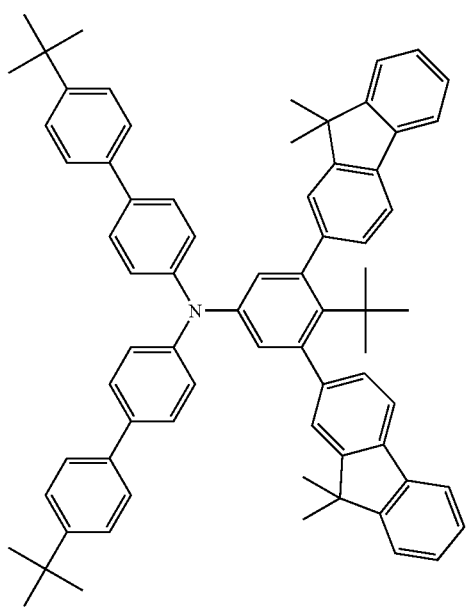
H-51
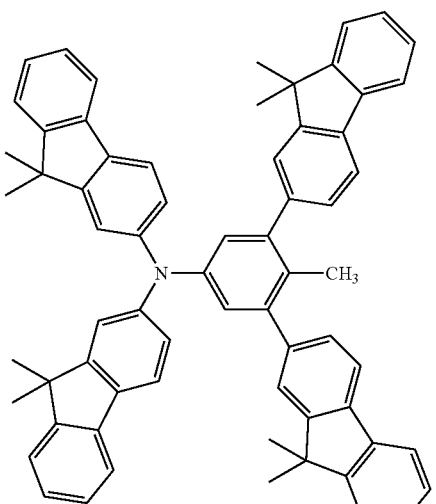
H-53
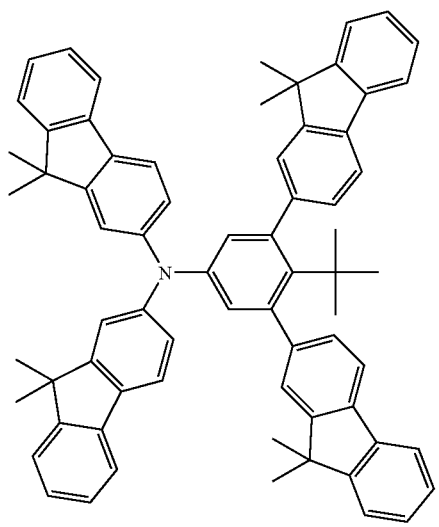
H-54
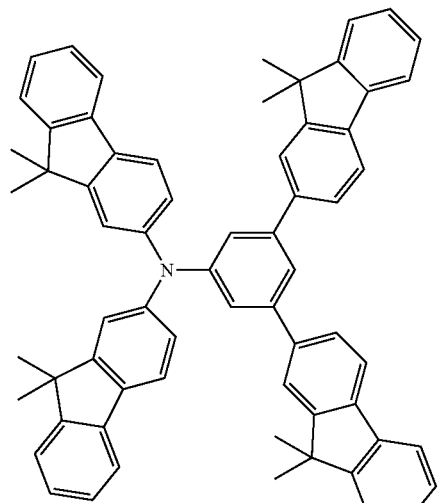
H-52
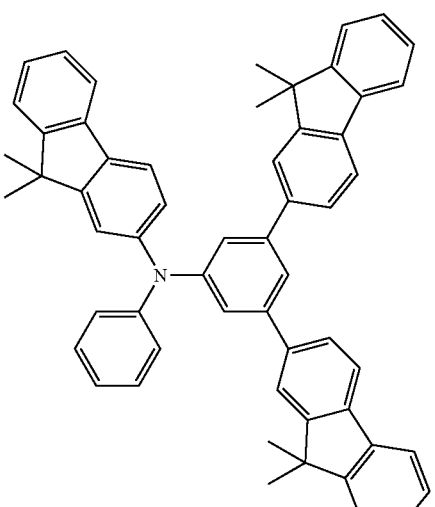
H-55

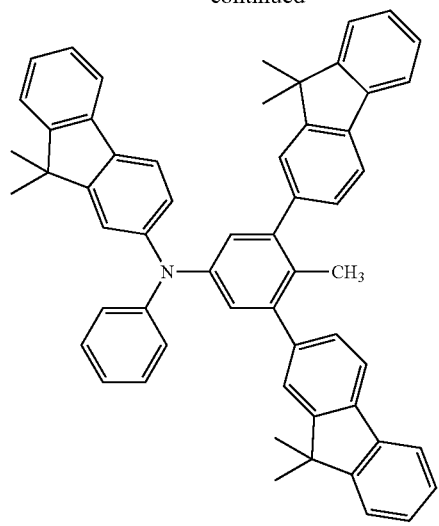
H-56
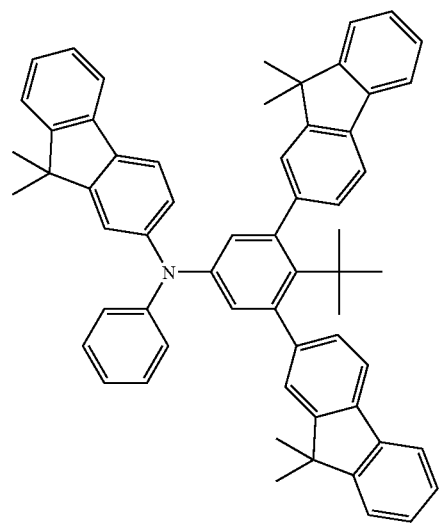
H-57
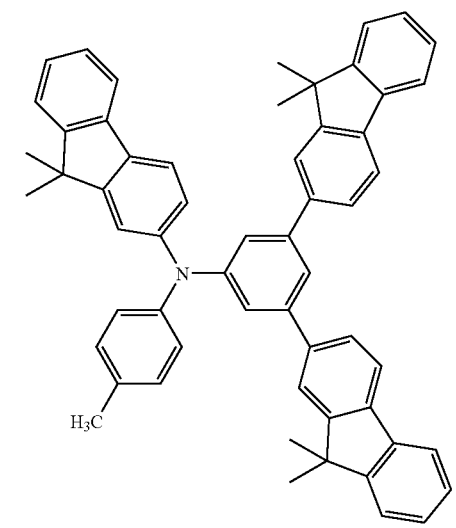
H-58
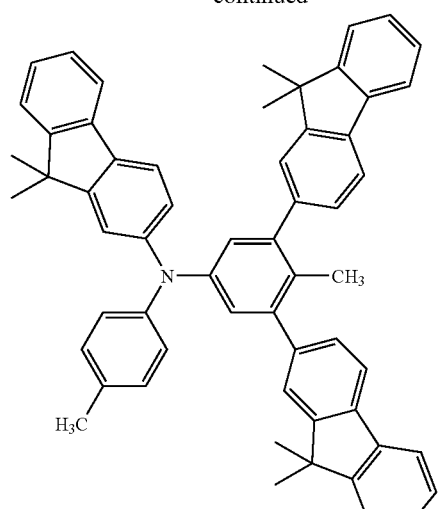
H-59
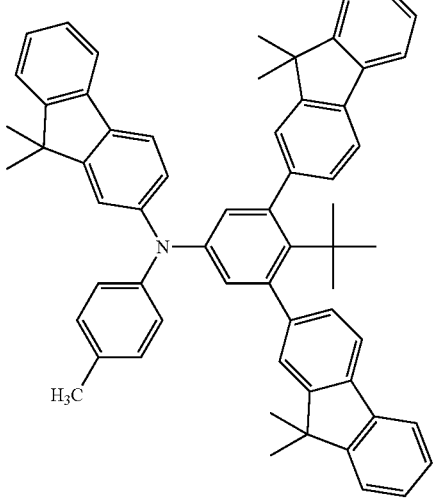
H-60
[Chemical formula 11]
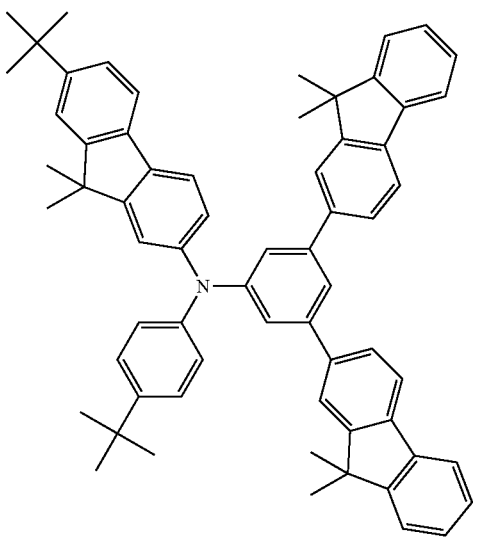
H-61

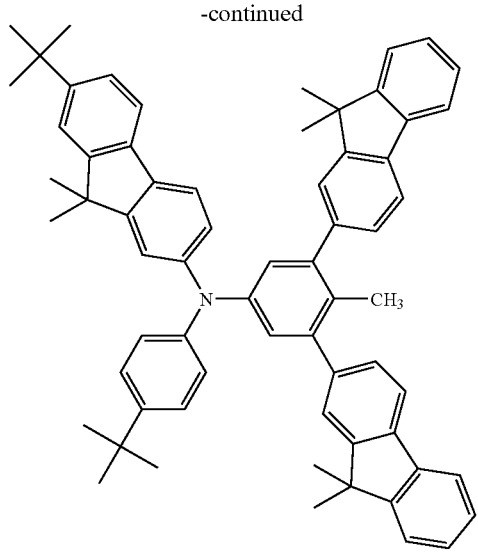
H-62
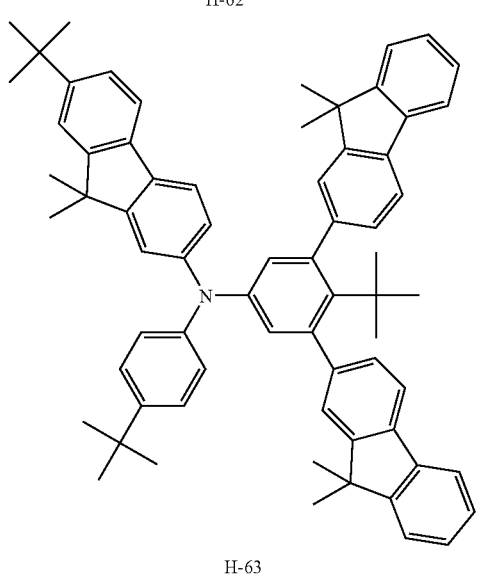
H-63
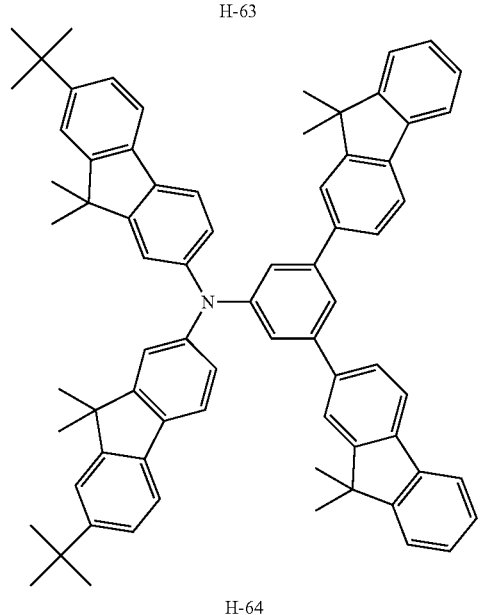
H-64
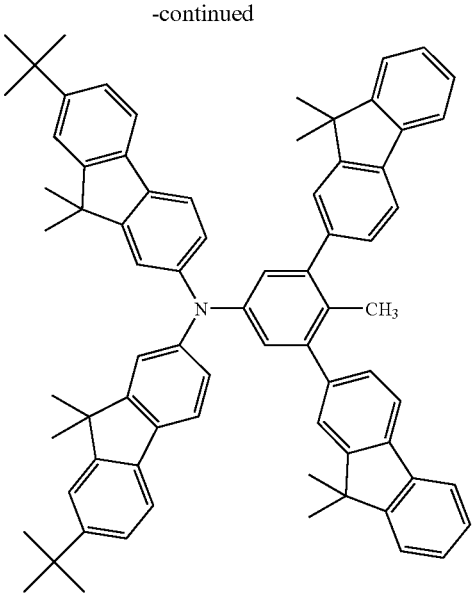
H-65
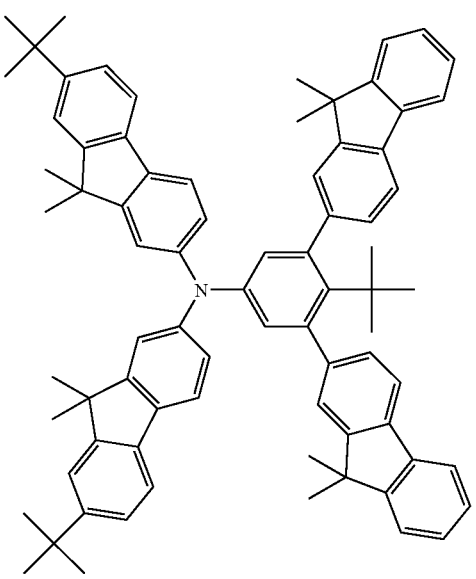
H-66

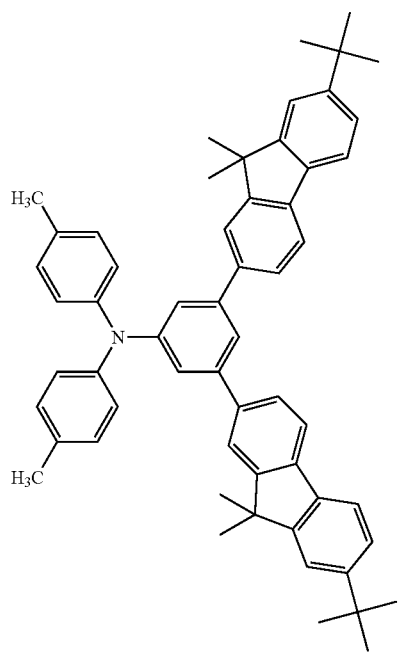
H-67
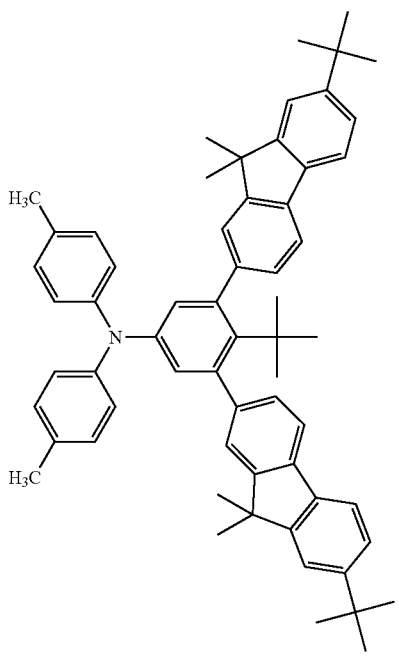
H-69
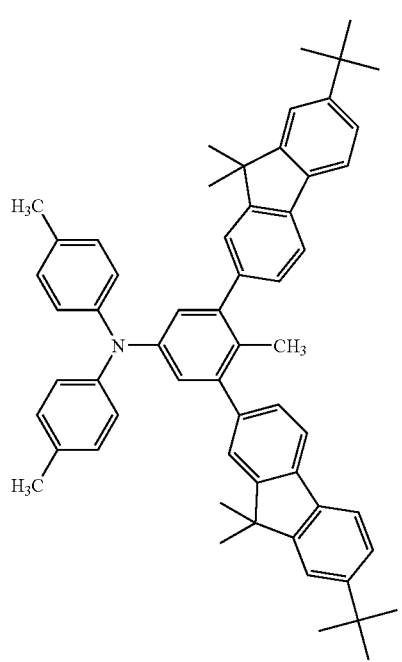
H-68
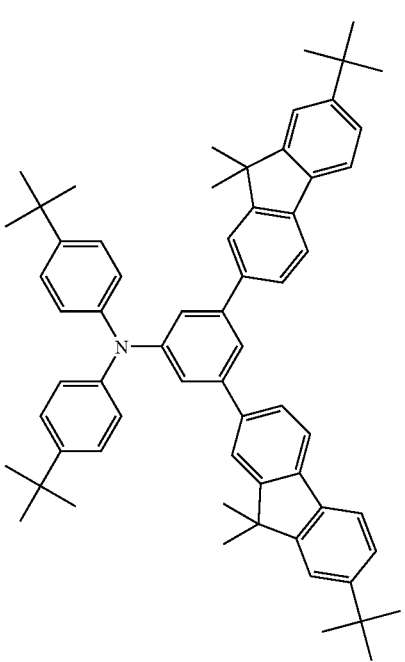
H-70

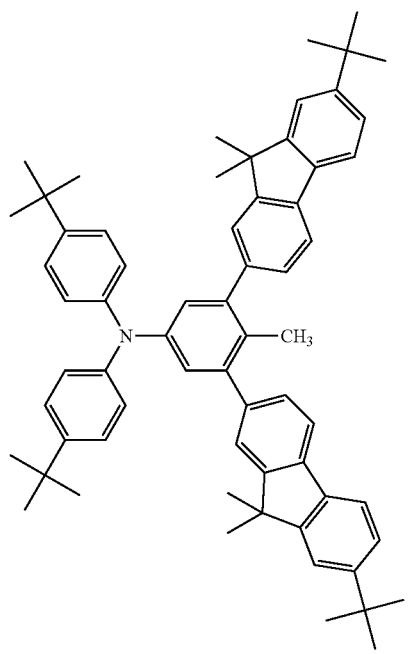
H-71
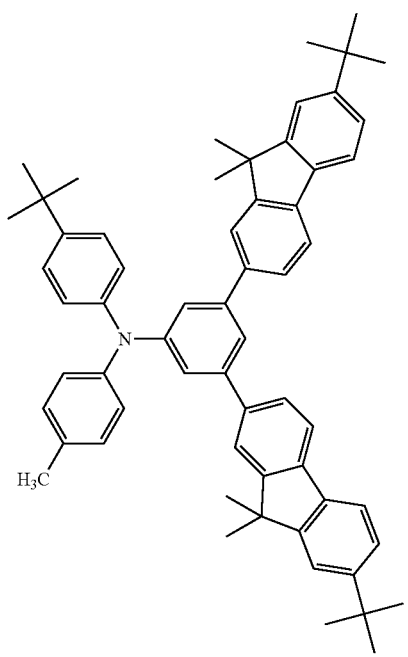
H-73
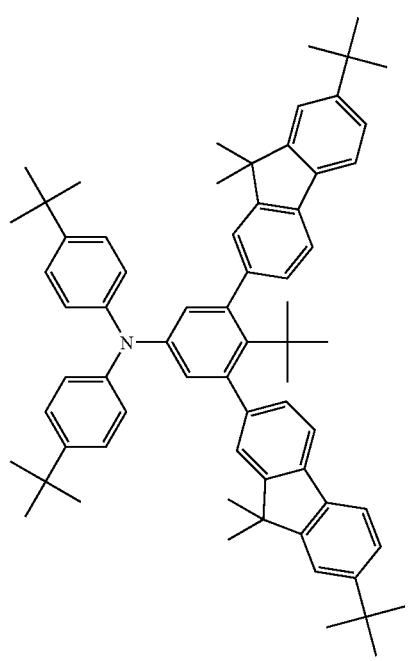
H-72
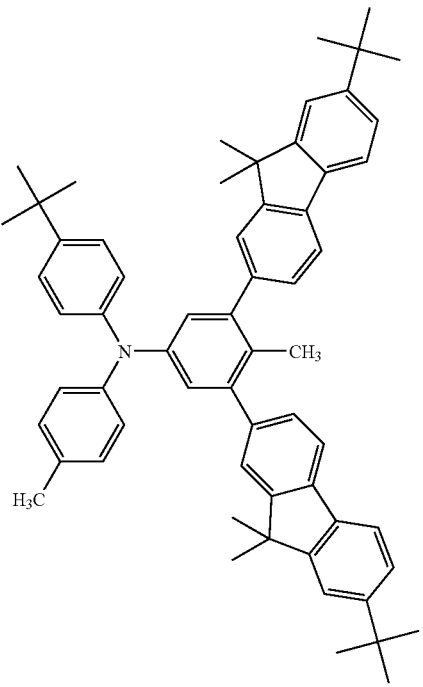
H-74

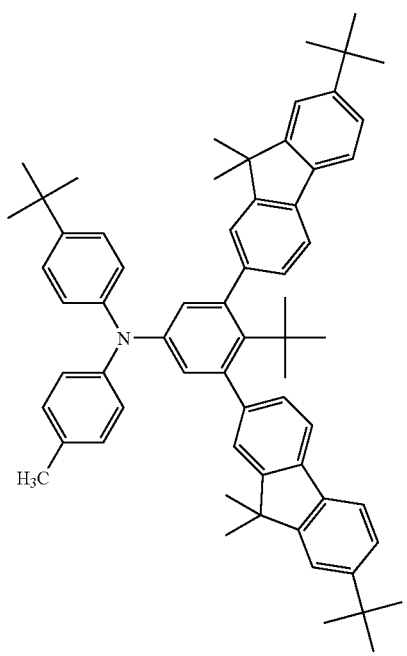
H-75
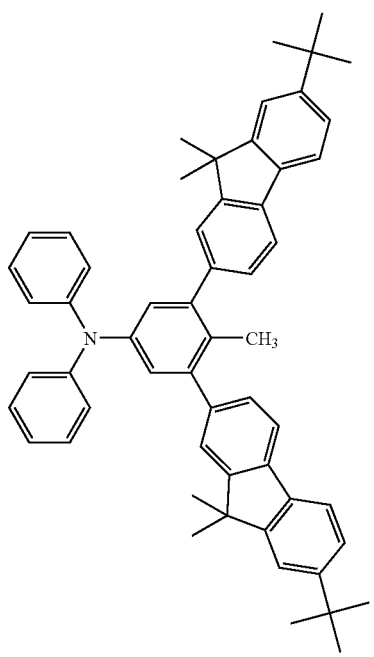
H-77
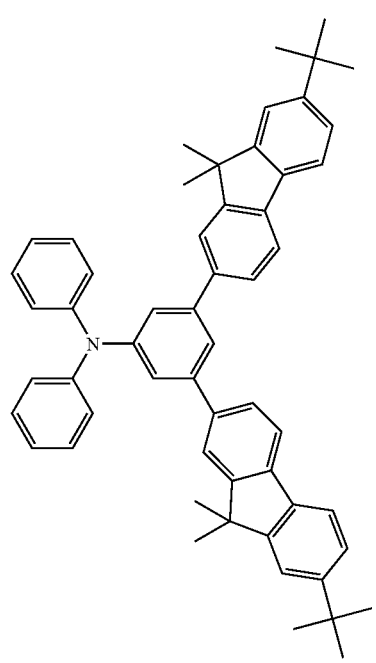
H-76
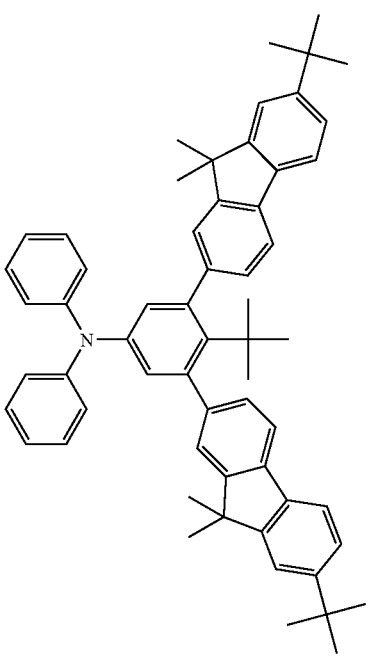
H-78

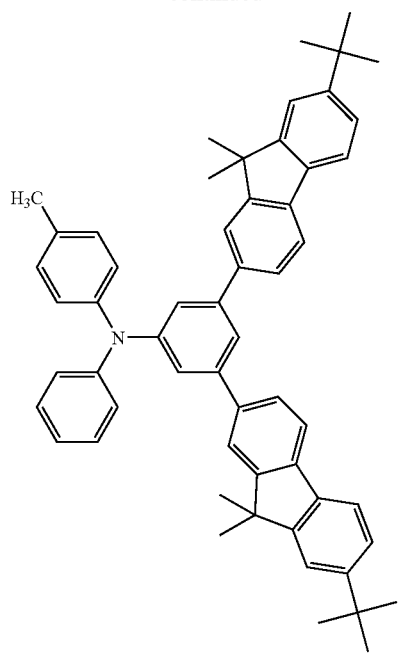
H-79
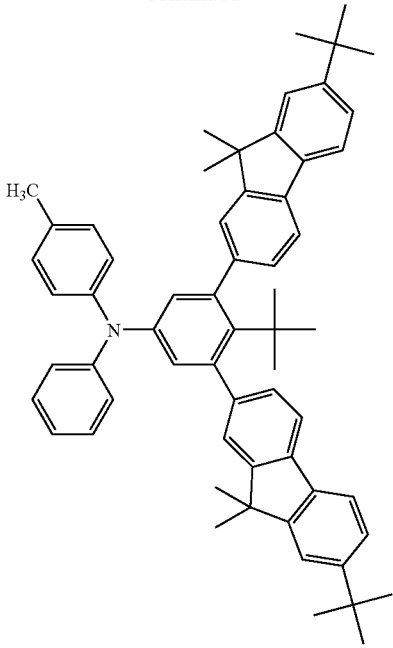
H-81
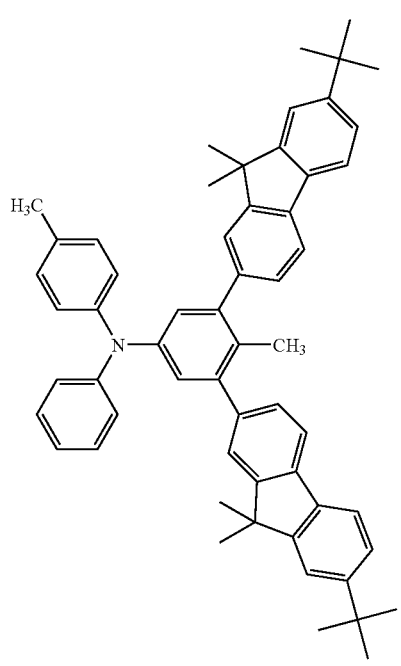
H-80
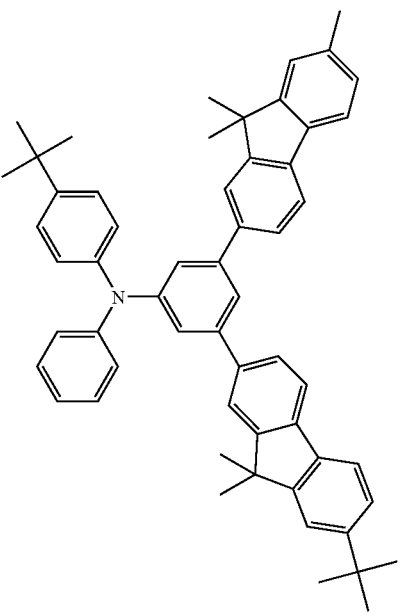
H-82

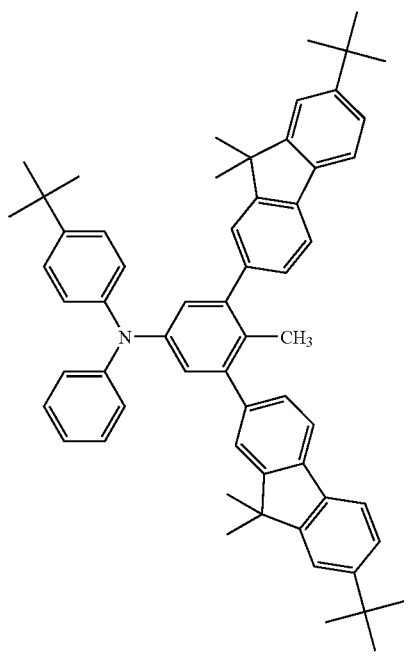
H-83
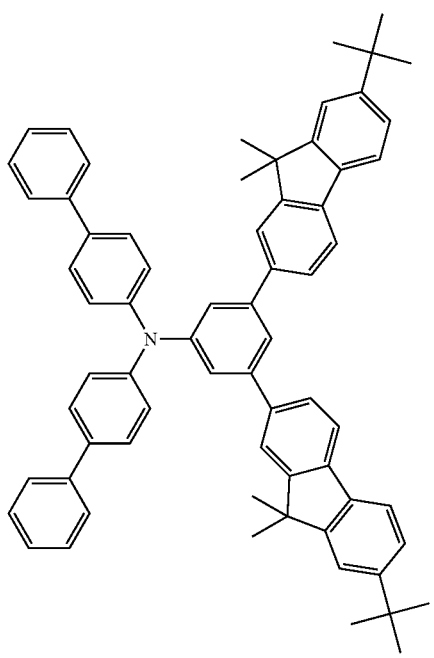
H-85
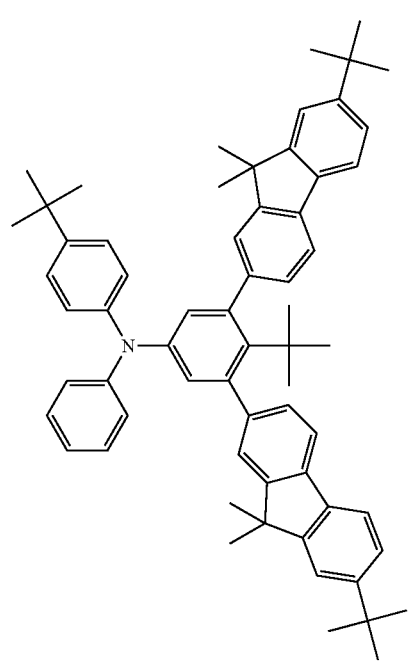
H-84
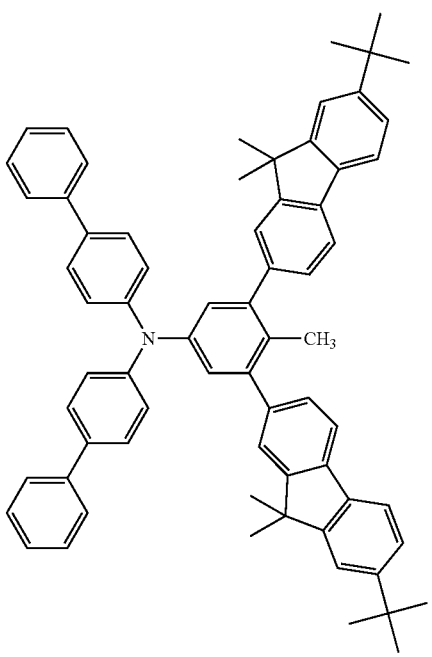
H-86

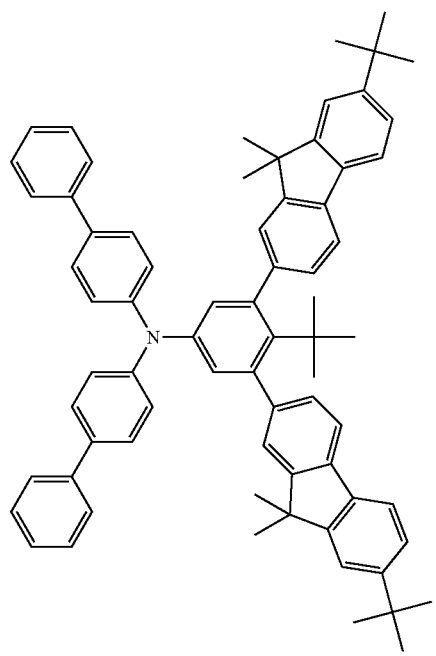
H-87
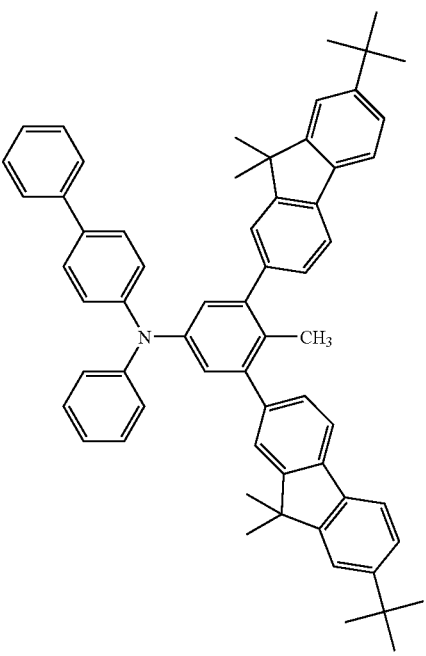
H-89
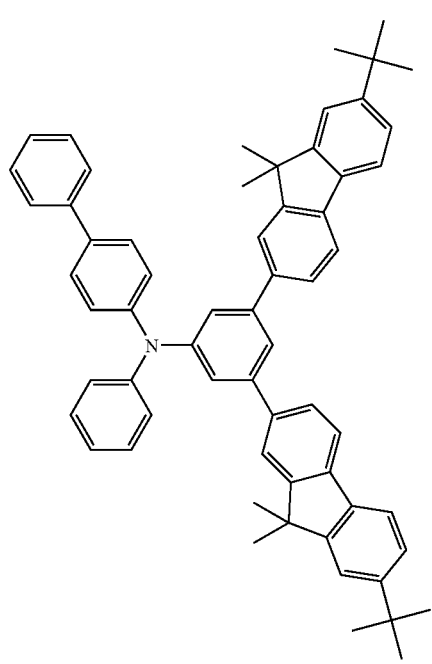
H-88
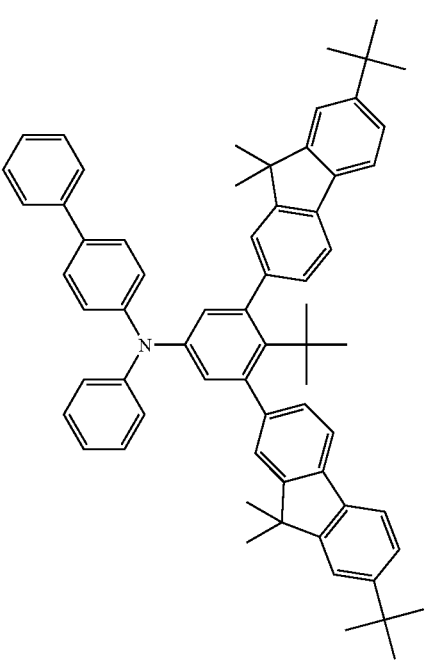
H-90

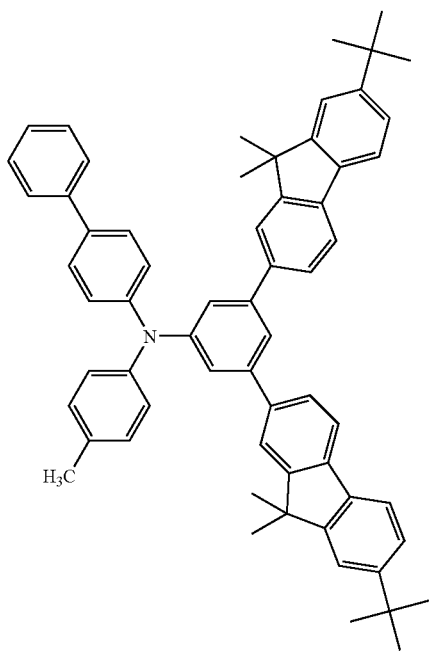
H-91
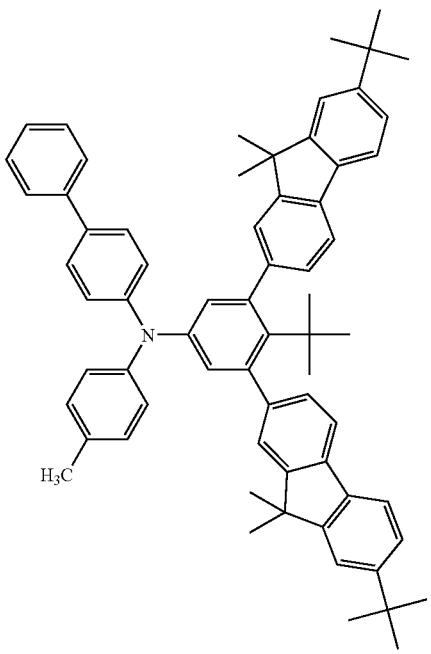
H-93
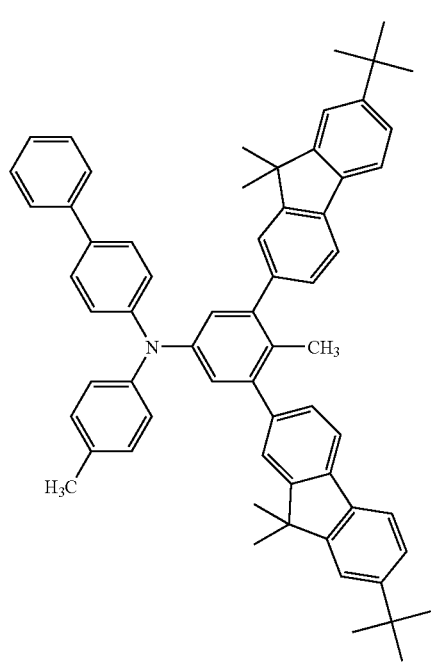
H-92
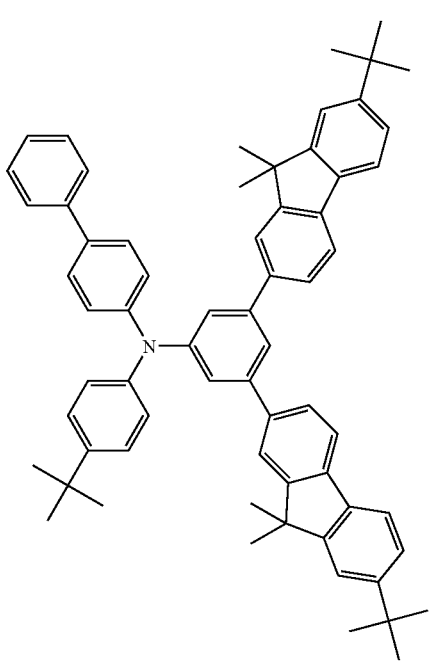
H-94

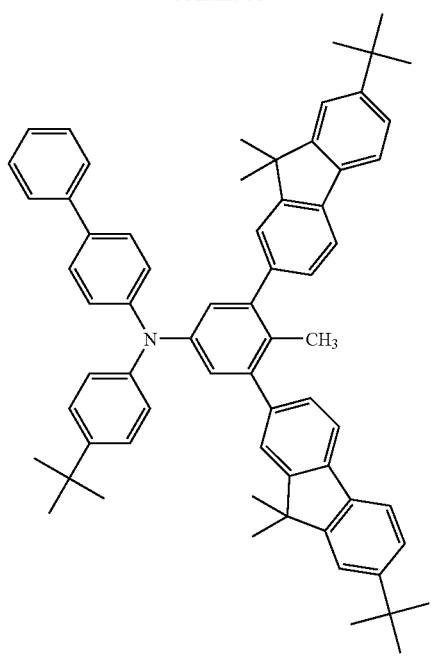
H-95
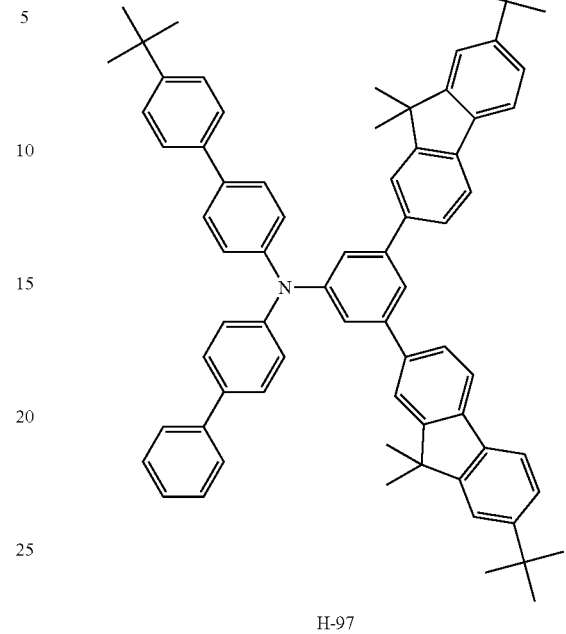
H-97
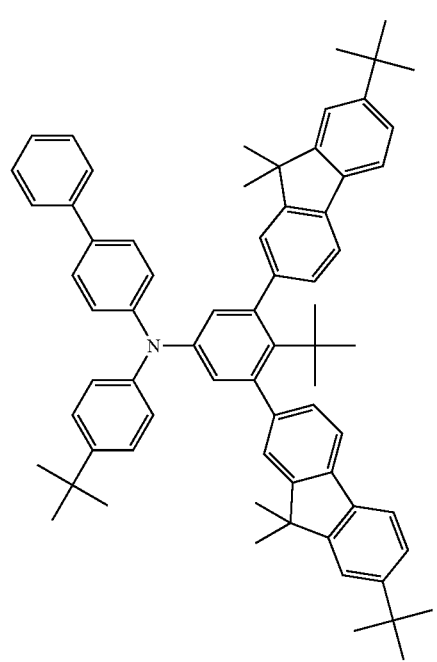
H-96
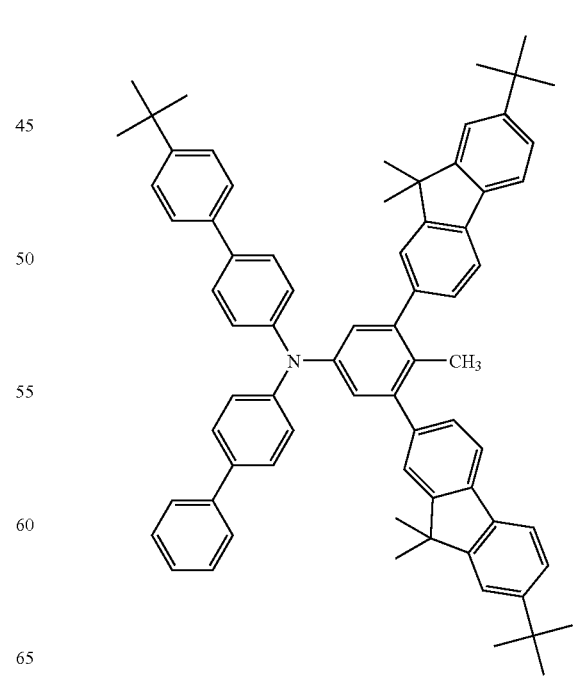
H-98

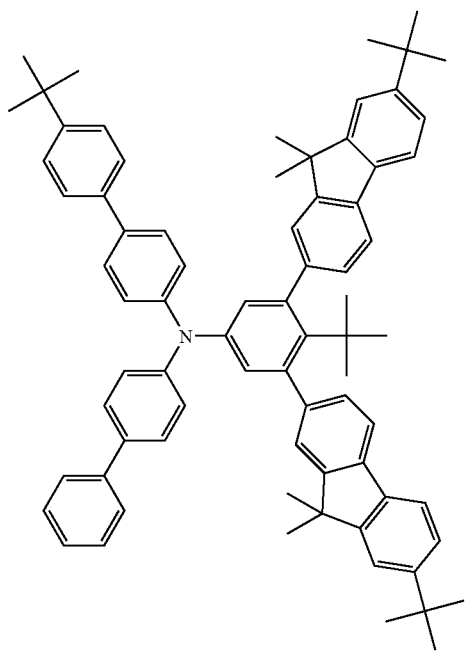
H-99
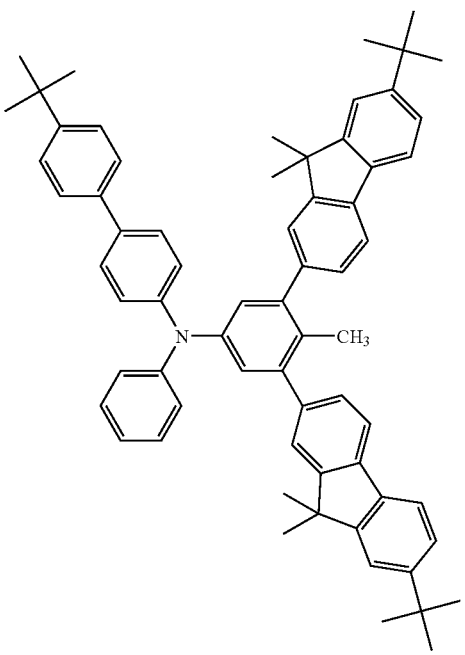
H-101
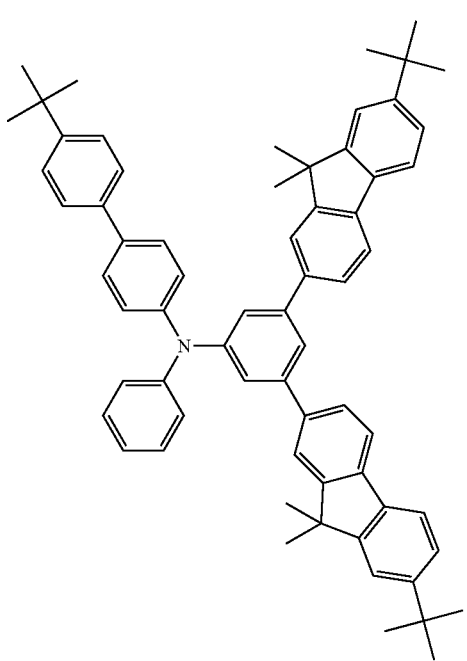
H-100
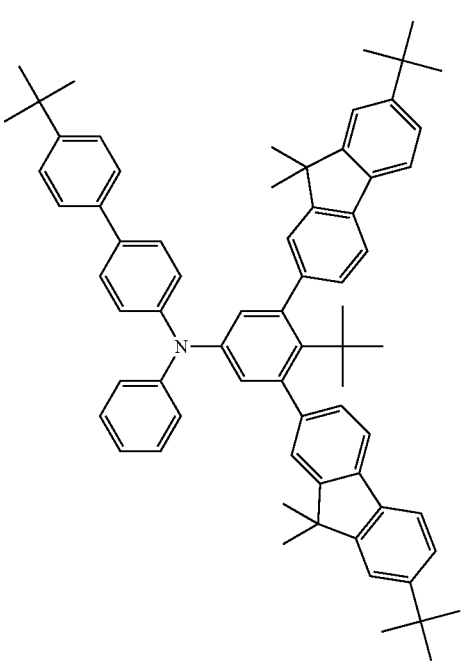
H-102

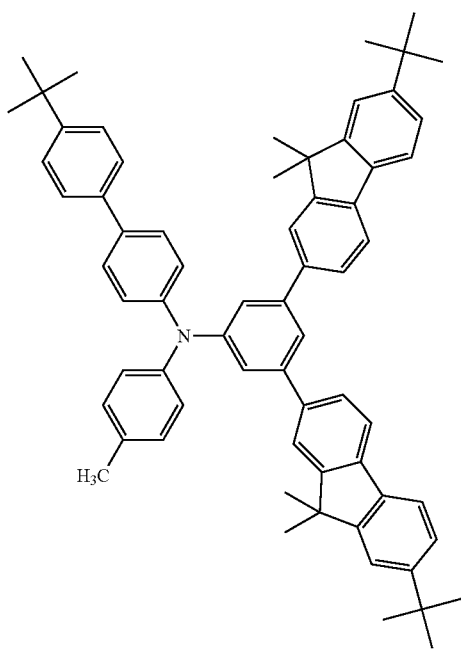
H-103
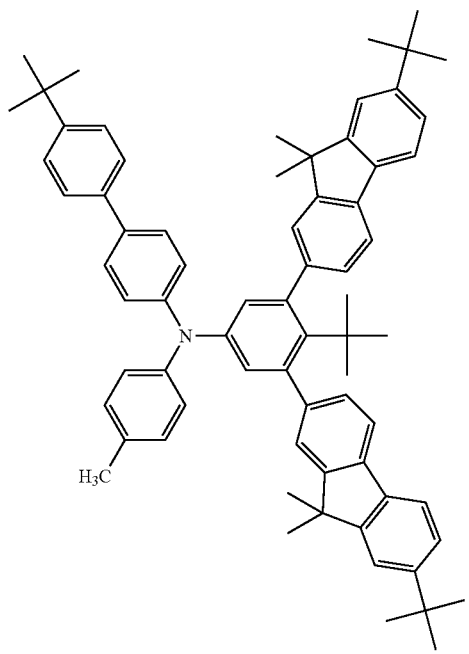
H-105
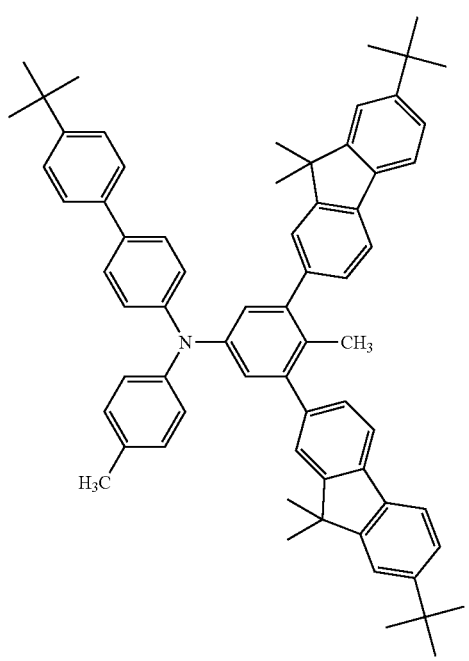
H-104
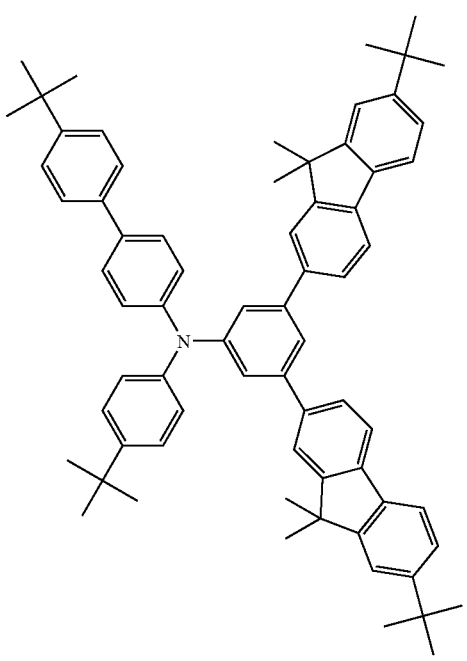
H-106

[Chemical formula 15]
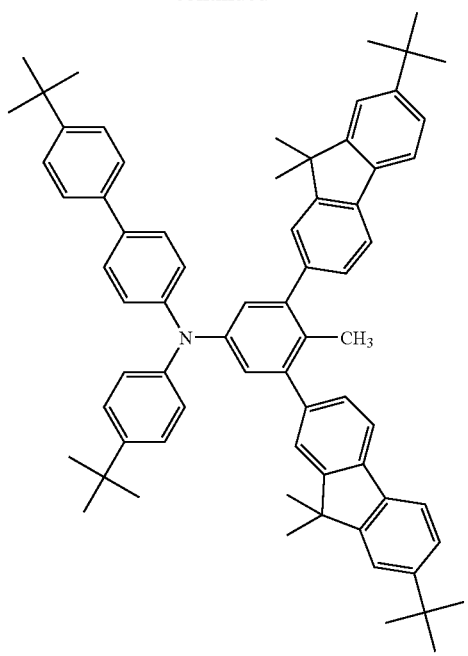
H-107
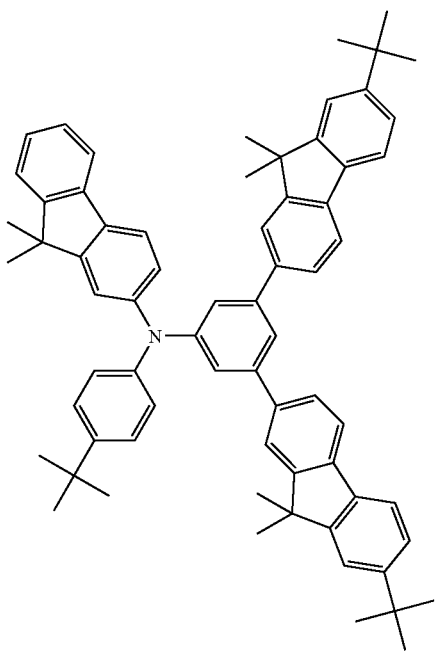
H-109
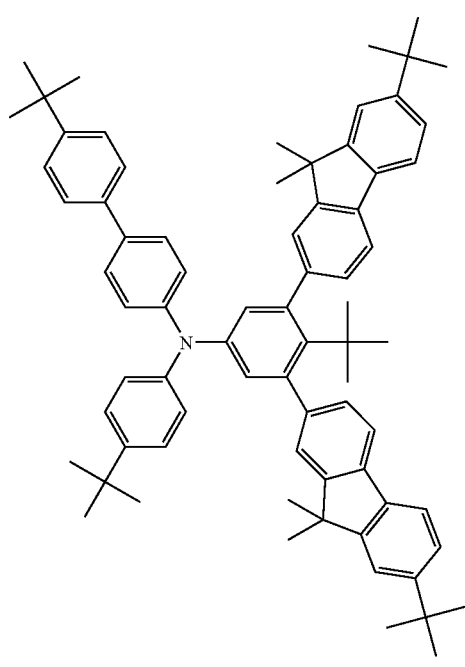
H-108
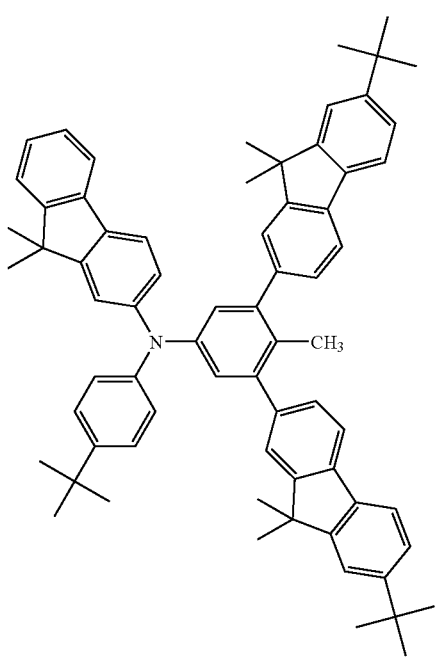
H-110

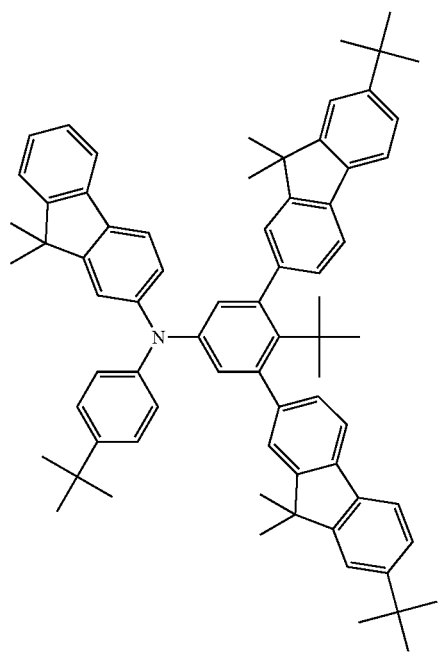
H-111
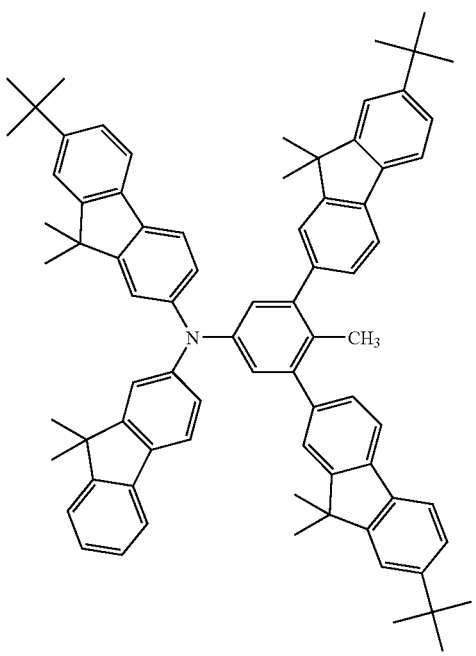
H-113
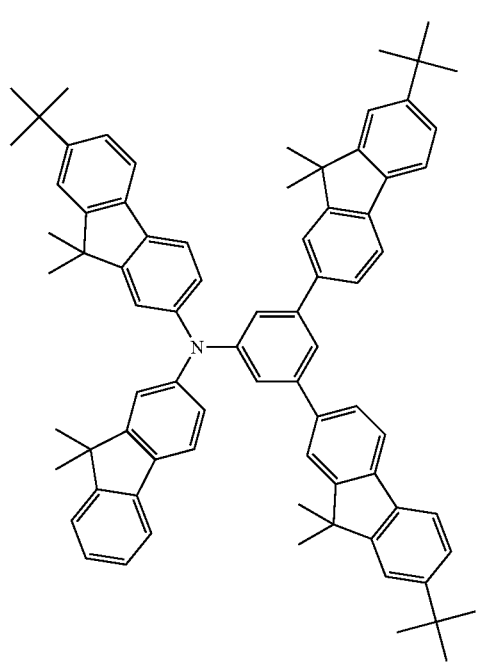
H-112
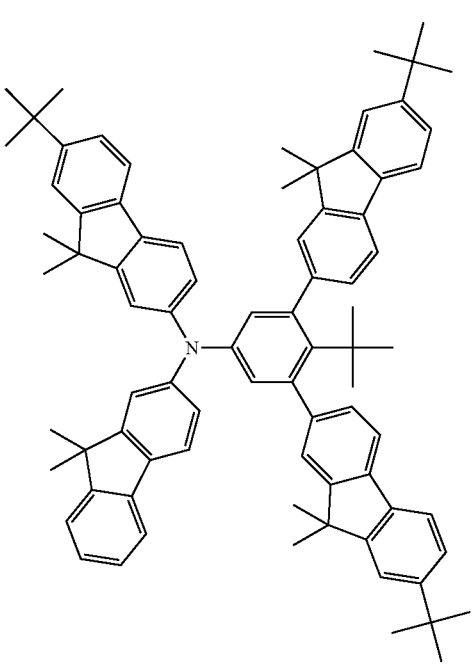
H-114

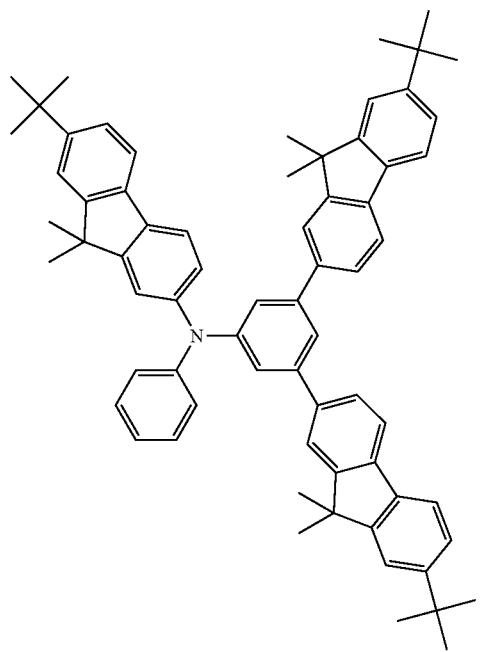
H-115
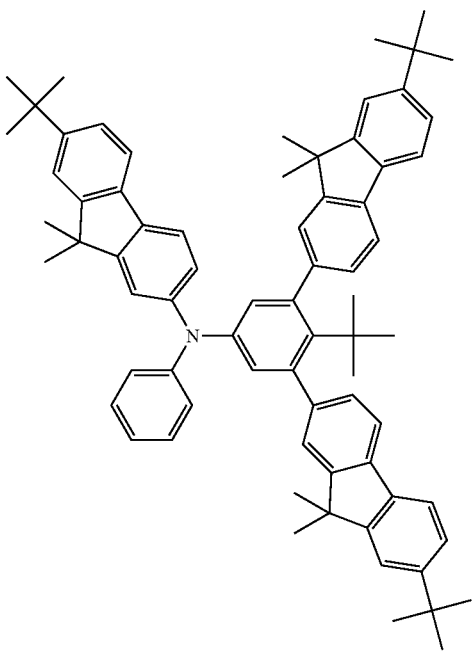
H-117
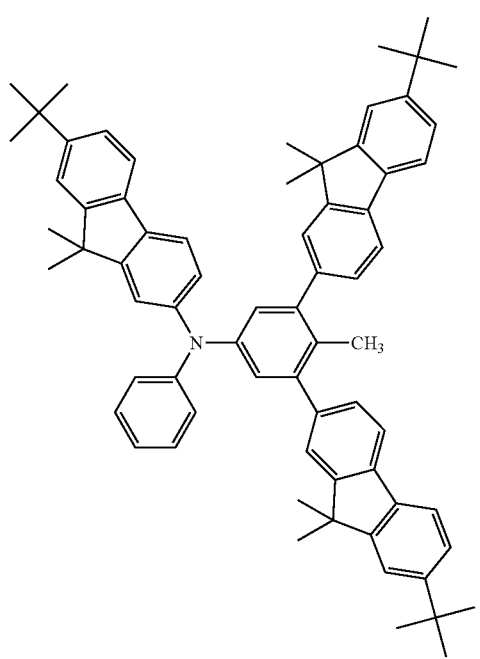
H-116
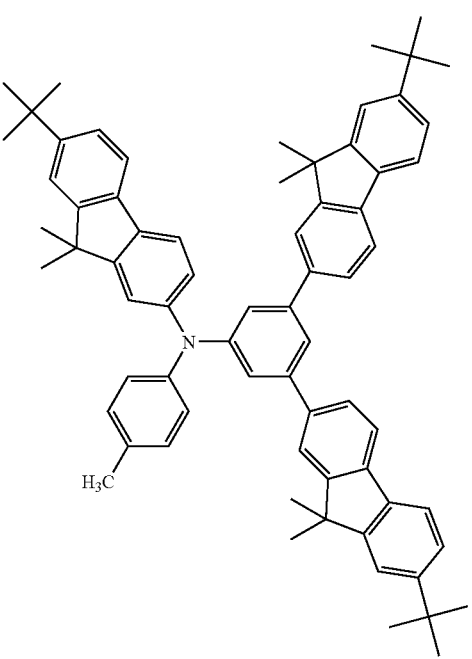
H-118

[Chemical formula 16]
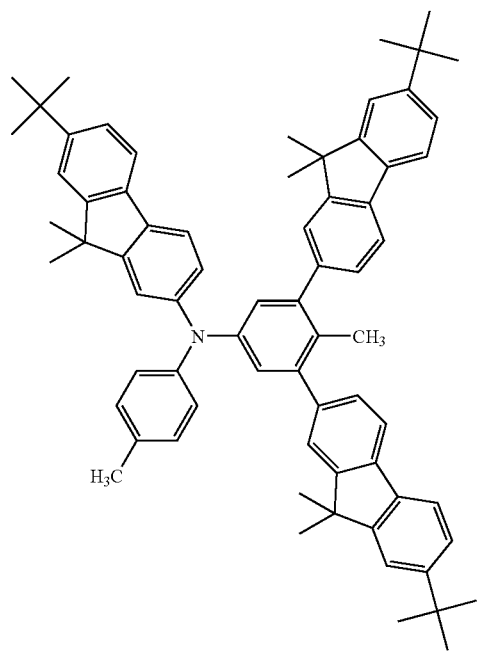
H-119
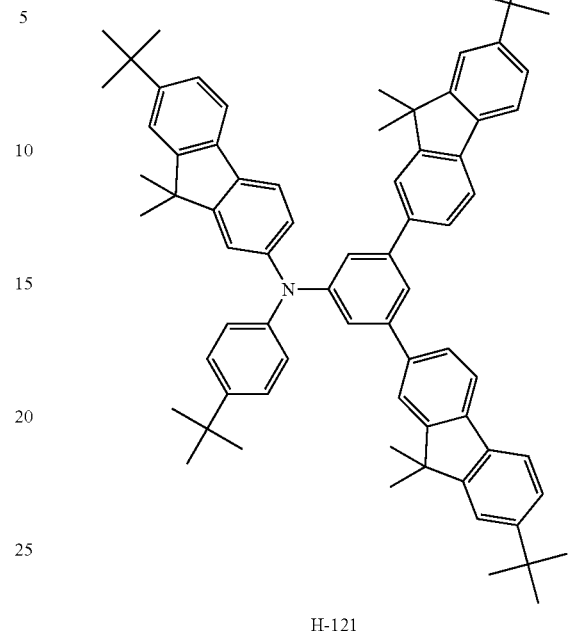
H-121
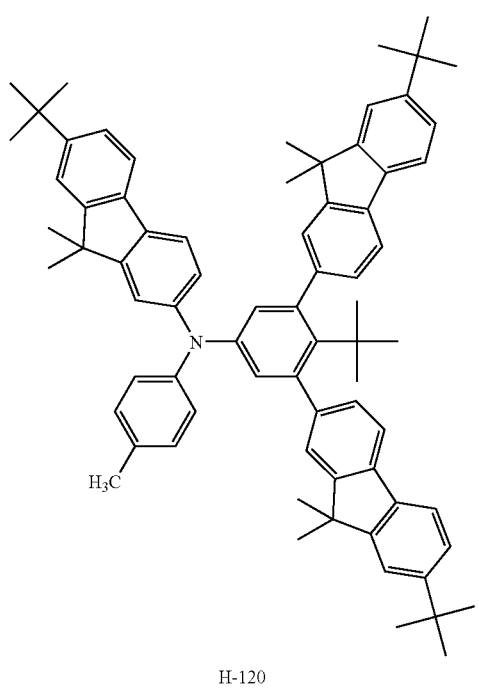
H-120
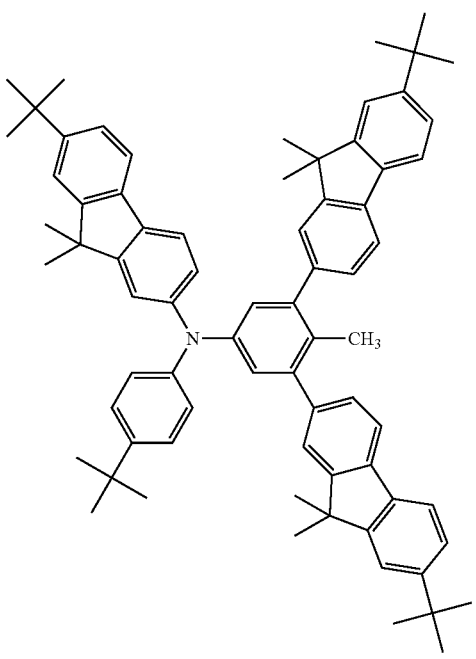
H-122

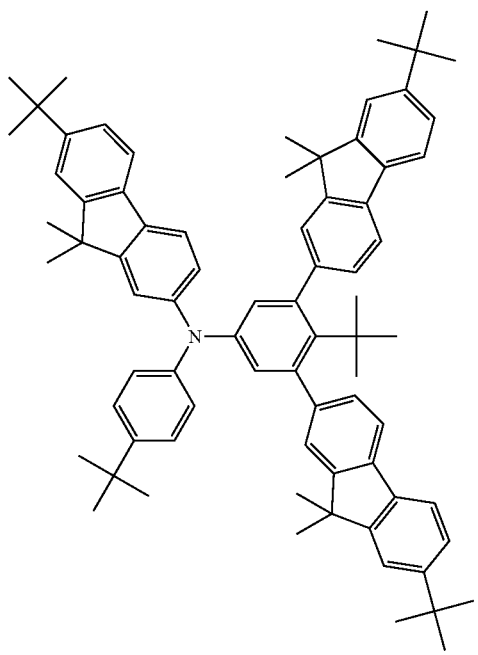
H-123
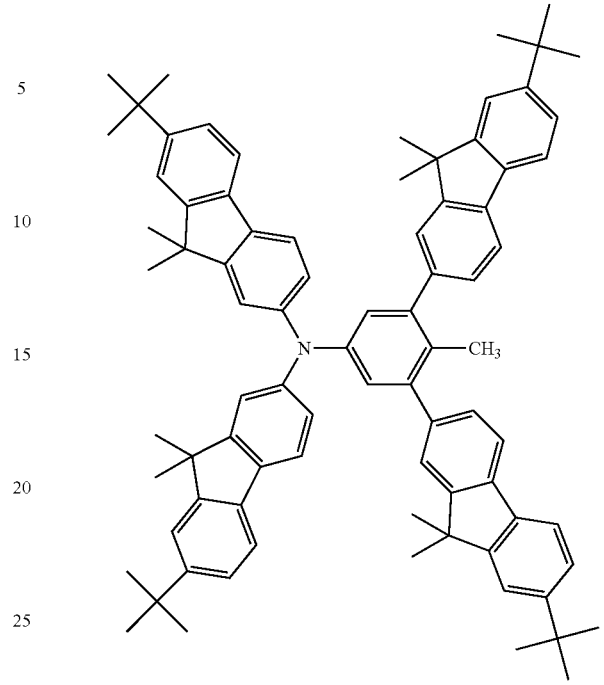
H-125
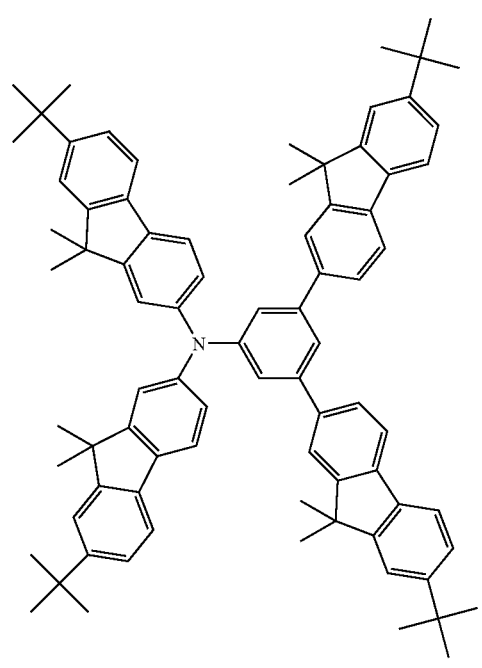
H-124
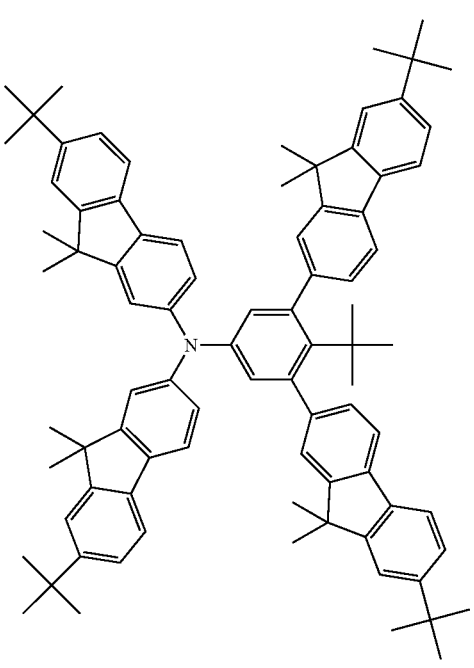
H-126

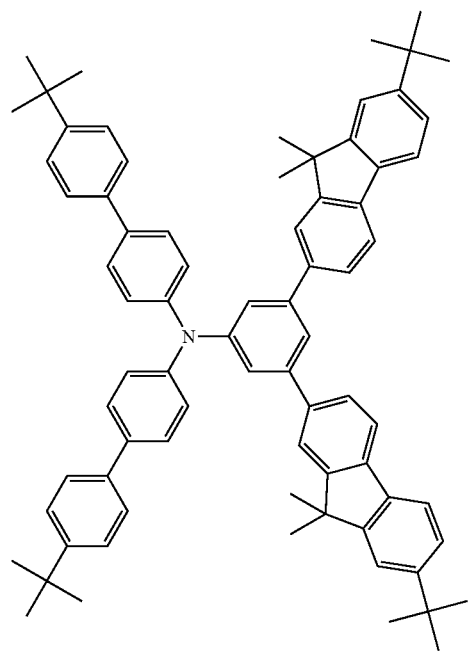
H-127
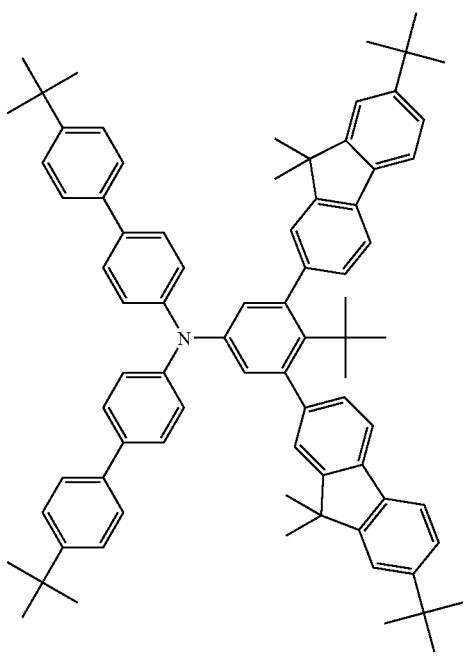
H-129
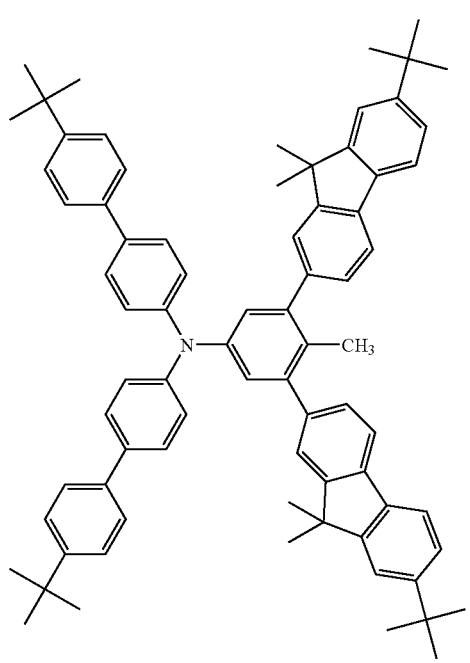
H-128
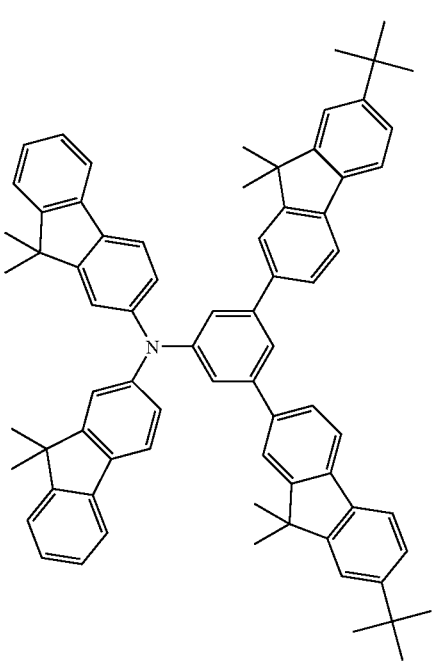
H-130

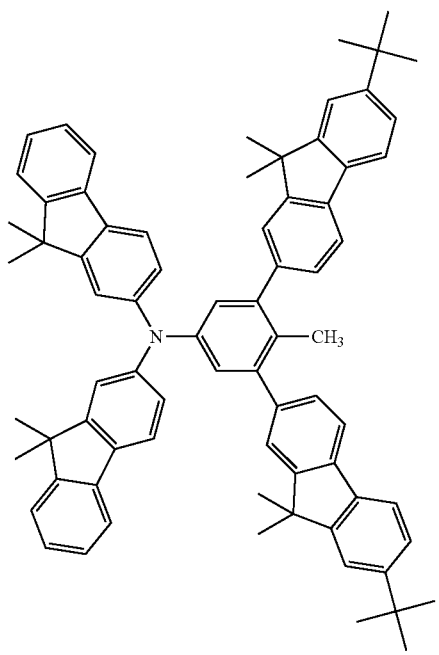
H-131
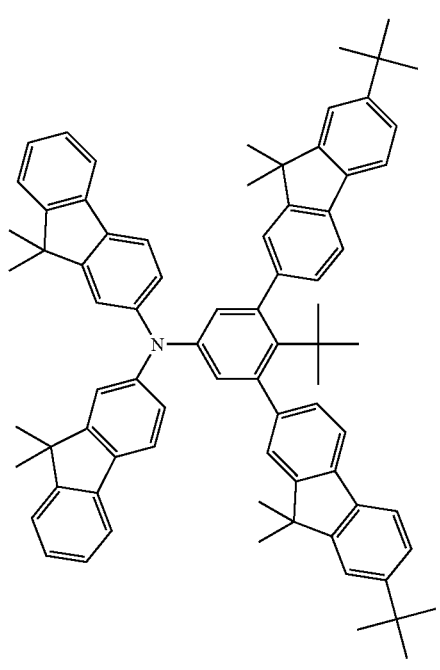
H-132
[Chemical formula 17]
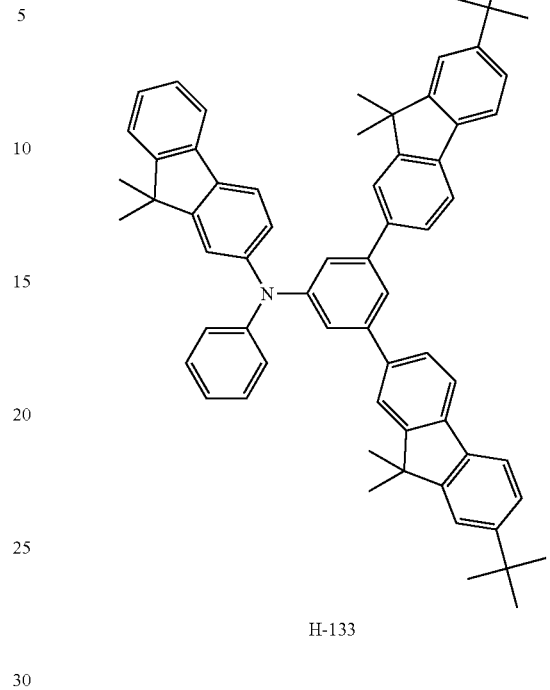
H-133
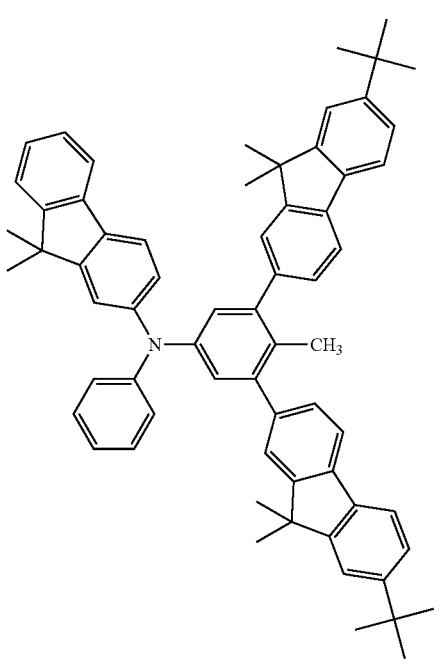
H-134

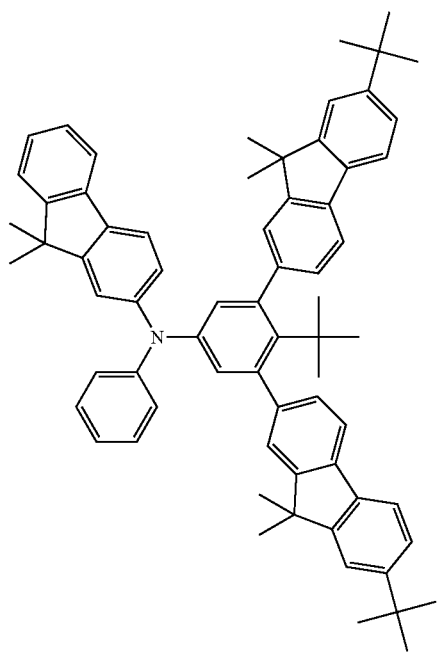
H-135
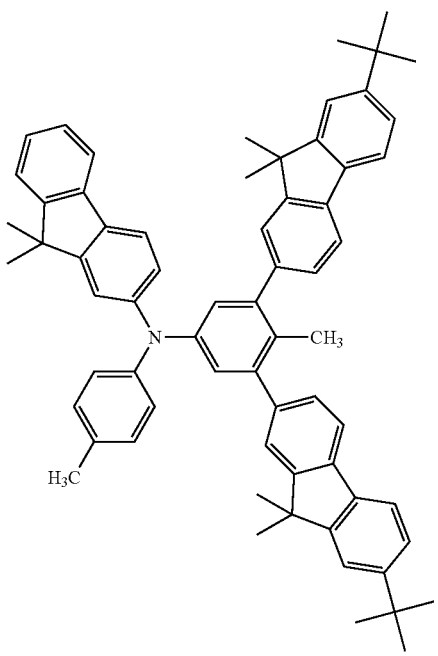
H-137
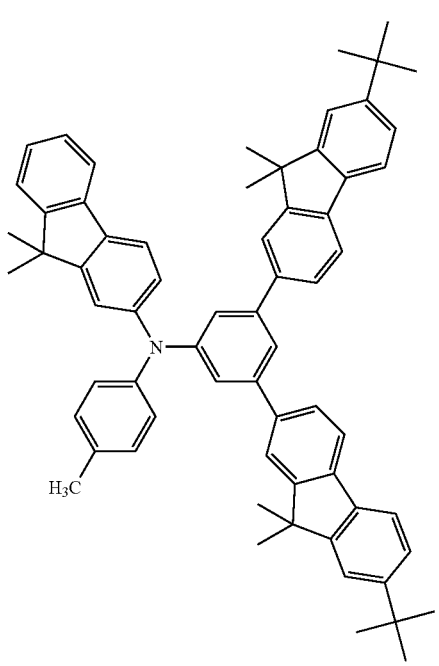
H-136
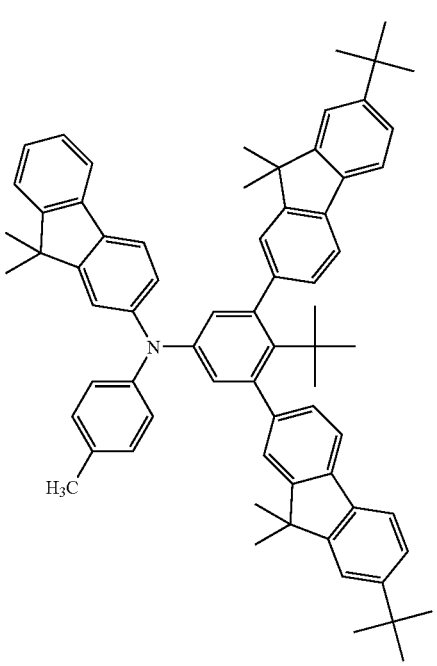
H-138

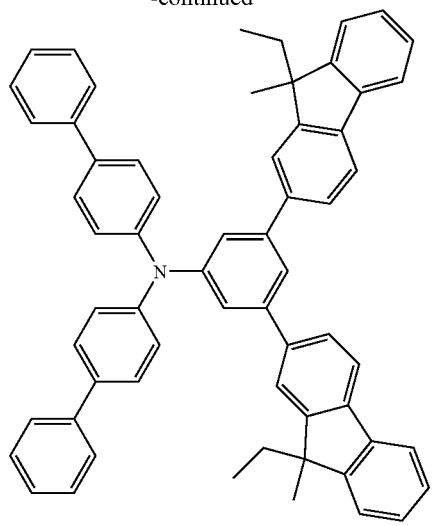
H-139
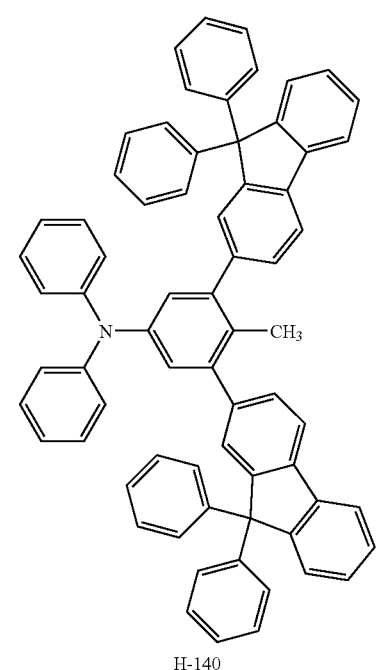
H-140
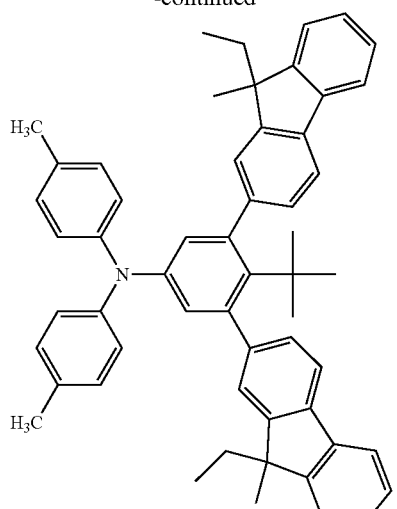
H-141
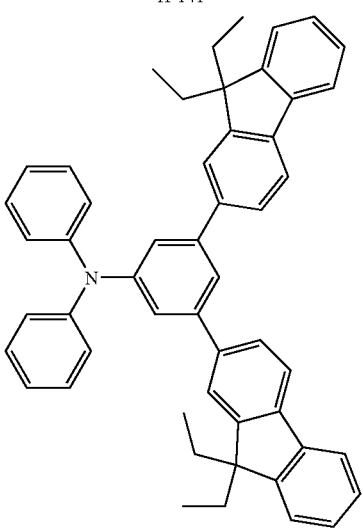
H-142
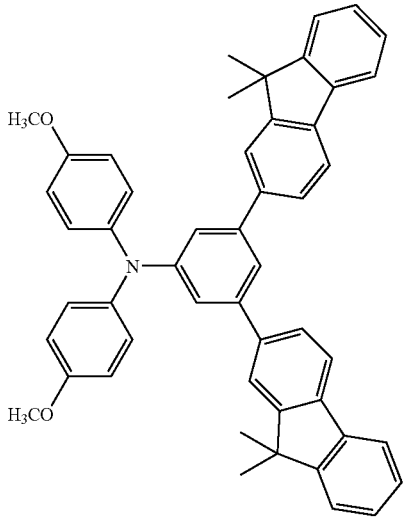
H-143

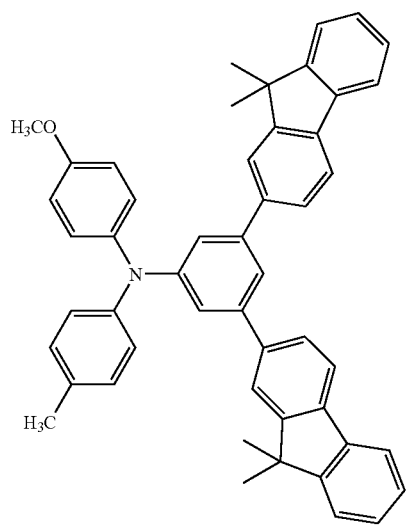
H-144
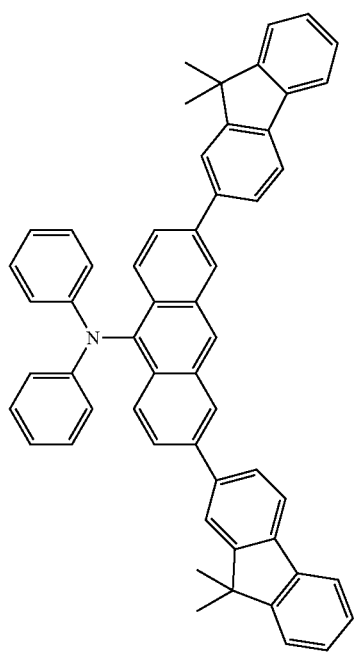
H-146
[Chemical formula 18]
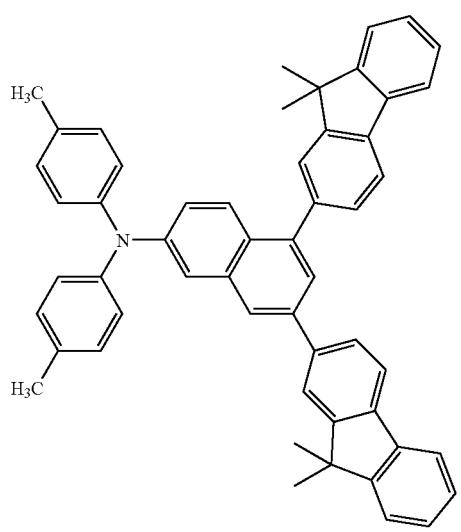
H-145
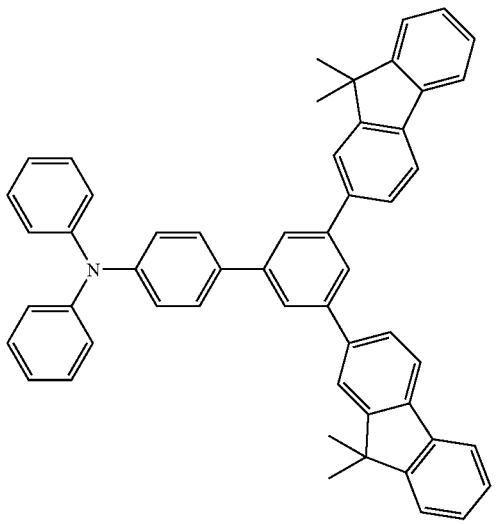
H-147

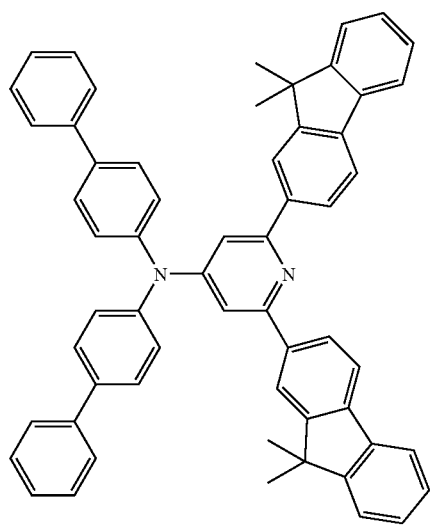
H-148
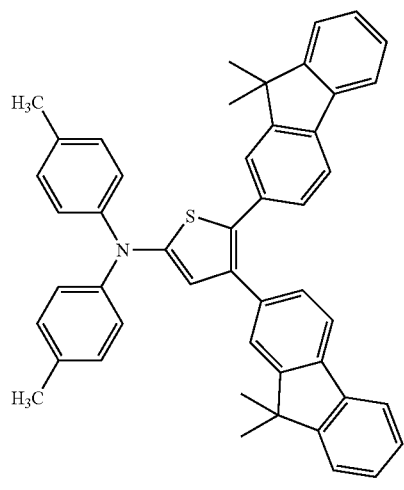
H-149
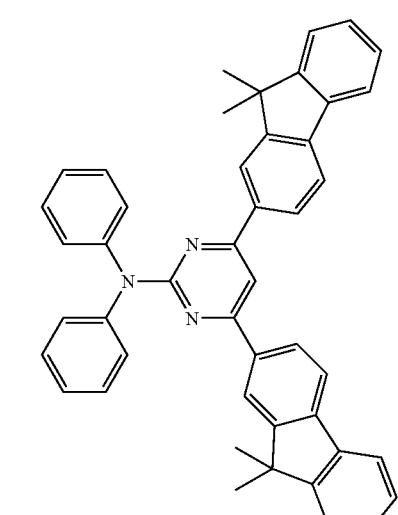
H-150
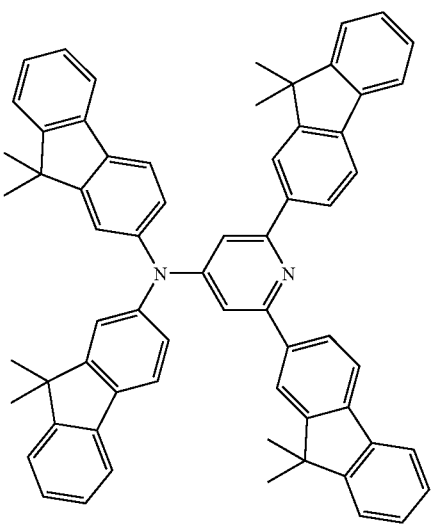
H-151
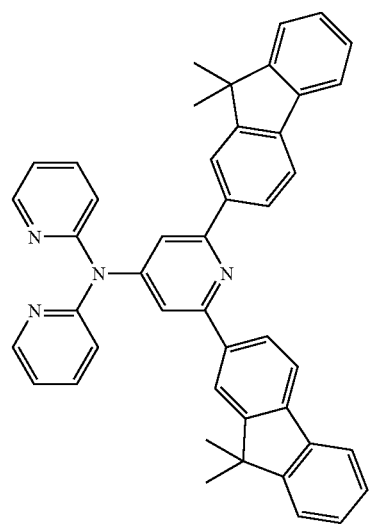
H-152
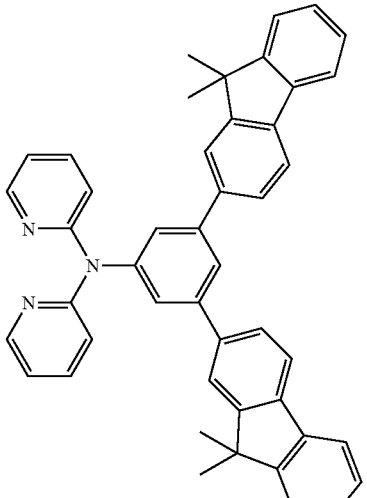
H-153

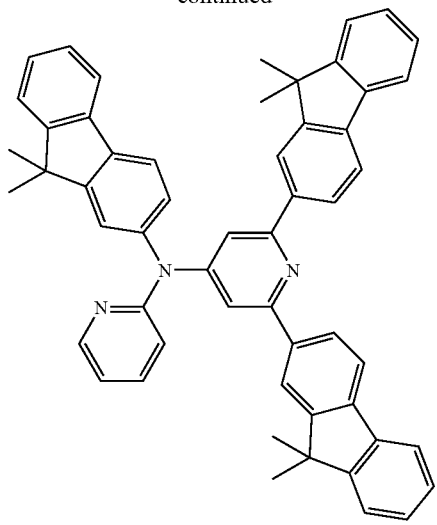
H-154
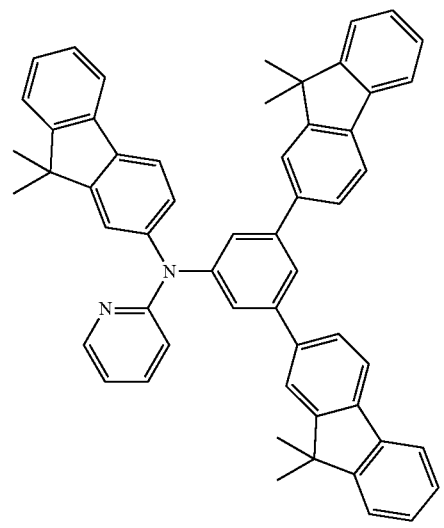
H-155
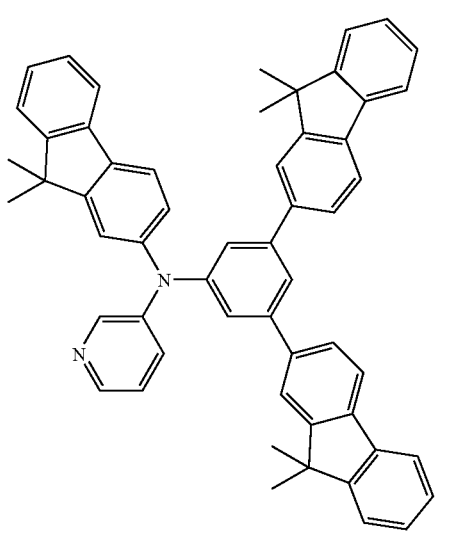
H-156
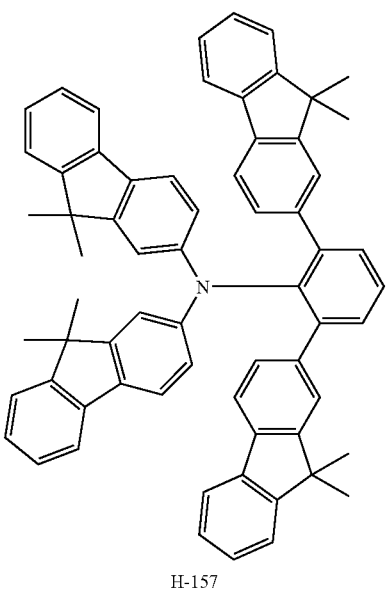
H-157
[Chemical formula 19]
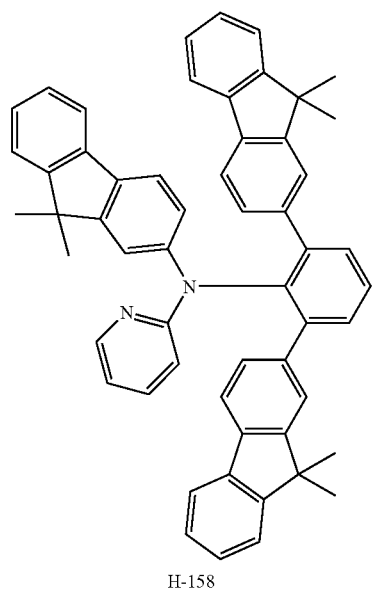
H-158

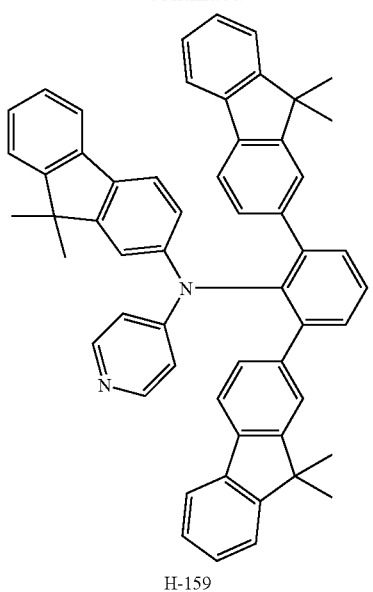
H-159
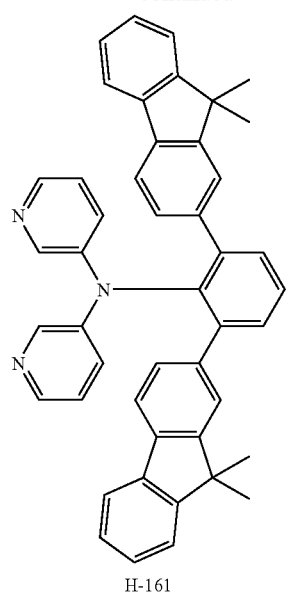
H-161
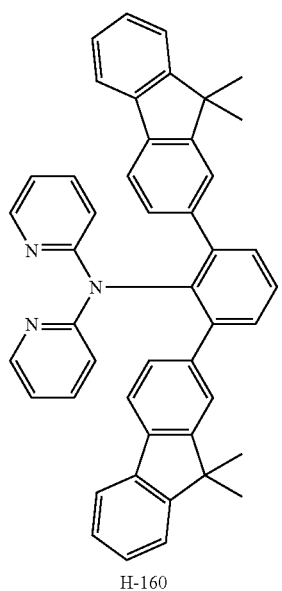
H-160
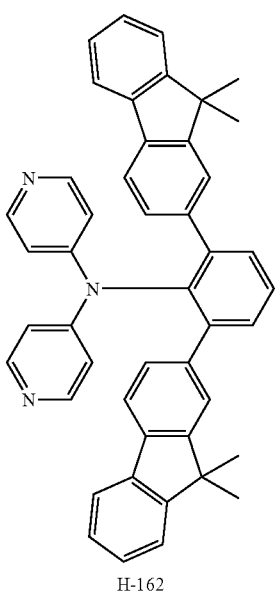
H-162

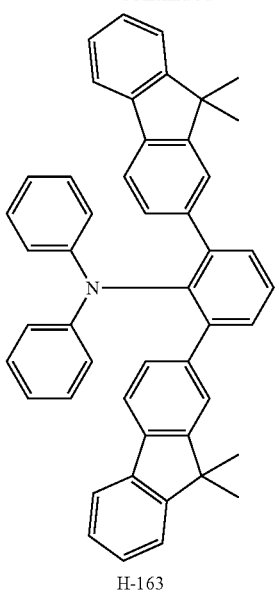
H-163
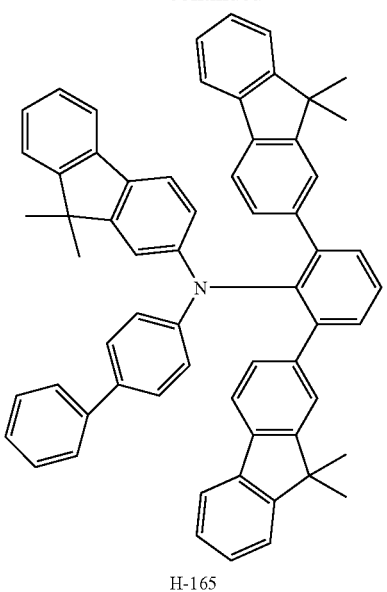
H-165
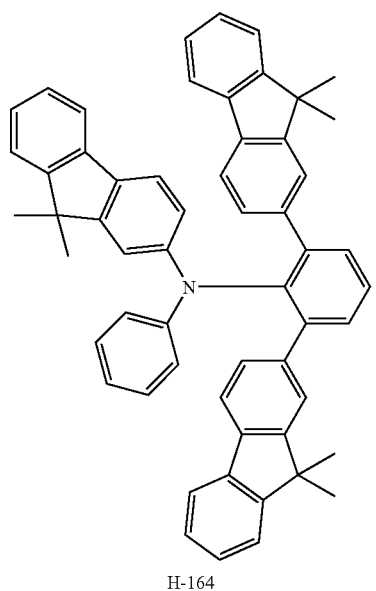
H-164
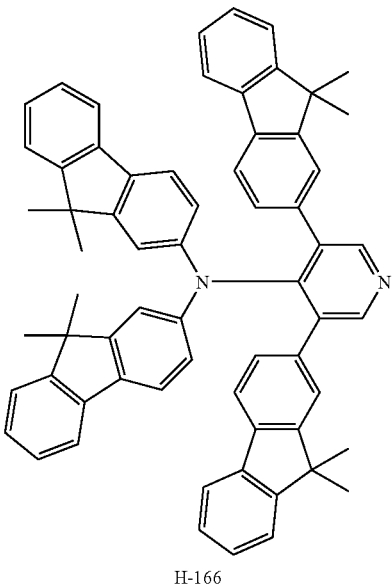
H-166

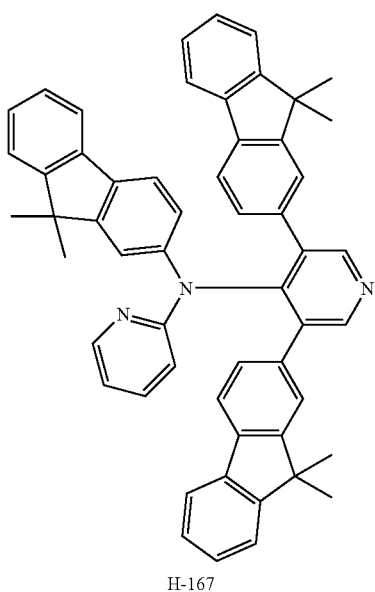
H-167
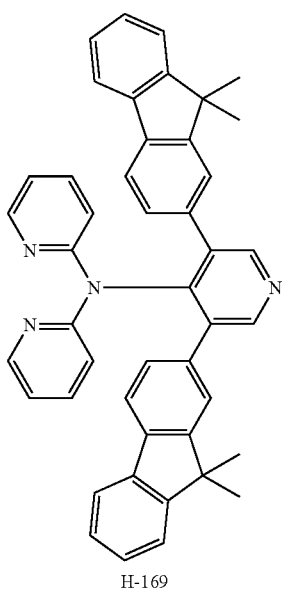
H-169
[Chemical formula 20]
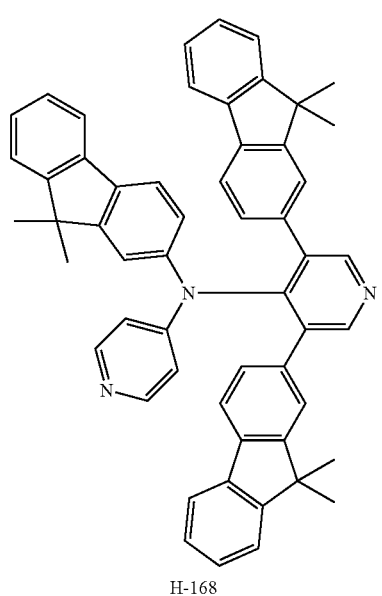
H-168
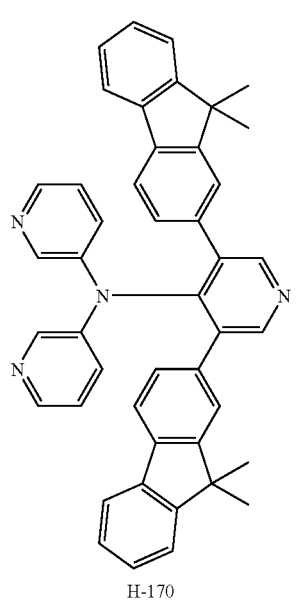
H-170

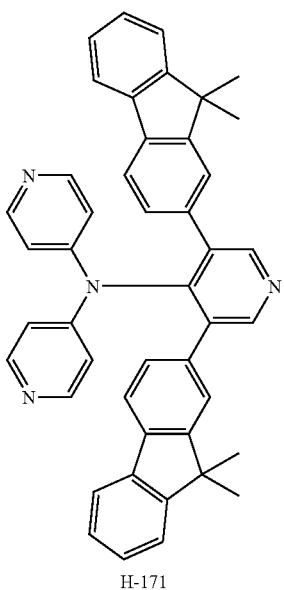

H-171

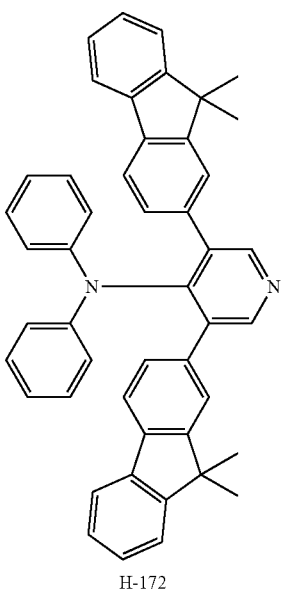

H-172

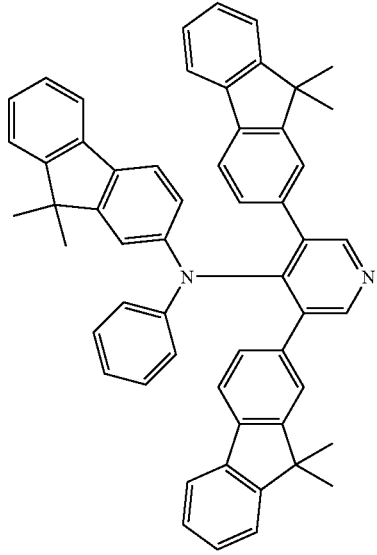

H-173

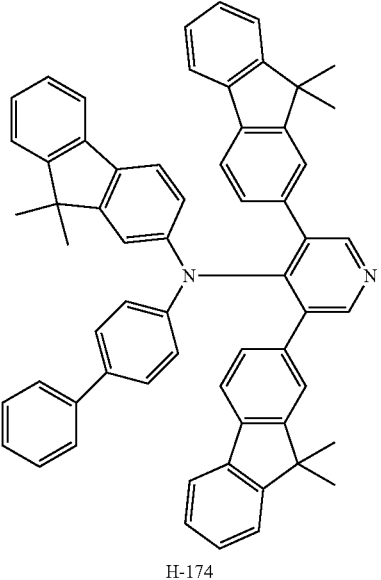

H-174

An organic light-emitting device of the present invention will now be described in detail.

An organic light-emitting device of the present invention includes a pair of electrodes composed of an anode and a cathode and an organic compound layer sandwiched between the pair of electrodes, wherein the organic compound layer contains the amino compound for an organic light-emitting device represented by any one of general formulae [1] to [5].

FIGS. 1 to 5 show examples of organic light-emitting devices of the present invention. First, reference numerals in the figures will be described. In the figures, reference numeral 1 indicates a substrate, reference numeral 2 indicates an anode, reference numeral 3 indicates a luminescent layer, reference numeral 4 indicates a cathode, reference numeral 5 indicates a hole-transporting layer, reference numeral 6 indicates an electron-transporting layer, reference numeral 7 indicates a hole injection layer, and reference numeral 8 indicates a hole or exciton blocking layer (hole/exciton blocking layer).

FIG. 1 is a cross-sectional view showing an organic light-emitting device according to an embodiment of the present invention. In the organic light-emitting device shown in FIG. 1, an anode 2, a luminescent layer 3, and a cathode 4 are provided on a substrate 1 in that order. The light-emitting device in this embodiment is useful for a case where the device has hole-transporting capacity, electron-transporting capacity, and light-emitting capacity by itself or a case where compounds having each capacity are combined for producing the device.

Figure 2:
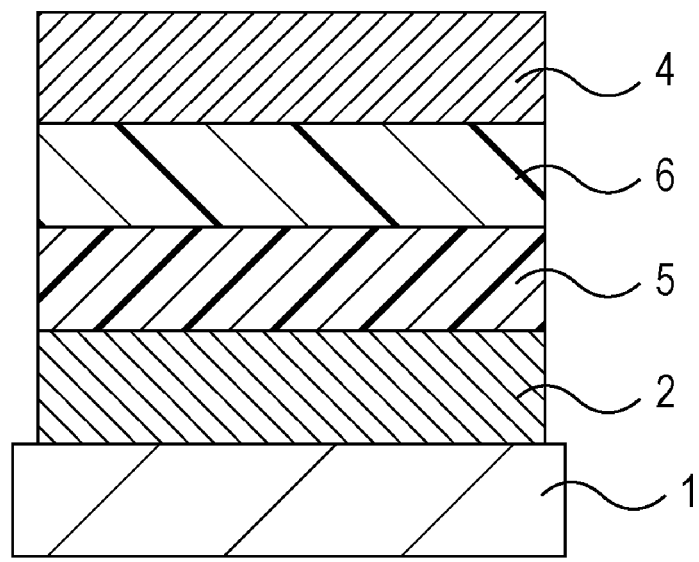
FIG. 2 is a cross-sectional view showing an organic light-emitting device according to an embodiment of the present invention.

FIG. 2 is a cross-sectional view showing an organic light-emitting device according to another embodiment of the present invention. In the organic light-emitting device shown in FIG. 2, an anode 2, a hole-transporting layer 5, an electron-transporting layer 6, and a cathode 4 are provided on a substrate 1 in that order. This device is useful for a case where a light-emitting material having either hole-transporting capacity or electron-transporting capacity or both hole-transporting capacity and electron-transporting capacity is used for each layer in combination with a simple hole-transporting material or an electron-transporting material that does not have light-emitting capacity. In this case, a luminescent layer 3 is composed of either the hole-transporting layer 5 or the electron-transporting layer 6.

Figure 3:
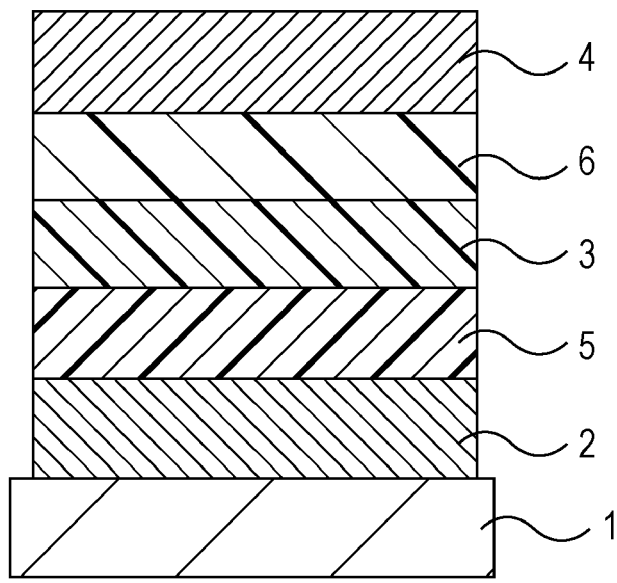
FIG. 3 is a cross-sectional view showing an organic light-emitting device according to an embodiment of the present invention.

FIG. 3 is a cross-sectional view showing an organic light-emitting device according to another embodiment of the present invention. In the organic light-emitting device shown in FIG. 3, an anode 2, a hole-transporting layer 5, a luminescent layer 3, an electron-transporting layer 6, and a cathode 4 are provided on a substrate 1 in that order. In this device, functions of carrier transportation and light emission are separated, and a compound having hole-transporting capacity, a compound having electron-transporting capacity, and a compound having light-emitting capacity are used in appropriate combinations. Accordingly, the degree of freedom of material selection is markedly increased, and various compounds having different emission wavelengths can be used. Therefore, diversification of luminescent color can be realized. Furthermore, luminous efficiency can also be improved by effectively trapping carriers or excitons in the central luminescent layer 3.

Figure 4:
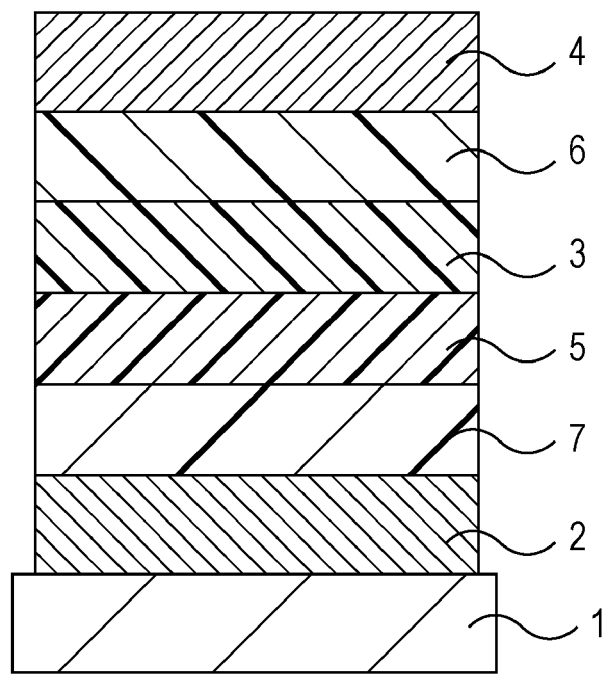
FIG. 4 is a cross-sectional view showing an organic light-emitting device according to an embodiment of the present invention.

FIG. 4 is a cross-sectional view showing an organic light-emitting device according to another embodiment of the present invention. In the organic light-emitting device shown in FIG. 4, a hole injection layer 7 is provided so as to be adjacent to the anode 2 in FIG. 3. This structure is effective for improving adhesiveness between the anode 2 and the hole-transporting layer 5 or improving hole-injection capacity, and thus effectively reduces the voltage to be applied.

Figure 5:
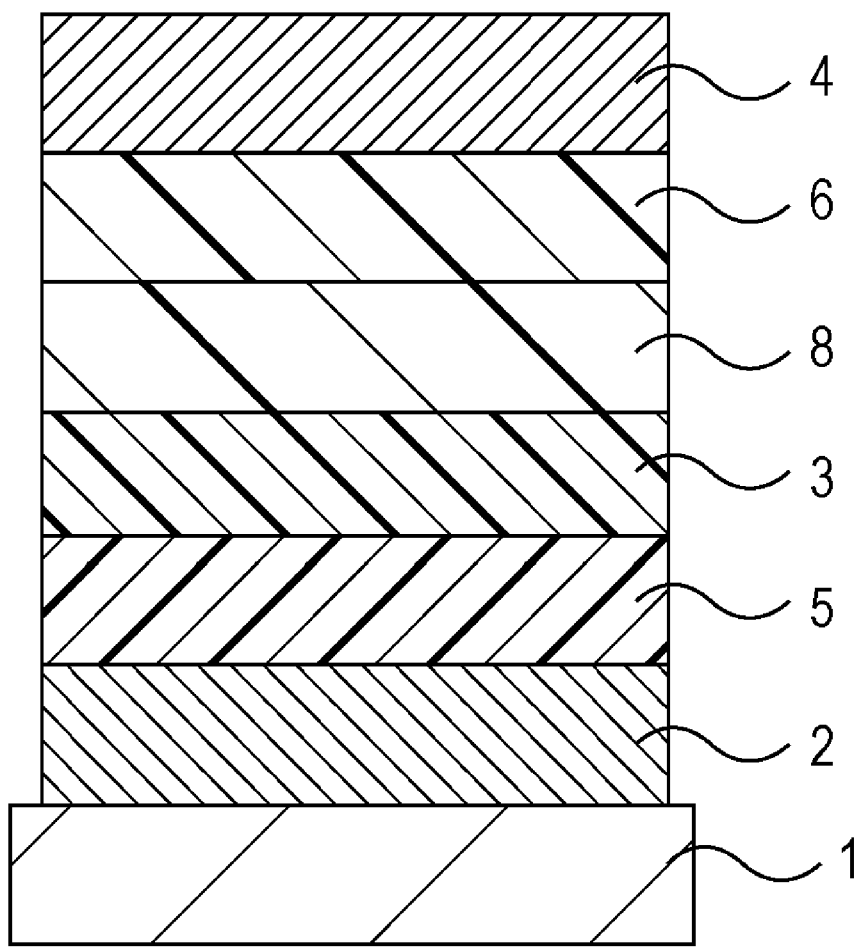
FIG. 5 is a cross-sectional view showing an organic light-emitting device according to an embodiment of the present invention.

FIG. 5 is a cross-sectional view showing an organic light-emitting device according to another embodiment of the present invention. In the organic light-emitting device shown in FIG. 5, a layer for blocking the passage of holes or excitons to the side of the cathode 4 (hole/exciton blocking layer 8) is provided between the luminescent layer 3 and the electron-transporting layer 6 in FIG. 3. Since a compound having a considerably high ionization potential is used for the hole/exciton blocking layer 8, this structure is effective in improving luminous efficiency.

The term "hole-transporting area containing the compound represented by any one of general formulae [1] to [5]" in the present invention means an area where holes are mainly injected or transported, for example, the above-mentioned hole injection layer 7 or the hole-transporting layer 5.

FIGS. 1 to 5 illustrate only basic device structures. The structure of organic light-emitting devices including the compound of the present invention is not limited thereto, and various layer structures are available. For example, an insulating layer may be provided at the interface between an electrode and an organic compound layer, an adhesion layer or an interference layer may be provided, or a hole-transporting layer may be composed of two layers having different ionization potentials.

The compounds represented by general formulae [1] to [5] of the present invention can be used in any of the forms illustrated in FIGS. 1 to 5.

In particular, an organic compound layer containing the compound of the present invention is useful as a luminescent layer, a hole injection layer, or a hole-transporting layer. In addition, a layer formed by, for example, vacuum deposition or solution coating is not easily crystallized and has an excellent stability with time.

In the present invention, the above compounds represented by general formulae [1] to [5] are used particularly as a component of a luminescent layer. However, a known low-molecular-weight or polymeric hole-transporting compound, luminescent compound, electron-transporting compound, or the like may also be used in combinations as required.

The substrate used in the present invention is not particularly limited, and opaque substrates such as metal substrates and ceramic substrates; and transparent substrates such as glass, quartz, and plastic sheets are used.

Furthermore, luminescent colors can be controlled using, for example, a color filter film, a fluorescent color conversion filter film, or a dielectric reflecting film as a substrate. In addition, a thin-film transistor (TFT) may be formed on a substrate and connected to other components to fabricate a device. A thin-film transistor is an example of a switching element for controlling luminescence and non-luminescence of the organic light-emitting device. The organic light-emitting device of the present invention can be installed as a display of display devices. The organic light-emitting device of the present invention can be used as a component of a display together with the switching element and a control unit.

Regarding the direction of light extraction of the device, the bottom-emission structure (structure for extracting light from the substrate side) and the top-emission structure (structure for extracting light from the opposite side of the substrate) are available.

EXAMPLES

The present invention will now be described more specifically using examples, but the present invention is not limited thereto.

Example 1

[Chemical formula 21]

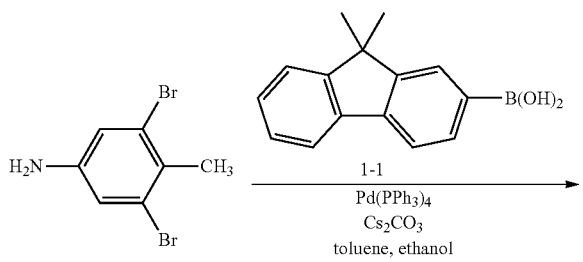

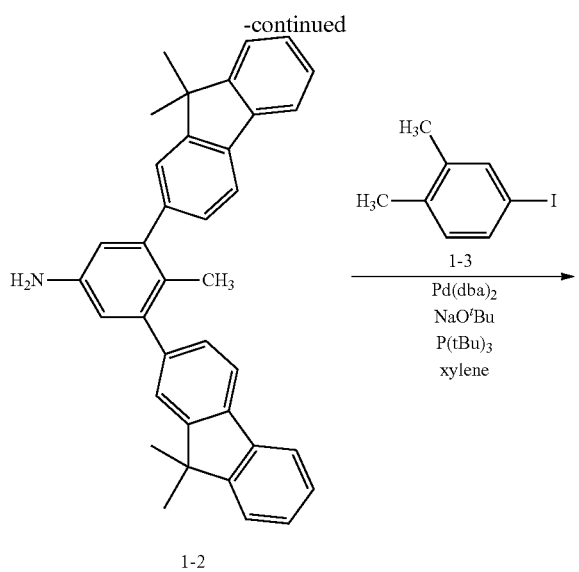

Synthesis of Exemplified Compound H-16

First, 0.79 g (3 mmol) of 3,5-dibromo-4-methylaniline and 2.14 g (9 mmol) of Compound 1-1 were dissolved in a mixed solution of 20 mL of toluene, 10 mL of ethanol, and 20 mL of an aqueous solution (2 mol/L) of cesium carbonate. Subsequently, 0.17 g (0.15 mmol) of tetrakis(triphenylphosphine) palladium (0) was added to the solution in a nitrogen atmosphere at room temperature under stirring. Stirring was performed for three hours while the reaction system was refluxed at the boiling point. After the reaction, the organic layer was extracted with toluene and dried over anhydrous sodium sulfate. The product was then purified with a silica gel column (using a mixture of heptane and toluene as a developing solvent) to obtain 1.11 g of Compound 1-2 (yield 75.4%).

Subsequently, 0.98 g (2 mmol) of Compound 1-2, 1.39 g (6 mmol) of Compound 1-3, and 0.48 g (5 mmol) of sodium tert-butoxide were dissolved in 50 mL of xylene. In a nitrogen atmosphere at room temperature under stirring, 17.2 mg (0.085 mmol) of tri-tert-butylphosphine was added to the solution, and 24.5 mg (0.043 mmol) of palladium dibenzylideneacetone was then added thereto. Stirring was performed for three hours while the reaction system was refluxed at the boiling point. After the reaction, the organic layer was extracted with toluene and dried over anhydrous sodium sulfate. The product was then purified with a silica gel column (using a mixture of heptane and toluene as a developing solvent) to obtain 0.966 g of Exemplified Compound H-16 (yield 72.1%).

A molecular ion (M+) peak at 699 of this compound was confirmed by matrix-assisted laser desorption ionization time-of-flight mass spectrometry (MALDI-TOF MS).

Examples 2 to 15

Synthesis of Exemplified Compounds H-2, H-5, H-11, H-17, H-50, H-53, H-65, H-68, H-71, H-77, H-86, H-125, H-128, and H-131

The title compounds could be synthesized as in Example 1 using boronic acid compounds and halogen compounds shown in Table 1 instead of Compounds 1-1 and 1-3.

TABLE 1

| Example | Exemplified Compound | Boronic acid compound | Halogen compound |
|---|---|---|---|
| 2 | H-2 | (9,9-dimethylfluoren-2-yl)B(OH)₂ | H₃C—C₆H₄—Br |
| 3 | H-5 | (9,9-dimethylfluoren-2-yl)B(OH)₂ | tBu—C₆H₄—Br |

TABLE 1-continued
| Example | Exemplified Compound | Boronic acid compound | Halogen compound |
|---|---|---|---|
| 4 | H-11 | 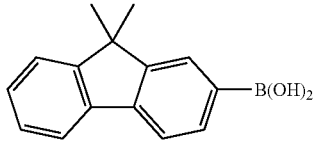 | 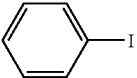 |
| 5 | H-17 | 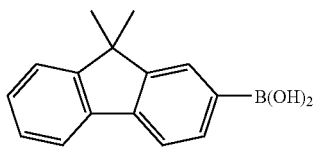 | 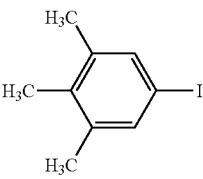 |
| 6 | H-50 | 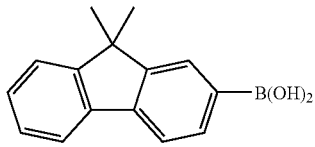 | 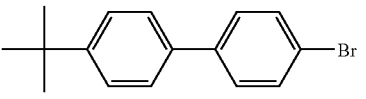 |
| 7 | H-53 | 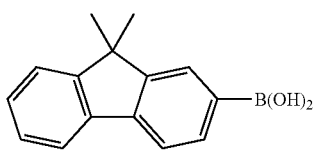 | 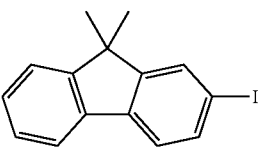 |
| 8 | H-65 | 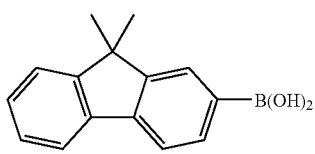 | 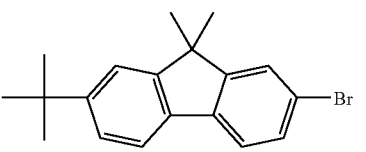 |
| 9 | H-68 | 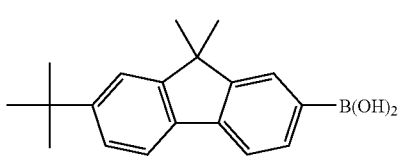 | 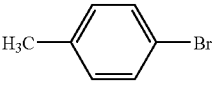 |
| 10 | H-71 | 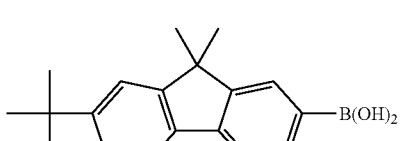 | 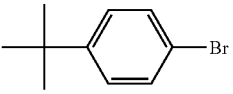 |
| 11 | H-77 | 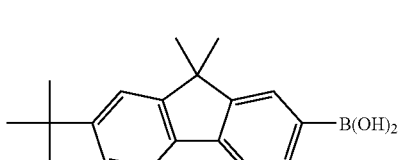 | 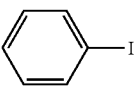 |
| 12 | H-86 | 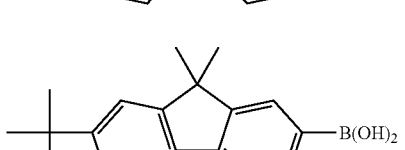 | 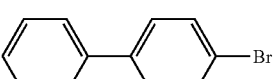 |

TABLE 1-continued

| Example | Exemplified Compound | Boronic acid compound | Halogen compound |
|---|---|---|---|
| 13 | H-125 | | |
| 14 | H-128 | | |
| 15 | H-131 | | |

Example 16

[Chemical formula 22]

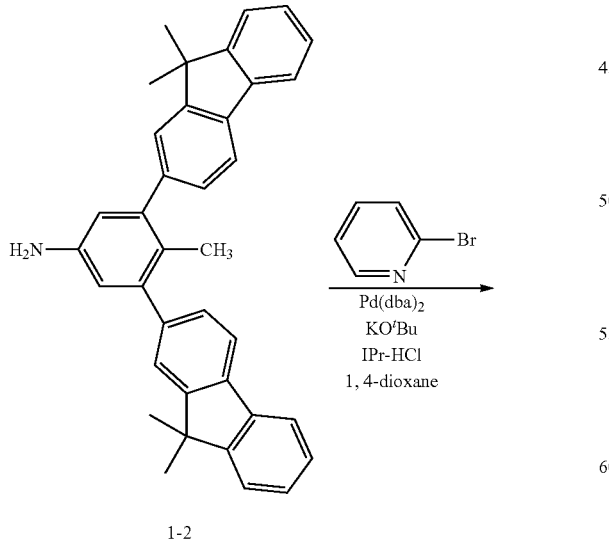

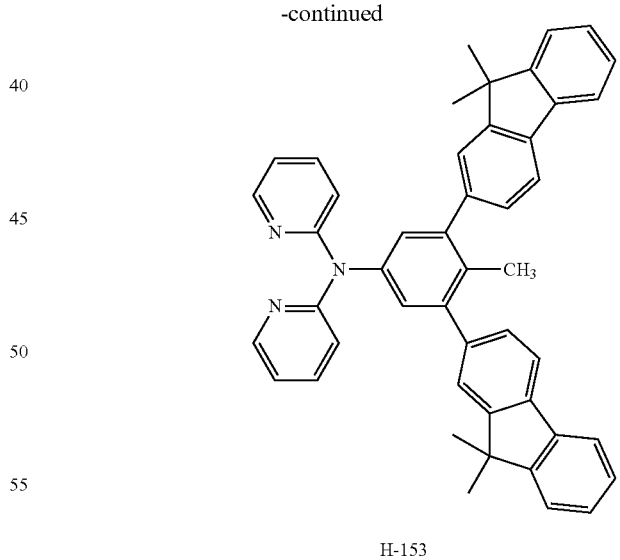

H-153

Synthesis of Exemplified Compound H-153

First, 1.0 g (2.04 mmol) of Compound 1-2 prepared as in Example 1, 0.97 g (6.12 mmol) of 2-bromopyridine, and 0.68 g (6.0 mmol) of potassium tert-butoxide were dissolved in 18 mL of 1,4-dioxane. In a nitrogen atmosphere at room temperature under stirring, 46 mg (0.1 mmol) of 1,3-bis(2,6-diisopropylphenyl)imidazole chloride (IPr—HCl) was added to the solution, and 30 mg (0.1 mmol) of palladium dibenzylideneacetone was then added thereto. The temperature of the reaction solution was increased to 100° C., and the solution was stirred for three hours. After the reaction, the organic layer was extracted with toluene and dried over anhydrous sodium sulfate. The product was then purified with a silica gel column (using a mixture of heptane and toluene as a developing solvent) to obtain 460 mg of Exemplified Compound H-153 (yield 35%). The structure of this compound was confirmed by NMR.

Example 17

[Chemical formula 23]

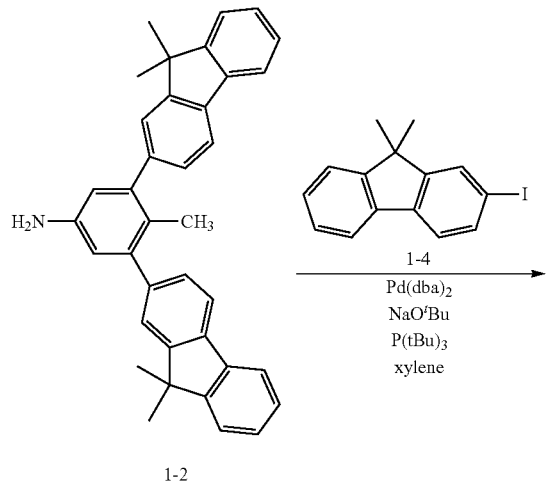

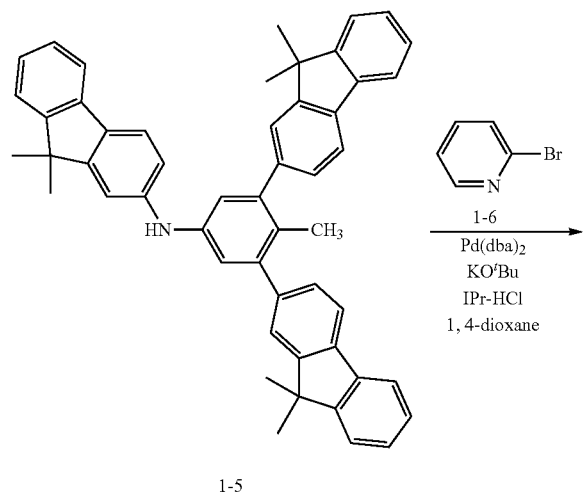

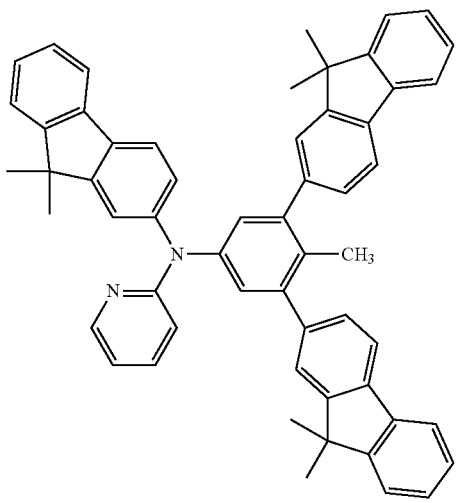

H-156

Synthesis of Exemplified Compound H-156

First, 2.0 g (4.07 mmol) of Compound 1-2 prepared as in Example 1, 1.43 g (4.47 mmol) of Compound 1-4, and 1.56 g (16.3 mmol) of sodium tert-butoxide were dissolved in 40 mL of xylene. In a nitrogen atmosphere at room temperature under stirring, 0.66 g (3.25 mmol) of tri-tert-butylphosphine was added to the solution, and 1.15 g (0.80 mmol) of palladium dibenzylideneacetone was then added thereto. Stirring was performed for 12 hours while the reaction system was refluxed at the boiling point. After the reaction, the organic layer was extracted with toluene and dried over anhydrous sodium sulfate. The product was then purified with a silica gel column (using a mixture of heptane and toluene as a developing solvent) to obtain 1.33 g of Compound 1-5 (yield 47%).

Subsequently, 1.0 g (1.46 mmol) of Compound 1-5, 0.69 g (4.39 mmol) of Compound 1-6, and 0.49 g (4.39 mmol) of potassium tert-butoxide were dissolved in 15 mL of 1,4-dioxane. In a nitrogen atmosphere at room temperature under stirring, 31 mg (0.07 mmol) of 1,3-bis(2,6-diisopropylphenyl)imidazole chloride (IPr—HCl) was added to the solution, and 42 mg (0.07 mmol) of palladium dibenzylideneacetone was then added thereto. The temperature of the reaction solution was increased to 100° C., and the solution was stirred for 30 hours. After the reaction, the organic layer was extracted with toluene and dried over anhydrous sodium sulfate. The product was then purified with a silica gel column (using toluene as a developing solvent) to obtain 730 mg of Exemplified Compound H-156 (yield 65%). The structure of this compound was confirmed by NMR.

Example 18

[Chemical formula 24]

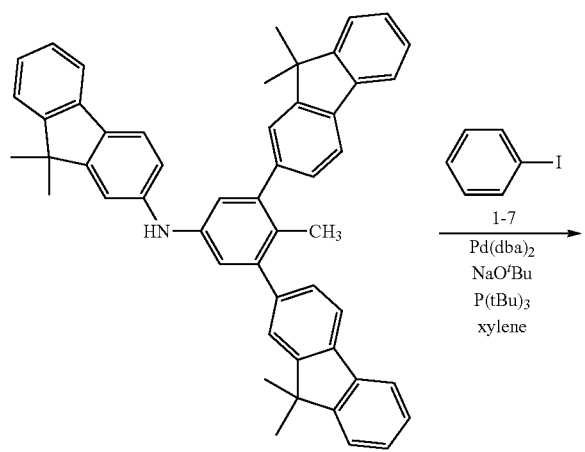

1-5

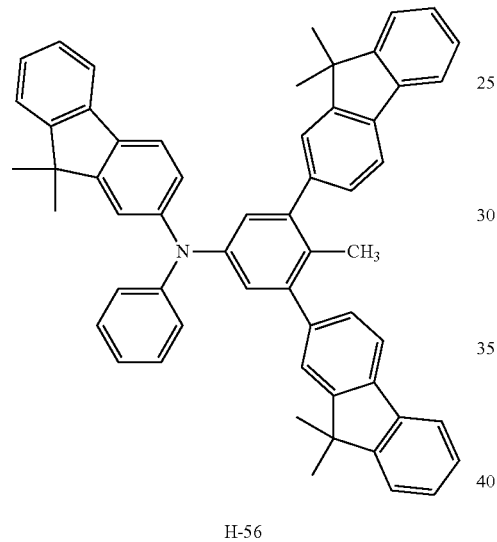

H-56

Synthesis of Exemplified Compound H-56

First, 1.0 g (1.46 mmol) of Compound 1-5 prepared as in Example 17, 0.75 g (3.66 mmol) of iodobenzene, and 0.56 g (5.84 mmol) of sodium tert-butoxide were dissolved in 25 mL of xylene. In a nitrogen atmosphere at room temperature under stirring, 0.24 g (1.17 mmol) of tri-tert-butylphosphine was added to the solution, and 0.168 g (0.29 mmol) of palladium dibenzylideneacetone was then added thereto. Stirring was performed for 12 hours while the reaction system was refluxed at the boiling point. After the reaction, the organic layer was extracted with toluene and dried over anhydrous sodium sulfate. The product was then purified with a silica gel column (using a mixture of heptane and toluene as a developing solvent) to obtain 633 mg of Exemplified Compound H-56 (yield 57%). The structure of this compound was confirmed by NMR.

Examples 19 to 25

Synthesis of Exemplified Compounds H-14, H-23, H-29, H-32, H-35, H-59, and H-62

The title compounds could be synthesized as in Examples 17 and 18 using halogen compounds I and halogen compounds II shown in Table 2 instead of Compounds 1-4, 1-6, and 1-7.

TABLE 2

| Example | Exemplified Compound | Halogen compound I | Halogen compound II |
|---|---|---|---|
| 19 | H-14 | Ph–I | H₃C–C₆H₄–Br |
| 20 | H-23 | Ph–I | tBu–C₆H₄–Br |
| 21 | H-29 | Ph–I | biphenyl–Br |
| 22 | H-32 | H₃C–C₆H₄–Br | biphenyl–Br |

TABLE 2-continued

| Example | Exemplified Compound | Halogen compound I | Halogen compound II |
|---|---|---|---|
| 23 | H-35 | 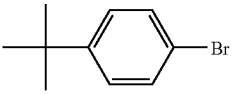 | 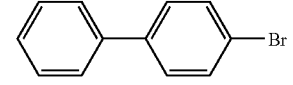 |
| 24 | H-59 | 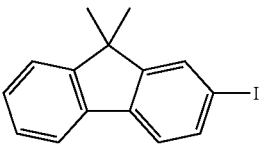 | 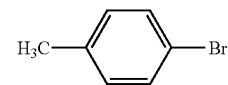 |
| 25 | H-62 | 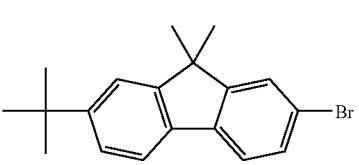 | 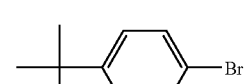 |

Example 26

An organic light-emitting device having the structure shown in FIG. 3 was prepared by the following process.

A transparent conductive supporting substrate was prepared by depositing indium tin oxide (ITO) serving as the anode 2 by sputtering on a glass substrate serving as the substrate 1 so as to have a film thickness of 120 nm. The substrate was sequentially washed with acetone and isopropyl alcohol (IPA) using ultrasonic waves, washed with boiled IPA, and then dried. Furthermore, the substrate was subjected to a UV/ozone cleaning and used as the transparent conductive supporting substrate.

The hole-transporting layer 5 was formed using Exemplified Compound H-16 by vacuum deposition so as to have a thickness of 20 nm. The vacuum deposition was performed under the conditions of a degree of vacuum of $1.0 \times 10^{-4}$ Pa and a deposition rate of 0.1 nm/sec.

Subsequently, Compound A shown below was evaporated as a luminescent layer on the hole-transporting layer 5 to form the luminescent layer 3 with a thickness of 20 nm. The vacuum deposition was performed under the conditions of a degree of vacuum of $1.0 \times 10^{-4}$ Pa and a deposition rate of 0.1 nm/sec.

[Chemical formula 25]

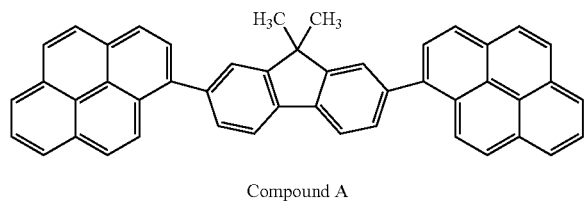

Compound A

Furthermore, a bathophenanthroline (Bphen) film was formed as the electron-transporting layer 6 by vacuum deposition so as to have a thickness of 40 nm. The vacuum deposition was performed under the conditions of a degree of vacuum of $1.0 \times 10^{-4}$ Pa and a deposition rate in the range of 0.2 to 0.3 nm/sec.

A lithium fluoride film having a thickness of 0.5 nm was then formed on the above organic compound layer by vacuum deposition, and an aluminum film having a thickness of 150 nm was further formed on the lithium fluoride film by vacuum deposition. Thus, an organic light-emitting device including an electron-injecting electrode (cathode 4) formed of an aluminum-lithium alloy film was prepared. The vacuum deposition was performed under the conditions of a degree of vacuum of $1.0 \times 10^{-4}$ Pa and a deposition rate in the range of 1.0 to 1.2 nm/sec.

The prepared organic EL device was covered with a protective glass plate in a dry air atmosphere and sealed with an acrylic resin adhesive so as to prevent degradation of the device due to adsorption of moisture.

When a voltage of 4.0 V was applied to the device thus prepared using the ITO electrode (anode 2) as the anode and the Al electrode (cathode 4) as the cathode, blue-light emission was observed.

Furthermore, a voltage was applied while the current density was maintained at 30 mA/cm² in a nitrogen atmosphere. As a result, after 100 hours, the degradation of luminance relative to the initial luminance was small.

Examples 27 to 31

Devices could be prepared as in Example 26 except that compounds shown in Table 3 were used instead of Exemplified Compound H-16, which constituted the hole-transporting layer 5 of Example 26.

TABLE 3

| Example | Exemplified Compound |
|---|---|
| 27 | H-2 |
| 28 | H-5 |
| 29 | H-11 |
| 30 | H-50 |
| 31 | H-53 |

Comparative Examples 1 and 2

Devices were prepared as in Example 26 except that Comparative Compounds 4-1 and 4-2 shown below were used instead of Exemplified Compound H-16. When a voltage of 4.0 V was applied to each device using the ITO electrode (anode 2) as the anode and the Al electrode (cathode 4) as the cathode, light emission was not observed.

[Chemical formula 26]

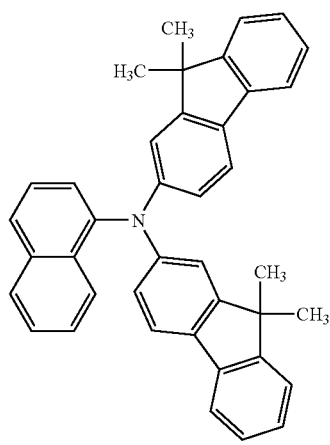

4-1

[Chemical formula 27]

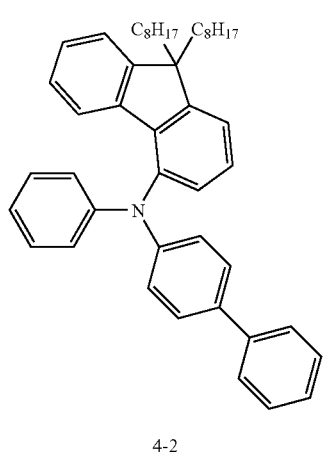

4-2

Example 32

An organic light-emitting device having the structure shown in FIG. 4 was prepared by the following process.

A transparent conductive supporting substrate was prepared by depositing indium tin oxide (ITO) serving as the anode 2 by sputtering on a glass substrate serving as the substrate 1 so as to have a film thickness of 120 nm. The substrate was sequentially washed with acetone and isopropyl alcohol (IPA) using ultrasonic waves, washed with boiled IPA, and then dried. Furthermore, the substrate was subjected to a UV/ozone cleaning and used as the transparent conductive supporting substrate.

A chloroform solution of Exemplified Compound H-53, which was used for the hole injection layer 7, was prepared so as to have a concentration of 0.1 weight percent.

This solution was dripped on the ITO electrode of the substrate, and spin coating was then performed at a rotational speed of 500 PRM for 10 seconds followed by a rotational speed of 1,000 PRM for one minute to form a film. The substrate was then dried in a vacuum oven at 80° C. for 10 minutes to completely remove the solvent in the thin film. The thickness of the resulting hole injection layer 7 was 11 nm.

Subsequently, Exemplified Compound H-16 serving as a hole-transporting layer was deposited on the hole injection layer 7 to form the hole-transporting layer 5 having a thickness of 20 nm. The vacuum deposition was performed under the conditions of a degree of vacuum of $1.0 \times 10^{-4}$ Pa and a deposition rate of 0.1 nm/sec.

Furthermore, a luminescent layer, an electron-transporting layer, and an Al electrode were formed as in Example 26.

When a voltage was applied to the device thus prepared using the ITO electrode (anode 2) as the anode and the Al electrode (cathode 4) as the cathode, light emission was observed.

Furthermore, a voltage was applied while the current density was maintained at 30 mA/cm² in a nitrogen atmosphere. As a result, after 100 hours, the degradation of luminance relative to the initial luminance was small.

Example 33

An organic light-emitting device having the structure shown in FIG. 3 was prepared by the following process.

A transparent conductive supporting substrate was prepared by depositing indium tin oxide (ITO) serving as the anode 2 by sputtering on a glass substrate serving as the substrate 1 so as to have a film thickness of 120 nm. The substrate was sequentially washed with acetone and isopropyl alcohol (IPA) using ultrasonic waves, washed with boiled IPA, and then dried. Furthermore, the substrate was subjected to a UV/ozone cleaning and used as the transparent conductive supporting substrate.

The hole-transporting layer 5 was formed using Compound B by vacuum deposition so as to have a thickness of 30 nm. The vacuum deposition was performed under the conditions of a degree of vacuum of $1.0 \times 10^{-4}$ Pa and a deposition rate of 0.1 nm/sec. Subsequently, a luminescent layer was formed on the hole-transporting layer 5 by codeposition of Exemplified Compound H-53 and Compound C so that the weight ratio of Compound C in the luminescent layer would be 10%, thus forming the luminescent layer 3 having a thickness of 50 nm. The codeposition was performed under the conditions of a degree of vacuum of $1.0 \times 10^{-4}$ Pa and a deposition rate of 0.1 nm/sec.

[Chemical formula 28]

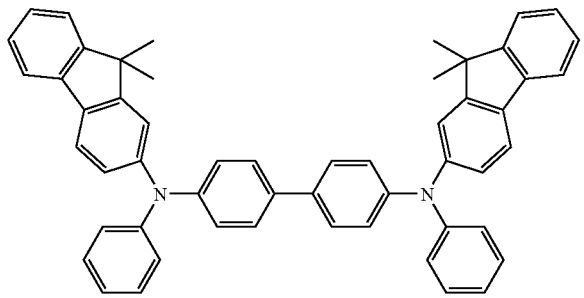

Compound B

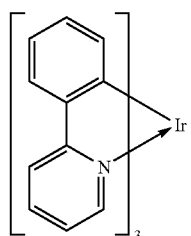

Compound C

Furthermore, a bathophenanthroline (Bphen) film was formed as the electron-transporting layer 6 by vacuum deposition so as to have a thickness of 40 nm. The vacuum deposition was performed under the conditions of a degree of vacuum of $1.0 \times 10^{-4}$ Pa and a deposition rate in the range of 0.2 to 0.3 nm/sec.

A potassium fluoride film having a thickness of 0.5 nm was then formed on the above organic compound layer by vacuum deposition, and an aluminum film having a thickness of 150 nm was further formed on the potassium fluoride film by vacuum deposition. Thus, an organic light-emitting device including an electron-injecting electrode (cathode 4) formed of an aluminum-potassium alloy film was prepared. The vacuum deposition was performed under the conditions of a degree of vacuum of $1.0 \times 10^{-4}$ Pa and a deposition rate in the range of 1.0 to 1.2 nm/sec.

The prepared organic EL device was covered with a protective glass plate in a dry air atmosphere and sealed with an acrylic resin adhesive so as to prevent degradation of the device due to adsorption of moisture.

When a voltage of 4 V was applied to the device thus prepared using the ITO electrode (anode 2) as the anode and the Al electrode (cathode 4) as the cathode, green-light emission was observed.

Examples 34 to 38

Devices could be prepared as in Example 33 except that compounds shown in Table 4 were used instead of Exemplified Compound H-53, which constituted the luminescent layer 3 of Example 33.

TABLE 4

| Example | Exemplified Compound |
| --- | --- |
| 34 | H-2 |
| 35 | H-9 |
| 36 | H-56 |
| 37 | H-153 |
| 38 | H-155 |

Example 39

A device could be prepared as in Example 33 except that Compound D shown below was used instead of Compound C, which constituted the luminescent layer 3 of Example 33.

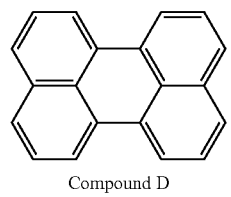

Compound D

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures and functions.

This application claims the benefit of Japanese Application No. 2006-088351 filed Mar. 28, 2006 and No. 2007-023115 filed Feb. 1, 2007, which are hereby incorporated by reference herein in their entirety.

What is claimed is:

1. An amino compound represented by general formula:

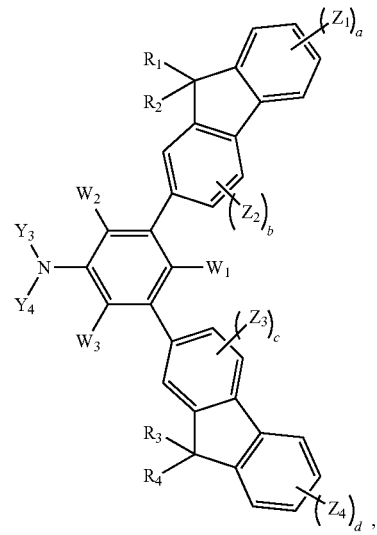

wherein $Z_1$, $Z_2$, $Z_3$, and $Z_4$ each represents a group selected from the group consisting of a hydrogen atom and a substituted or unsubstituted alkyl group, and are the same or different;

$W_1$, $W_2$, and $W_3$ each represents a group selected from the group consisting of a hydrogen atom and a substituted or unsubstituted alkyl group and alkoxy group, and are the same or different;

$Y_3$ and $Y_4$ each represents a group selected from the group consisting of a substituted or unsubstituted alkyl group, aryl group and heterocyclic group, and are the same or different, $Y_3$ and $Y_4$ not being fluoren-4-yl group;

$R_1$ to $R_4$ each represents a group selected from the group consisting of a hydrogen atom and a substituted or unsubstituted alkyl group, aryl group and heterocyclic group, and are the same or different; and a and d each represents an integer of 1 to 4; and b and c each represents an integer of 1 to 3.

2. The amino compound according to claim 1, which is selected from the group consisting of formulas (1)-(4):

(1)
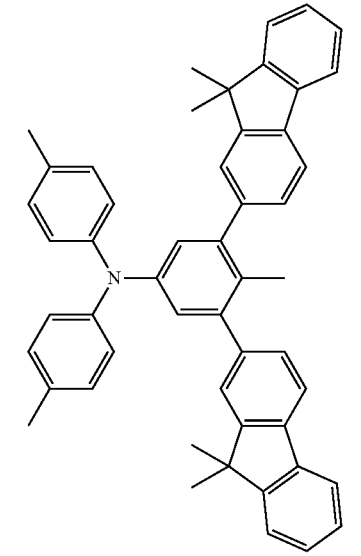

(2)
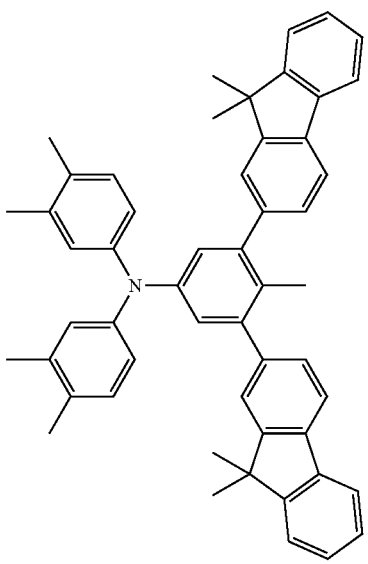

(3)
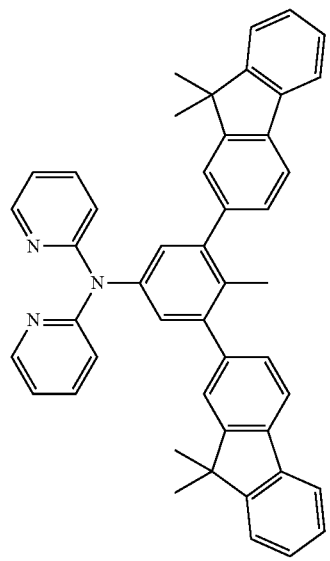

(4)
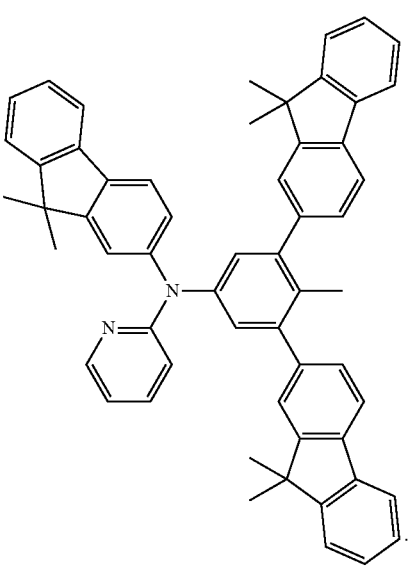

3. An organic light-emitting device comprising at least a pair of electrodes composed of an anode, a cathode, and an organic compound layer disposed therebetween,
wherein the organic compound layer is a luminescent layer, and the luminescent layer comprises a phosphorescent luminescent material and the amino compound according to claim 1.

4. An organic light-emitting device comprising at least a pair of electrodes composed of an anode, a cathode, and an organic compound layer disposed therebetween,
wherein the organic light-emitting device further comprises a luminescent layer disposed between the anode and the cathode,
wherein the luminescent layer has a phosphorescent luminescent material, and
wherein the organic compound layer is disposed between the luminescent layer and the anode and comprises the amino compound according to claim 1.

* * * * *